US012773118B2

(12) United States Patent
Paak et al.

(10) Patent No.: US 12,773,118 B2
(45) Date of Patent: Oct. 27, 2026

(54) METHOD AND SYSTEM TO ASSESS DISEASE USING DYNAMICAL ANALYSIS OF BIOPHYSICAL SIGNALS

(71) Applicant: Analytics For Life Inc., Toronto (CA)

(72) Inventors: Mehdi Paak, Toronto (CA); Timothy William Fawcett Burton, Toronto (CA); Shyamlal Ramchandani, Kingston (CA)

(73) Assignee: Analytics For Life Inc., Toronto (CA)

( * ) Notice: Subject to any disclaimer, the term of this patent is extended or adjusted under 35 U.S.C. 154(b) by 1363 days.

(21) Appl. No.: 16/831,264

(22) Filed: Mar. 26, 2020

(65) Prior Publication Data

US 2020/0397322 A1 Dec. 24, 2020

Related U.S. Application Data

(60) Provisional application No. 62/863,005, filed on Jun. 18, 2019, provisional application No. 62/862,991, filed on Jun. 18, 2019.

(51) Int. Cl.
*A61B 5/024* (2006.01)
*A61B 5/00* (2006.01)
(Continued)

(52) U.S. Cl.
CPC ........ *A61B 5/02433* (2013.01); *A61B 5/0205* (2013.01); *A61B 5/021* (2013.01);
(Continued)

(58) Field of Classification Search
None
See application file for complete search history.

(56) References Cited

U.S. PATENT DOCUMENTS 8,923,958 B2 12/2014 Gupta et al.
9,289,150 B1 3/2016 Gupta et al.
(Continued)

FOREIGN PATENT DOCUMENTS

CN 101801457 A 1/2014
CN 102686150 A 12/2014
(Continued)

OTHER PUBLICATIONS

Allen et al. Photoplethysmography assessments in cardiovascular disease; 2006 Meas. + Control vol. 39/3 (Year: 2006).*
(Continued)

*Primary Examiner* — Jay B Shah
(74) *Attorney, Agent, or Firm* — Meunier Carlin & Curfman LLC

(57) ABSTRACT

The exemplified methods and systems facilitate one or more dynamical analyses that can characterize and identify non-linear dynamical properties (such as Lyapunov exponent (LE), correlation dimension, entropy (K2), or statistical and/or geometric properties derived from Poincaré maps, etc.) of biophysical signals such as photoplethysmographic signals and/or cardiac signals to predict presence and/or localization of a disease or condition, or indicator of one, including, for example, but not limited to, coronary artery
(Continued)

disease, heart failure (including but not limited to elevated or abnormal left ventricular end-diastolic pressure disease) and pulmonary hypertension, among others.

8 Claims, 20 Drawing Sheets

(51) Int. Cl.

| | |
|---|---|
| ***A61B 5/0205*** | (2006.01) |
| ***A61B 5/021*** | (2006.01) |
| ***A61B 5/0245*** | (2006.01) |
| ***A61B 5/1455*** | (2006.01) |
| ***A61B 5/318*** | (2021.01) |

(52) U.S. Cl.

CPC ...... *A61B 5/02405* (2013.01); *A61B 5/02416* (2013.01); *A61B 5/02427* (2013.01); *A61B 5/0245* (2013.01); *A61B 5/14551* (2013.01); *A61B 5/318* (2021.01); *A61B 5/4842* (2013.01); *A61B 5/7239* (2013.01); *A61B 5/7246* (2013.01); *A61B 5/7264* (2013.01); *A61B 5/7275* (2013.01)

(56) References Cited

U.S. PATENT DOCUMENTS

| | | | |
|---|---|---|---|
| 9,408,543 | B1 | 8/2016 | Gupta et al. |
| 9,597,021 | B1 | 3/2017 | Gupta et al. |
| 9,737,229 | B1 | 8/2017 | Gupta et al. |
| 9,910,964 | B2 | 3/2018 | Burton et al. |
| 9,968,265 | B2 | 5/2018 | Burton et al. |
| 10,039,468 | B2 | 8/2018 | Gupta et al. |
| 2009/0326401 | A1 | 12/2009 | Jonckheere et al. |
| 2017/0119272 | A1 | 5/2017 | Gupta et al. |
| 2018/0000371 | A1 | 1/2018 | Gupta et al. |
| 2018/0033991 | A1 | 2/2018 | Yamashita |
| 2018/0078146 | A1 | 3/2018 | Shadforth et al. |
| 2018/0249960 | A1 | 9/2018 | Gupta et al. |
| 2018/0261328 | A1 | 9/2018 | Burton et al. |
| 2019/0026430 | A1 | 1/2019 | Grouchy et al. |
| 2019/0117164 | A1 | 4/2019 | Gupta et al. |
| 2019/0160917 | A1 | 5/2019 | Kim |
| 2019/0200893 | A1 | 7/2019 | Grouchy et al. |
| 2019/0214137 | A1 | 7/2019 | Gupta et al. |
| 2019/0365265 | A1 | 12/2019 | Grouchy et al. |
| 2019/0384757 | A1 | 12/2019 | Garrett et al. |
| 2020/0205739 | A1 | 7/2020 | Garrett et al. |
| 2020/0205745 | A1 | 7/2020 | Khousousi et al. |
| 2020/0211713 | A1 | 7/2020 | Shadforth et al. |

FOREIGN PATENT DOCUMENTS

| | | | |
|---|---|---|---|
| CN | 107920763 | A | 12/2021 |
| JP | 2007117591 | A | 5/2007 |
| JP | 2016064125 | A | 4/2016 |
| JP | 2017055880 | B3 | 3/2017 |
| WO | 2017137983 | A1 | 8/2017 |
| WO | 2019/075391 | | 4/2019 |

OTHER PUBLICATIONS

Du et al. Association between left ventricular end-diastolic pressure and coronary artery disease as well as its extent and severity; 2015; Int J Clin Exp Med 2015;8(10): 18673-18680 (Year: 2015).*

Allen, J., "Photoplethysmography and its application in clinical physiological measurement," Physiological Measurement, vol. 28, No. 3, 2007, pp. R1-R39.

Chatterjee, A., "An introduction to the proper orthogonal decomposition," Current Science, vol. 78, No. 7, 2000, pp. 808-817.

Chen, T., et al., "XGBoost: A Scalable Tree Boosting System," Proceedings of the 22nd International Conference on Knowledge Discovery and Data Mining (KDD'16), ACM, 2016, pp. 785-794.

"Executive Summary: Heart Disease and Stroke Statistics—2010 Update, A Report from the American Heart Association," Circulation, vol. 121, No. 7, 2010, pp. 948-954.

Fihn, S. D., et al., "2012 ACCF/AHA/ACP/AATS/PCNA/SCAI/STS Guideline for the Diagnosis and Management of Patients with Stable Ischemic Heart Disease: Executive Summary," Journal of the American College of Cardiology, vol. 60, No. 24, 2012, pp. 2564-2603.

Galiatsatos, P., et al., "Usefulness of a Noninvasive Device to Identify Elevated Left Ventricular Filling Pressure Using Finger Photoplethysmography During a Valsalva Maneuver," American Journal of Cardiology, vol. 119, No. 7, 2017, pp. 1053-1060.

Glass, L., "Synchronization and rhythmic processes in physiology," Nature, vol. 410, 2001, pp. 277-284.

Glass, L., et al., "Time Delays, Oscillations, and Chaos in Physiological Control Systems," Mathematical Biosciences, vol. 90, Issues 1-2, 1988, pp. 111-125.

Goldberger, A. L., et al., "Chaos and Fractals in Human Physiology," Scientific American, vol. 262, No. 2, 1990, pp. 43-49.

Goldberger, A. L. "Nonlinear dynamics, Fractals and Chaos: Applications to Cardiac Electrophysiology," Annals of Biomedical Engineering, vol. 18, No. 2, 1990, pp. 195-198.

Grassberger, P., et al., "Estimation of the Kolmogorov entropy from a chaotic signal," Rapid Communications, Physical Review A, vol. 28, No. 4, 1983, pp. 2591-2593.

Hansson, G. K., "Inflammation, atherosclerosis, and coronary artery disease," The New England Journal of Medicine, vol. 352, No. 16, 2005, pp. 1685-1695.

Jahmunah, V., et al., "Automated detection of schizophrenia using nonlinear signal processing methods," Artificial Intelligence in Medicine, vol. 100, 2019, 18 pages.

Kern, M. J., et al., "Hemodynamic Rounds Series II: The LVEDP," Catheterization and Cardiovascular Diagnosis, vol. 44, No. 1, 1998, pp. 70-74.

Kolmogorov, A. N., "On the Entropy per Unit of Time as a Metric Invariant of Automorphisms," C.R. (Doklady) Russian Academy of Sciences, No. 4, vol. 124, 1959, 3 pages.

Kononenko, I., "Machine Learning for Medical Diagnosis: History, State of the Art and Perspective," Artificial Intelligence in Medicine, vol. 23, No. 1, 2001, 25 pages.

Levine, G. N., et al., "2011 ACCF/AHA/SCAI Guideline for Percutaneous Coronary Intervention: Executive Summary," Journal of the American College of Cardiology, vol. 58, No. 24, 2011, pp. 2550-2583.

Mensah, G. A., et al., "An Overview of Cardiovascular Disease Burden in the United States," Health Affairs, vol. 26, No. 1, 2007, pp. 38-48.

Mielniczuk, L. M., et al., "Left Ventricular End-Diastolic Pressure and Risk of Subsequent Heart Failure in Patients Following an Acute Myocardial Infarction," Congestive Heart Failure, vol. 13, No. 4, 2007, pp. 209-214.

Mobley, B. A., et al., "Predictions of coronary artery stenosis by artificial neural network," Artificial Intelligence in Medicine, vol. 18, No. 3, 2000, pp. 187-203.

Ommen, S. R., et al., "Clinical Utility of Doppler Echocardiography and Tissue Doppler Imaging in the Estimation of Left Ventricular Filling Pressures, A Comparative Simultaneous Doppler-Catheterization Study," Circulation, vol. 102, No. 15, 2000, pp. 1788-1794.

Owis, M. I., et al., "Study of features based on nonlinear dynamical modeling in ECG arrhythmia detection and classification," IEEE Transactions on Biomedical Engineering, vol. 49, No. 7, 2002, pp. 733, 736.

Park, J.-H., et al., "Use and Limitations of E/e' to Assess Left Ventricular Filling Pressure by Echocardiography," Journal of Cardiovascular Ultrasound, vol. 19, No. 4, 2011, pp. 169-173.

Patel, V. L., et al., "The Coming of Age of Artificial Intelligence in Medicine," Artificial Intelligence in Medicine, vol. 46, No. 1, 2009, pp. 5-17.

Pedregosa, F., et al., "Scikit-learn: Machine Learning in Python," Journal of Machine Learning Research, vol. 12, 2011, pp. 2825-2830.

(56) References Cited

OTHER PUBLICATIONS

Reddy, Y. N., et al., "Comparing Pulmonary Arterial Wedge Pressure and Left Ventricular End Diastolic Pressure for Assessment of Left-Sided Filling Pressures," JAMA Cardiology, vol. 3, No. 6, 2018, pp. E1-E2.
Reisner, A., et al., "Utility of the Photoplethysmogram in Circulatory Monitoring," Anesthesiology, vol. 108, No. 5, 2008, pp. 950-958.
Russo, J. J., et al., "Left Ventricular Unloading During Extracorporeal Membrane Oxygenation in Patients with Cardiogenic Shock," Journal of the American College of Cardiology, vol. 73, No. 6, 2019, pp. 654-662.
Salem, R., et al., "Left ventricular end-diastolic pressure is a predictor of mortality in cardiac surgery independently of left ventricular ejection fraction," British Journal of Anaesthesia, vol. 97, No. 3, 2006, pp. 292-297.
Sauer, T., et al., "Embedology," Journal of Statistical Physics, vol. 65, Nos. 3-4, 1991, pp. 579-616.
Tai, A. M., et al., "Machine learning and big data: Implications for disease modeling and therapeutic discovery in psychiatry," Artificial Intelligence in Medicine, vol. 99, 2019, 11 pages.
Theiler, J., "Efficient Algorithm for Estimating the Correlation Dimension from a Set of Discrete Points," Physical Review A, vol. 36, No. 9, 1987, pp. 4456-4462.
Voss, A., et al., "Methods derived from nonlinear dynamics for analysing heart rate variability," Philosophical Transactions of the Royal Society A: Mathematical, Physical and Engineering Sciences, vol. 367, No. 1887, 2008, pp. 277-296.
Wolf, J. B., et al., "Determining Lyapunov Exponents from a Time Series," Physica D: Nonlinear Phenomena, vol. 16, No. 3, 1985, pp. 285-317.
Zou, H., et al., "Regularization and variable selection via the elastic net," Journal of the Royal Statistical Society: Series B (Statistical Methodology), vol. 67, Part 2, 2005, pp. 301-320.
International Search Report and Written Opinion, dated Jun. 23, 2020, received in connection with corresponding International Patent Application No. PCT/IB2020/052889.
Extended European Search Report issued for European Application No. 20827695.6, dated Aug. 17, 2023.
Voss Andreas et al: "Methods derived from nonlinear dynamics for analysing heart rate variability", Philosophical Transactions a .Mathematical, Physical and Engineering Sciences, the Royal Society, London, GB, vol. 367, No. 1887, Jan. 28, 2009 (Jan. 28, 2009), pp. 277-296.
Office Action and Search Report issued in corresponding Japanese Application No. 2021-575369, dated Dec. 12, 2023.
Office Action issued in corresponding Chinese Application No. 202080054093X, dated Jun. 17, 2024.
Final Office Action issued in corresponding Japanese Application No. 2021-575369, dated Jun. 25, 2024.
Office Action issued in corresponding Chinese Application No. 202080054093X, dated Feb. 18, 2025.

* cited by examiner

Photo Transistor

Dynamical Analysis of PPG Signal

| Feature Name | Disease State | Gender | t-test p-value | Mutual Information | ROC-AUC |
|---|---|---|---|---|---|
| SpAMILmin | CAD | Female | n/s | 1.288 | n/s |
| SpAMIUmin | CAD | Both Genders | n/s | 1.016 | n/s |
| SpD2L | LVEDP | Female | 4.34E-07 | n/s | n/s |
| SpD2U | LVEDP | Female | 3.82E-06 | n/s | n/s |
| | CAD | Male | 0.02 | n/s | n/s |
| SpK2L | LVEDP | Both Genders | 0.046 | n/s | n/s |
| SpK2U | LVEDP | Both Genders | 0.041 | n/s | n/s |
| SpXCFLUZ2 | LVEDP | Male | 0.045 | n/s | n/s |

*FIG. 4*

Dynamical Analysis of PSR/ECG Signal

| Feature Name | Disease State | Gender Division | t-test p-value (significant if < 0.05) | MI value (significant if > 1.0) | AUC (significant if > 0.50) | Feature Description |
|---|---|---|---|---|---|---|
| LEY | LVEDP | Male | 0.32 | 1.2 | n/s | Lyapunov exponent Y channel |
| D2X | CAD | Both Genders | 0.06 | n/s | 0.53 | Fractal Dimension (correlation dimension) D2 of X channel |
| D2Y | CAD | Both Genders | 0.002 | n/s | 0.52 | Fractal Dimension (correlation dimension) D2 of Y channel |
| K2X | LVEDP | Female | 0.3 | 1.03 | n/s | KS entropy (K2) of X channel |
| | CAD | Both Genders | 0.0002 | 1.32 | 0.56 | |
| K2Y | CAD | Both Genders | 0.0002 | 1.05 | 0.53 | KS entropy (K2) of Y channel |
| K2Z | CAD | Both Genders | 0.03 | 1.07 | 0.52 | KS entropy (K2) of Z channel |
| AMIYmin | CAD | Male | 0.02 | n/s | n/s | Minimum of auto mutual information of Y channel |
| AMIZmin | CAD | Both Genders | 0.03 | n/s | n/s | Minimum of auto mutual information of Z channel |
| ACFXZ1 | CAD | Both Genders | 0.43 | 1.05 | n/s | First zero crossing of auto-correlation function of X channel |
| ACFYZ1 | LVEDP | Male | 0.0001 | n/s | n/s | First zero crossing of auto-correlation function of Y channel signal |
| ACFZZ1 | LVEDP | Female | 0.04 | n/s | n/s | First zero crossing of auto-correlation function of Z channel |
| ACFXZ2 | CAD | Female | 0.03 | n/s | 0.51 | Second zero crossing of auto-correlation function of X channel |
| ACFYZ2 | LVEDP | Female | 0.001 | n/s | n/s | Second zero crossing of auto-correlation function of Y channel |
| | CAD | Both Genders | 0.09 | n/s | 0.51 | |
| ACFZZ2 | LVEDP | Female | 0.002 | n/s | n/s | Second zero crossing of auto-correlation function of Z channel |

FIG. 5

Dynamical Analysis of PSR/ECG Signal

| Feature Name | Disease State | Gender Division | t-test p-value (significant if < 0.05) | MI value (significant if > 1.0) | AUC (significant if > 0.50) | Feature Description |
|---|---|---|---|---|---|---|
| XCFYZMax | LVEDP | Female | 0.79 | 1.03 | n/s | Maximum cross correlation function between Y and Z channels |
| | CAD | Female | 0.98 | 1.13 | n/s | |
| XCFXYMax | LVEDP | Female | 0.0004 | n/s | n/s | Maximum value of cross-correlation between X and Y channels |
| XCFXZMax | LVEDP | Both Genders | 0.04 | n/s | n/s | Maximum cross correlation function between X and Z channels |
| | CAD | Both Genders | 0.13 | 1.03 | n/s | |
| XMIXYR | LVEDP | Female | 0.04 | n/s | n/s | Cross Mutual Information Ratio : $I_{xy}/(I_{xx}*I_{yy})$ |
| XMIXZR | LVEDP | Both Genders | 0.02 | n/s | n/s | Cross Mutual Information Ratio : $I_{xz}/(I_{xx}*I_{zz})$ |
| XCFXZ1 | CAD | Both Genders | 0.002 | 1.59 | 0.54 | Value of cross-correlation between X and Z at lag zero (no lag) |
| XCFXZZ1 | CAD | Both Genders | 0.0005 | 1.16 | 0.56 | First zero crossing of cross-correlation between X and Z channels |
| XCFYZZ2 | LVEDP | Female | 0.004 | n/s | n/s | Second zero crossing of cross-correlation between Y and Z |
| XCFYZDelay | CAD | Both Genders | 0.04 | n/s | n/s | Delay/lag between Y and Z channels in cross-correlation between Y and Z channels |

*FIG. 5 (cont.)*

Dynamical Analysis of Poincare Map of PPG signal

| Feature Name | Disease State | Gender | t-test p-value | Mutual Information | ROC-AUC |
|---|---|---|---|---|---|
| alphaShapePoincareOutput. alphaShapeDensity | CAD | Both Genders | n/s | n/s | 0.538 |
| alphaShapePoincareOutput. convexSurfaceArea | CAD | Both Genders | n/s | n/s | 0.533 |
| alphaShapePoincareOutput. perim | CAD | Both Genders | 0.044 | 1.295 | 0.523 |
| alphaShapePoincareOutput. perimSurfaceAreaRatio | CAD | Both Genders | 0.00001 | 1.841 | 0.566 |
| | LVEDP | Both Genders | 0.011 | n/s | n/s |
| alphaShapePoincareOutput. porosity | CAD | Both Genders | 0.035 | n/s | 0.509 |
| alphaShapePoincareOutput. surfaceArea | CAD | Both Genders | n/s | n/s | 0.549 |
| alphaShapePoincareOutput. voidArea | CAD | Both Genders | n/s | n/s | 0.505 |
| histSD | CAD | Both Genders | n/s | n/s | 0.506 |
| largestClusterEllipse.a | CAD | Both Genders | n/s | n/s | 0.502 |
| largestClusterEllipse.b | CAD | Male | n/s | n/s | 0.502 |
| largestClusterEllipse. long_axis | CAD | Both Genders | n/s | 1.37 | 0.508 |
| largestClusterEllipse. short_axis | CAD | Both Genders | n/s | 1.086 | 0.527 |
| largestClusterEllipse.X0 | CAD | Female | n/s | 1.04 | n/s |
| numberOfKernelDensityModes | CAD | Male | 0.049 | n/s | n/s |
| numClusters | LVEDP | Female | 0.013 | n/s | n/s |
| sarleBiomodalityCoeff | LVEDP | Male | n/s | 1.234 | n/s |
| | CAD | Both Genders | 0.045 | n/s | n/s |

FIG. 16

METHOD AND SYSTEM TO ASSESS DISEASE USING DYNAMICAL ANALYSIS OF BIOPHYSICAL SIGNALS

CROSS REFERENCE TO RELATED APPLICATIONS

This utility patent application claims priority to, and the benefit of, U.S. Provisional Patent application No. 62/863,005, filed Jun. 18, 2019, entitled "Method and System to Assess Disease Using Dynamical Analysis of Cardiac and Photoplethysmographic Signals" and U.S. Provisional Patent application No. 62/862,991, filed Jun. 18, 2019, entitled "Method and System to Assess Disease Using Dynamical Analysis of Biophysical Signals", each of which is incorporated by reference herein in its entirety.

FIELD OF THE INVENTION

The present disclosure generally relates to non-invasive methods and systems for characterizing one or more physiological systems and their associated functions, activities, and abnormalities. More specifically, in an aspect, the present disclosure relates to non-invasive methods that utilize plethysmographic-related measurements, alone or in conjunction with other types of measurements of physiological phenomena and systems, to predict and/or detect the presence, non-presence, severity, and/or localization of cardiovascular, pulmonary and cardiopulmonary disease, processes or conditions, among others. In another aspect, the present disclosure relates to non-invasive methods that utilize cardiac-related measurements for the same. In another aspect, the present disclosure relates to non-invasive methods that utilize both plethysmographic- and cardiac-related measurements for the same.

BACKGROUND

The term "biophysical signal", as described in greater detail below, encompasses any physiological signal from which information may be obtained. Without wishing to be limiting, biophysical signals may be in part characterized by the form of energy such signals take (for example electrical, acoustic, chemical, thermal, magnetic, optical, etc.) by one or more physiological systems from which they may originate and/or be associated (e.g., circulatory/cardiovascular, nervous, respiratory, and the like), by associated organ systems, by tissue type, by cellular type, by cellular components such as organelles, etc., including combinations thereof. Biophysical signals may be acquired passively or actively, or both.

Often, biophysical signals are acquired in connection with or via invasive or minimally invasive techniques (e.g., via a catheterization) and/or the use of radiation (e.g., nuclear imaging), exercise/stress (e.g., treadmill or nuclear stress test) and/or the administration of pharmacological and/or other agents (e.g., vasodilators, contrast agents). These various modalities can modestly or even significantly increase the cost of acquiring such signals, as they may need to be administered in specialized settings, often via expensive equipment that often requires the patient travel to use, and even sometimes requiring an overnight stay in, e.g., a hospital or hotel. Some of these modalities can increase the risk to the patient for adverse effects such as, e.g., infection or an allergic reaction. Some modalities expose the patient to doses of undesirable radiation. And in the case of, e.g., exercise or treadmill tests can trigger modest or even serious adverse events (e.g., myocardial infarction) that would otherwise not have happened. Moreover, these various modalities generally increase the amount of time required to ascertain the state of health, disease, or condition of the patient whose biophysical signals are being characterized, sometimes on the order of weeks or months—often for a patient who is or may be suffering from a modest or even serious health condition. This results in lost work productivity and higher overall healthcare costs for society. Such delays can also exact an emotional toll on the patient (which itself can be deleterious to the patient's health), their family, friends and other caregivers tending to the needs of the patient.

As such, it is desirable to obtain information from biophysical signals that minimize or even eliminate the need to use invasive and/or minimally invasive techniques, radiation, exercise/stress and/or the use of pharmacological and/or other agents so that assessing (e.g., predict and/or detect) the presence, non-presence, severity and (in some cases) localization of various diseases, pathologies or conditions in mammalian or non-mammalian organisms may be accomplished more safely, with lower costs, and/or in a shorter amount of time than current methods and systems provide.

The methods and systems described herein address this need and may be used for a wide variety of clinical and even research needs in a wide variety of settings—from hospitals to emergency rooms, laboratories, battlefield or remote settings, at point of care with a patient's primary care physician or other caregiver, and even the home. Without being limiting, the following description provides example methods and systems for such use in the context of cardiac- or cardiovascular-related disease states and conditions; most particularly pulmonary hypertension (PH) in its various forms, coronary artery disease (CAD) in its various forms, and heart failure in its various forms.

SUMMARY

The exemplified methods and systems facilitate one or more dynamical analyses that can characterize and identify nonlinear dynamical properties (such as Lyapunov exponent (LE), correlation dimension, entropy (K2), or statistical and/or geometric properties derived from Poincaré maps, etc.) of biophysical signals such as photoplethysmographic signals and/or cardiac signals to predict presence and/or localization of a disease or condition, or indicator of one, including, for example, but not limited to, coronary artery disease, heart failure (including but not limited to abnormal left ventricular end-diastolic pressure disease) and pulmonary hypertension, among others.

In some embodiments, dynamical systems and nonlinear dynamics features such as entropy rate "K2", correlation dimension "D2" of fractal dimension, Lyapunov exponent ("LE"), mutual information (MI) and correlation (XC) are extracted. In some embodiments, one or more features associated with Poincaré maps are extracted.

A "cardiac signal" as used herein refers to one or more signals associated with the structure, function and/or activity of the cardiovascular system—including aspects of that signal's electrical/electrochemical conduction—that, e.g., cause contraction of the myocardium. A cardiac signal may include, in some embodiments, electrocardiographic signals such as, e.g., those acquired via an electrocardiogram (ECG) or other modalities.

A "photoplethysmographic signal(s)" as used herein refers to signal waveforms acquired from optical sensors that corresponds to measured changes in light absorption by oxygenated and deoxygenated hemoglobin, such as light having wavelengths in the red and infrared spectrum. Photoplethysmographic signal(s), in some embodiments, include raw signal(s) acquired via a pulse oximeter or a photoplethysmogram (PPG). In some embodiments, photoplethysmographic signal(s) are acquired from custom or dedicated equipment or circuitries (including off-the-shelf devices) that are configured to acquire such signal waveforms for the purpose of diagnosing disease or abnormal conditions. The photoplethysmographic signal(s) typically include a red photoplethysmographic signal (e.g., an electromagnetic signal in the visible light spectrum most dominantly having a wavelength of approximately 625 to 740 nanometers) and an infrared photoplethysmographic signal (e.g., an electromagnetic signal extending from the nominal red edge of the visible spectrum up to about 1 mm), though other spectra such as near infrared, blue and green may be used in different combinations, depending on the type and/or mode of photoplethysmographic-related measurement being employed.

A "biophysical signal" is not limited to a cardiac signal, a neurological signal, or a photoplethysmographic signal but encompasses any physiological signal from which information may be obtained. Not intending to be limited by example, one may classify biophysical signals into types or categories that can include, for example, electrical (e.g., certain cardiac and neurological system-related signals that can be observed, identified and/or quantified by techniques such as the measurement of voltage/potential, impedance, resistivity, conductivity, current, etc. in various domains such as time and/or frequency), magnetic, electromagnetic, optical (e.g. signals that can be observed, identified and/or quantified by techniques such as reflectance, interferometry, spectroscopy, absorbance, transmissivity, visual observation, photoplethysmography, and the like), acoustic, chemical, mechanical (e.g., signals related to fluid flow, pressure, motion, vibration, displacement, strain), thermal, and electrochemical (e.g. signals that can be correlated to the presence of certain analytes, such as glucose). Biophysical signals may in some cases be described in the context of a physiological system (e.g., respiratory, circulatory (cardiovascular, pulmonary), nervous, lymphatic, endocrine, digestive, excretory, muscular, skeletal, renal/urinary/excretory, immune, integumentary/exocrine and reproductive systems), an organ system (e.g., signals that may be unique to the heart and lungs as they work together), or in the context of tissue (e.g., muscle, fat, nerves, connective tissue, bone), cells, organelles, molecules (e.g., water, proteins, fats, carbohydrates, gases, free radicals, inorganic ions, minerals, acids, and other compounds, elements and their subatomic components. Unless stated otherwise, the term "biophysical signal acquisition" generally refers to any passive or active means of acquiring a biophysical signal from a physiological system, such as a mammalian or non-mammalian organism. Passive and active biophysical signal acquisition generally refers to the observation of natural or induced electrical, magnetic, optical, and/or acoustics emittance of the body tissue. Non-limiting examples of passive and active biophysical signal acquisition means include, e.g., voltage/potential, current, magnetic, optical, acoustic and other non-active ways of observing the natural emittance of the body tissue, and in some instances, inducing such emittance. Non-limiting examples of passive and active biophysical signal acquisition means include, e.g., ultrasound, radio waves, microwaves, infrared and/or visible light (e.g., for use in pulse oximetry or photoplethysmography), visible light, ultraviolet light and other ways of actively interrogating the body tissue that does not involve ionizing energy or radiation (e.g., X-ray). Active biophysical signal acquisition may involve excitation-emission spectroscopy (including, e.g., excitation-emission fluorescence). Active biophysical signal acquisition may also involve transmitting ionizing energy or radiation (e.g., X-ray) (also referred to as "ionizing biophysical signal") to the body tissue. Passive and active biophysical signal acquisition means can be performed with conjunction with invasive procedures (e.g., via surgery or invasive radiologic intervention protocols) or non-invasively (e.g., via imaging).

The methods and systems described in the various embodiments herein are not so limited and may be utilized in any context of another physiological system or systems, organs, tissue, cells, etc. of a living body. By way of example only, two biophysical signal types that may be useful in the cardiovascular context include cardiac signals that may be acquired via conventional electrocardiogram (ECG/EKG) equipment, bipolar wide-band biopotential (cardiac) signals that may be acquired from other equipment such as those described herein, and signals that may be acquired by various plethysmographic techniques, such as, e.g., photoplethysmography.

In the context of the present disclosure, techniques for acquiring and analyzing biophysical signals are described in particular for use in diagnosing the presence, non-presence, localization (where applicable), and/or severity of certain disease states or conditions in, associated with, or affecting, the cardiovascular (or cardiac) system, including for example pulmonary hypertension (PH), coronary artery disease (CAD), and heart failure (e.g., left-side or right-side heart failure).

Pulmonary hypertension, heart failure, and coronary artery disease are three diseases/conditions affiliated with the cardiovascular or cardiac system. Pulmonary hypertension (PH) generally refers to high blood pressure in the arteries of the lungs and can include a spectrum of conditions. PH typically has a complex and multifactorial etiology and an insidious clinical onset with varying severity. PH may progress to complications such as right heart failure and in many cases is fatal. The World Health Organization (WHO) has classified PH into five groups or types. The first PH group classified by the WHO is pulmonary arterial hypertension (PAH). PAH is a chronic and currently incurable disease that, among other things, causes the walls of the arteries of the lungs to tighten and stiffen. PAH requires at a minimum a heart catheterization for diagnosis. PAH is characterized by vasculopathy of the pulmonary arteries and defined, at cardiac catheterization, as a mean pulmonary artery pressure of 25 mm Hg or more. One form of pulmonary arterial hypertension is known as idiopathic pulmonary arterial hypertension—PAH that occurs without a clear cause. Among others, subcategories of PAH include heritable PAH, drug and toxin induced PAH, and PAH associated with other systemic diseases such as, e.g., connective tissue disease, HIV infection, portal hypertension, and congenital heart disease. PAH includes all causes that lead to the structural narrowing of the pulmonary vessels. With PAH, progressive narrowing of the pulmonary arterial bed results from an imbalance of vasoactive mediators, including prostacyclin, nitric oxide, and endothelin-1. This leads to an increased right ventricular afterload, right heart failure, and premature death. The second PH group as classified by the WHO is pulmonary hypertension due to left heart disease. This group of disorders is generally characterized by problems with the left side of the heart. Such problems can, over time, lead to changes within the pulmonary arteries. Specific subgroups include left ventricular systolic dysfunction, left ventricular diastolic dysfunction, valvular disease and, finally, congenital cardiomyopathies and obstructions not due to valvular disease. Treatments of this second PH group tends to focus on the underlying problems (e.g., surgery to replace a heart valve, various medications, etc.). The third PH group as classified by the WHO is large and diverse, generally relating to lung disease or hypoxia. Subgroups include chronic obstructive pulmonary disease, interstitial lung disease, sleep breathing disorders, alveolar hypoventilation disorders, chronic high altitude exposure, and developmental lung disease. The fourth PH group is classified by the WHO as chronic thromboembolic pulmonary hypertension, caused when blood clots enter or form within the lungs, blocking the flow of blood through the pulmonary arteries. The fifth PH group is classified by the WHO as including rare disorders that lead to PH, such as hematologic disorders, systemic disorders such as sarcoidosis that have lung involvement, metabolic disorders, and a subgroup of other diseases. The mechanisms of PH in this fifth group are poorly understood.

PH in all of its forms can be difficult to diagnose in a routine medical examination because the most common symptoms of PH (shortness of breath, fatigue, chest pain, edema, heart palpitations, dizziness) are associated with so many other conditions. Blood tests, chest x-rays, electro- and echocardiograms, pulmonary function tests, exercise tolerance tests, and nuclear scans are all used variously to help a physician to diagnose PH in its specific form. As noted above, the “gold standard” for diagnosing PH, and for PAH in particular, is a cardiac catheterization of the right side of the heart by directly measuring the pressure in the pulmonary arteries. If PAH is suspected in a subject, one of several investigations may be performed to confirm the condition, such as electrocardiography, chest radiography, and pulmonary function tests, among others. Evidence of right heart strain on electrocardiography and prominent pulmonary arteries or cardiomegaly on chest radiography is typically seen. However, a normal electrocardiograph and chest radiograph cannot necessarily exclude a diagnosis of PAH. Further tests may be needed to confirm the diagnosis and to establish cause and severity. For example, blood tests, exercise tests, and overnight oximetry tests may be performed. Yet further, imaging testing may also be performed. Imaging testing examples include isotope perfusion lung scanning, high resolution computed tomography, computed tomography pulmonary angiography, and magnetic resonance pulmonary angiography. If these (and possibly other) non-invasive investigations support a diagnosis of PAH, right heart catheterization typically is needed to confirm the diagnosis by directly measuring pulmonary pressure. It also allows measurement of cardiac output and estimation of left atrial pressure using pulmonary arterial wedge pressure. While non-invasive techniques exist to determine whether PAH may exist in a subject, these techniques cannot reliably confirm a diagnosis of PAH unless an invasive right heart catheterization is performed. Aspects and embodiments of methods and systems for assessing PH are disclosed in commonly-owned U.S. patent application Ser. No. 16/429,593, the entirety of which is hereby incorporated by reference.

Heart failure affects almost 6 million people in the United States alone, and more than 870,000 people are diagnosed with heart failure each year. The term “heart failure” (sometimes referred to as congestive heart failure or CHF) generally refers to a chronic, progressive condition or process in which the heart muscle is unable to pump enough blood to meet the needs of the body, either because the heart muscle is weakened or stiff or because a defect is present that prevents proper circulation. This results in, e.g., blood and fluid backup into the lungs, edema, fatigue, dizziness, fainting, rapid and/or irregular heartbeat, dry cough, nausea and shortness of breath.

HF is a complex disorder encompassing a wide range of symptoms which may result from multiple diverse pathologies. The clinical syndrome can occur from any structural or functional cardiac alteration that impairs the ability of the ventricle to fill with or eject blood. Patients typically fall into two distinct groups, grouped by left ventricular (LV) ejection fraction (LVEF): 1) HF with reduced LVEF (HFrEF [LVEF≤40%]) and 2) HF with preserved LVEF (HFpEF [LVEF≥50%]). While the defining property of HFrEF is systolic dysfunction, and by contrast, that of HFpEF is diastolic dysfunction, both can occur to vary degrees within both HFrEF and HFpEF. Of the 6+ million Americans with the diagnosis, there exists an approximately even distribution between these two categories. In addition, the two groups have a similar mortality at 5 years, estimates of which range between 50-75%.

Common causes of heart failure are coronary artery disease (CAD), high blood pressure, cardiomyopathy, arrhythmia, kidney disease, heart defects, obesity, tobacco use and diabetes. Diastolic heart failure (DHF), left- or left-sided heart failure/disease (also referred to as left ventricular heart failure), right- or right-sided heart failure/disease (also referred to as right ventricular heart failure) and systolic heart failure (SHF) are common types of heart failure.

Left-sided heart failure is further classified into two main types: systolic failure (or heart failure with reduced ejection fraction or reduced left ventricular function) and diastolic failure/dysfunction (or heart failure with preserved ejection fraction or preserved left ventricular function). Procedures and technologies commonly used to determine if a patient has left-sided heart failure include cardiac catheterization, x-ray, echocardiogram, electrocardiogram (EKG), electrophysiology study, radionucleotide imaging, and various treadmill tests, including a test that measures peak $VO_2$. Ejection fraction (EF), which is a measurement expressed as a percentage of how much blood a ventricle pumps out with each contraction (and in the case of left-sided heart failure the left ventricle), is most often obtained non-invasively via an echocardiogram. A normal left ventricular ejection fraction (LVEF) ranges from about 55% to about 70%.

When systolic failure occurs, the left ventricle cannot contract forcefully enough to keep blood circulating normally throughout the body, which deprives the body of a normal supply of blood. As the left ventricle pumps harder to compensate, it grows weaker and thinner. As a result, blood flows backwards into organs, causing fluid buildup in the lungs and/or swelling in other parts of the body. Echocardiograms, magnetic resonance imaging, and nuclear medicine scans (e.g., multiple gated acquisition) are techniques used to noninvasively measure ejection fraction (EF), expressed as a percentage of the volume of blood pumped by the left ventricle relative to its filling volume to aid in the diagnosis of systolic failure. In particular, left ventricular ejection fraction (LVEF) values below 55% indicate the pumping ability of the heart is below normal, and can in severe cases be measured at less than about 35%. In general, a diagnosis of systolic failure can be made or aided when these LVEF values are below normal.

When diastolic heart failure occurs, the left ventricle has grown stiff or thick, losing its ability to relax normally, which in turn means that the lower left chamber of the heart is unable to properly fill with blood. This reduces the amount of blood pumped out to the body. Over time, this causes blood to build up inside the left atrium, and then in the lungs, leading to fluid congestion and symptoms of heart failure. In this case, LVEF values tend to be preserved within the normal range. As such, other tests, such as an invasive catheterization may be used to measure the left ventricular end diastolic pressure (LVEDP) to aid in the diagnosis of diastolic heart failure as well as other forms of heart failure with preserved EF. Typically, LVEDP is measured either directly by the placement of a catheter in the left ventricle or indirectly by placing a catheter in the pulmonary artery to measure the pulmonary capillary wedge pressure. Such catheterization techniques, by their nature, increase the risk of infection and other complications to the patient and tend to be costly. As such, non-invasive methods and systems for determining or estimating LVEDP in diagnosing the presence or non-presence and/or severity of diastolic heart failure as well as myriad other forms of heart failure with preserved EF are desirable. In addition, non-invasive methods and systems for diagnosing the presence or non-presence and/or severity of diastolic heart failure as well as myriad other forms of heart failure with preserved EF, without necessarily including a determination or estimate of an abnormal LVEDP, are desirable. Embodiments of the present disclosure address all of these needs.

Right-sided heart failure often occurs due to left-sided heart failure, when the weakened and/or stiff left ventricle loses power to efficiently pump blood to the rest of the body. As a result, fluid is forced back through the lungs, weakening the heart's right side, causing right-sided heart failure. This backward flow backs up in the veins, causing fluid to swell in the legs, ankles, GI tract and liver. In other cases, certain lung diseases such as chronic obstructive pulmonary disease and pulmonary fibrosis can cause right-sided heart failure, despite the left side of the heart functioning normally. Procedures and technologies commonly used to determine if a patient has left-sided heart failure include a blood test, cardiac CT scan, cardiac catheterization, x-ray, coronary angiography, echocardiogram, electrocardiogram (EKG), myocardial biopsy, pulmonary function studies, and various forms of stress tests such as a treadmill test.

Pulmonary hypertension is closely associated with heart failure. As noted above, PAH (the first WHO PH group) can lead to an increased right ventricular afterload, right heart failure, and premature death. PH due to left heart failure (the second WHO PH group) is believed to be the most common cause of PH.

Ischemic heart disease, also known as cardiac ischemia or myocardial ischemia, and related condition or pathologies, may also be estimated or diagnosed with the techniques disclosed herein. Ischemic heart disease is a disease or group of diseases characterized by a reduced blood supply to the heart muscle, usually due to coronary artery disease (CAD). CAD is closely related to heart failure and is its most common cause. CAD typically occurs when the lining inside the coronary arteries that supply blood to the myocardium, or heart muscle, develops atherosclerosis (the hardening or stiffening of the lining and the accumulation of plaque therein, often accompanied by abnormal inflammation). Over time, CAD can also weaken the heart muscle and contribute to, e.g., angina, myocardial infarction (cardiac arrest), heart failure, and arrhythmia. An arrhythmia is an abnormal heart rhythm and can include any change from the normal sequence of electrical conduction of the heart and in some cases can lead to cardiac arrest. The evaluation of PH, heart failure, CAD and other diseases and/or conditions can be complex, and many invasive techniques and tools are used to assess the presence and severity of the conditions as noted above. In addition, the commonalities among symptoms of these diseases and/or conditions as well as the fundamental connection between the respiratory and cardiovascular systems—due to the fact that they work together to oxygenate the cells and tissues of the body—point to a complex physiological interrelatedness that may be exploited to improve the detection and ultimate treatment of such diseases and/or conditions. Conventional methodologies to assess these biophysical signals in this context still pose significant challenges in giving healthcare providers tools for accurately detecting/diagnosing the presence or non-presence of such diseases and conditions.

For example, in electrocardiography—a field of cardiology in which the heart's electrical activity is analyzed to obtain information about its structure and function—it has been observed that significant ischemic heart disease can alter ventricular conduction properties of the myocardium in the perfusion bed downstream of a coronary artery narrowing or occlusion, the pathology can express itself at different locations of the heart and at different stages of severity, making an accurate diagnosis challenging. Further, the electrical conduction characteristics of the myocardium may vary from person to person, and other factors such as measurement variability associated with the placement of measurement probes and parasitic losses associated with such probes and their related components can also affect the biophysical signals that are captured during electrophysiologic tests of the heart. Further still, when conduction properties of the myocardium are captured as relatively long cardiac phase gradient signals, they may exhibit complex nonlinear variability that cannot be efficiently captured by traditional modeling techniques.

Indeed, the exemplified methods and systems facilitate one or more dynamical analyses that can characterize and identify nonlinear dynamical properties (such as Lyapunov exponent (LE), correlation dimension, entropy (K2), or statistical and/or geometric properties derived from Poincaré maps, etc.) of biophysical signals such as photoplethysmographic signals and/or cardiac signals to predict presence and/or localization of a disease or condition, or indicator of one, including, for example, but not limited to, coronary artery disease, heart failure (including but not limited to abnormal left ventricular end-diastolic pressure disease) and pulmonary hypertension, among others.

In some embodiments, the dynamical features include at least a determined correlation dimension of an acquired photoplethysmographic signal (e.g., red photoplethysmographic signal or an infrared photoplethysmographic signal). Notably, it has been observed that this assessed dynamical feature is linked to abnormal left ventricular end-diastolic pressure (LVEDP) and may be used to predict for the presence, non-presence, and/or severity of such condition in a clinical setting. As discussed above, LVEDP is considered a measure of ventricular performance, particularly left ventricular performance, and is often used to identify patients at increased risk of developing late clinical symptoms of heart failure (HF). Elevated LVEDP has been observed to be common following myocardial infarction; however, it has been accepted to be an independent predictor of subsequent HF risk. In some embodiments, the dynamical features include at least an assessed property of a Poincaré map object derived from waveforms of adjacent heart cycles. The assessed property, in some embodiments, includes a ratio of perimeter values of the Poincaré map object (e.g., from an infrared measurement). In some embodiments, the assessed property includes a surface area of Poincaré map object.

In an aspect, a method is disclosed for non-invasively assessing a disease state or abnormal condition of a subject, the method comprising: obtaining, by one or more processors (e.g., from a stored database or from a measurement system), a biophysical signal data set of a subject (e.g., one or more photoplethysmographic signals or cardiac signals); determining, by the one or more processors, one or more dynamical properties of the biophysical signal data set; and determining, by the one or more processors, one or more estimated values for the presence, non-presence, localization, and/or severity of a disease or condition based on the determined one or more dynamical properties.

In some embodiments, the presence, non-presence, and/or severity of a disease or condition can be assessed based on an assessment of left ventricular end-diastolic pressure (LVEDP), including an elevated or abnormal LVEDP.

In some embodiments, the disease state or condition includes significant coronary artery disease.

In some embodiments, the disease state or condition includes pulmonary hypertension.

In some embodiments, the disease state or condition includes pulmonary arterial hypertension (PAH).

In some embodiments, the disease state or condition includes pulmonary hypertension due to left heart disease.

In some embodiments, the disease state or condition includes a rare disorder that can lead to pulmonary hypertension.

In some embodiments, the disease state or condition includes left ventricular heart failure or left-sided heart failure.

In some embodiments, the disease state or condition includes right ventricular heart failure or right-sided heart failure.

In some embodiments, the disease state or condition includes systolic heart failure (SHF).

In some embodiments, the disease state or condition includes diastolic heart failure (DHF).

In some embodiments, the disease state or condition includes ischemic heart disease.

In some embodiments, the disease state or condition includes arrhythmia.

In some embodiments, the method further includes determining, by the one or more processors, one or more second estimated values for the presence, non-presence, localization, and/or severity of two or more of the diseases or conditions.

In some embodiments, the dynamical property is selected from the group consisting of entropy value (K2), fractal dimension (D2), Lyapunov exponent, auto correlation, auto mutual information, cross-correlation, and mutual information.

In some embodiments, the obtained biophysical signal data set comprises one or more red photoplethysmographic signals.

In some embodiments, the obtained biophysical signal data set comprises one or more infrared photoplethysmographic signals.

In some embodiments, the obtained biophysical signal data set comprises one or more cardiac signals.

In some embodiments, the method further includes causing, by the one or more processors, generation of a visualization of the estimated value for the presence, non-presence, localization, and/or severity of the disease or condition, wherein the generated visualization is rendered and displayed at a display of a computing device (e.g., computing workstation; a surgical, diagnostic, or instrumentation equipment) and/or presented in a report (e.g., an electronic report).

In some embodiments, the method further includes determining, by the one or more processors, a histogram map of variance in periodicity in the biophysical signal data set, wherein the histogram map is used in the determination of the estimated value for the presence, non-presence, localization, and/or severity of the disease or condition.

In some embodiments, the method further includes determining, by the one or more processors, a Poincaré map of the obtained biophysical signal data set; determining, by the one or more processors, an alpha shape object of the Poincaré map; and determining, by the one or more processors, one or more geometric properties of the alpha shape object, wherein the one or more determined geometric properties is used in the determination of the estimated value for the presence, non-presence, localization, and/or severity of the disease or condition.

In some embodiments, the one or more determined geometric properties further includes two or more properties selected from the group of: a density value of the alpha shape object; a convex surface area value of the alpha shape object; a perimeter value of the alpha shape object; a porosity value of the alpha shape object; and a void area value of the alpha shape object.

In some embodiments, the one or more determined geometric properties further includes two or more properties selected from the group of: a length of semi axis "a" for an assessed largest cluster ellipse of the Poincaré map; a length of semi axis "b" for an assessed largest cluster ellipse of the Poincaré map; a length of a longest axis of an assessed largest cluster ellipse of the Poincaré map; a length of a shortest axis of an assessed largest cluster ellipse of the Poincaré map; an assessed number of clusters in the Poincaré map; n assessed number of kernel density modes in the histogram map; and a Sarles bimodality coefficient value assessed from the histogram map.

In another aspect, a method is disclosed for non-invasively assessing a disease state or abnormal condition of a subject, the method comprising: obtaining, by one or more processors (e.g., from a stored database or from a measurement system), a biophysical signal data set of a subject (e.g., a photoplethysmographic signal); determining, by the one or more processors, Poincaré map of variance in the biophysical signal data set; determining, by the one or more processors, an alpha shape object of the Poincaré map; determining, by the one or more processors, one or more geometric properties of the alpha shape object; and determining, by the one or more processors, an estimated value for presence, non-presence, localization, and/or severity of a disease or condition based on the determined one or more geometric properties, wherein the disease state includes presence of coronary artery disease (e.g., significant coronary artery disease) or elevated/abnormal left ventricular end-diastolic pressure.

In some embodiments, the determined Poincaré map is generated by plotting photoplethysmographic signal peaks at a first time x−1 to a second time x in a first axis and at the second time x to a third time x+1 in a second axis.

Indeed, in a Poincaré map, reference to time is synonymous, and thus can be used interchangeably, with respect to a data point in a given data set.

In another aspect, a system is disclosed for non-invasively assessing a disease state or abnormal condition of a subject, the system comprising: a processor; and a memory having instructions stored thereon, wherein execution of the instructions by the processor, cause the processor to: obtain (e.g., from a stored database or from a measurement system), a biophysical signal data set of a subject (e.g., one or more photoplethysmographic signals or cardiac signals); determine one or more dynamical properties of the biophysical signal data set; and determine one or more estimated values for the presence, non-presence, localization, and/or severity of a disease or condition based on the determined one or more dynamical properties.

In some embodiments, execution of the instructions by the processor, further cause the processor to determine one or more second estimated values for the presence, non-presence, localization, and/or severity of two or more of the diseases or conditions.

In some embodiments, the dynamical property is selected from the group consisting of entropy value (K2), fractal dimension (D2), Lyapunov exponent, auto correlation, auto mutual information, cross-correlation, and mutual information.

In some embodiments, the obtained biophysical signal data set comprises one or more red photoplethysmographic signals.

In some embodiments, the obtained biophysical signal data set comprises one or more infrared photoplethysmographic signals.

In some embodiments, the obtained biophysical signal data set comprises one or more cardiac signals.

In some embodiments, execution of the instructions by the processor, further cause the processor to cause generation of a visualization of the estimated value for the presence, non-presence, localization, and/or severity of the disease or condition, wherein the generated visualization is rendered and displayed at a display of a computing device (e.g., computing workstation; a surgical, diagnostic, or instrumentation equipment) and/or presented in a report (e.g., an electronic report).

In some embodiments, execution of the instructions by the processor, further cause the processor to determine a histogram map of variance in periodicity in the biophysical signal data set, wherein the histogram map is used in the determination of the estimated value for the presence, non-presence, localization, and/or severity of the disease or condition.

In some embodiments, execution of the instructions by the processor, further cause the processor to determine a Poincaré map of the obtained biophysical signal data set; determine an alpha shape object of the Poincaré map; and determine one or more geometric properties of the alpha shape object, wherein the one or more determined geometric properties is used in the determination of the estimated value for the presence, non-presence, localization, and/or severity of the disease or condition.

In some embodiments, the one or more determined geometric properties further includes two or more properties selected from the group of a density value of the alpha shape object; a convex surface area value of the alpha shape object; a perimeter value of the alpha shape object; a porosity value of the alpha shape object; and a void area value of the alpha shape object.

In some embodiments, the one or more determined geometric properties further includes two or more properties selected from the group of a length of semi axis "a" for an assessed largest cluster ellipse of the Poincaré map; a length of semi axis "b" for an assessed largest cluster ellipse of the Poincaré map; a length of a longest axis of an assessed largest cluster ellipse of the Poincaré map; a length of a shortest axis of an assessed largest cluster ellipse of the Poincaré map; an assessed number of clusters in the Poincaré map; an assessed number of kernel density modes in the histogram map; and a Sarles bimodality coefficient value assessed from the histogram map.

In some embodiments, the system is further configured to obtain (e.g., from a stored database or from a measurement system), a biophysical signal data set of a subject (e.g., a photoplethysmographic signal); determine Poincaré map of variance in the biophysical signal data set; determine an alpha shape object of the Poincaré map; determine one or more geometric properties of the alpha shape object; and determine an estimated value for presence, non-presence, localization, and/or severity of a disease or condition based on the determined one or more geometric properties, wherein the disease state includes presence of coronary artery disease (e.g., significant coronary artery disease) or elevated/abnormal left ventricular end-diastolic pressure.

In some embodiments, the determined Poincaré map is generated by plotting photoplethysmographic signal peaks at a first time x−1 to a second time x in a first axis and at the second time x to a third time x+1 in a second axis.

In some embodiments, the system further includes a measurement system configured to acquire one or more photoplethysmographic signals.

In some embodiments, the system further includes a measurement system configured to acquire one or more cardiac signals.

In some embodiments, the system further includes a first measurement system configured to acquire one or more photoplethysmographic signals; and a second measurement system configured to acquire one or more cardiac signals.

In another aspect, a system is disclosed comprising a processor; and a memory having instructions stored therein, wherein execution of the instructions by the processor, cause the processor to perform any of the above methods.

In another aspect, a computer readable medium is disclosed having instructions stored therein, wherein execution of the instructions by a processor, cause the processor to perform any of the above method

BRIEF DESCRIPTION OF THE DRAWINGS

The accompanying drawings, which are incorporated in and constitute a part of this specification, illustrate embodiments and together with the description, serve to explain the principles of the methods and systems.

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIG. 4 shows experimental results from a study that indicates clinical predictive value of certain dynamical features extracted from photoplethysmographic signal(s) (red photoplethysmographic signals and infrared photoplethysmographic signals) that indicate the presence and non-presence of a disease or abnormal condition, or an indicator of one, in accordance with an illustrative embodiment.

FIG. 5 shows experimental results from a study that indicates clinical predictive value of certain dynamical features extracted cardiac signals that indicates the presence and non-presence of a disease or abnormal condition, or an indicator of one, in accordance with an illustrative embodiment.

FIG. 16 shows experimental results from a study that indicates clinical predictive value of certain dynamical features extracted from generated Poincaré maps of photoplethysmographic signal(s) (red photoplethysmographic signals and/or infrared photoplethysmographic signals) that indicates the presence and non-presence of a disease or abnormal condition, or an indicator of one, in accordance with an illustrative embodiment.

DETAILED SPECIFICATION

Figure 1:
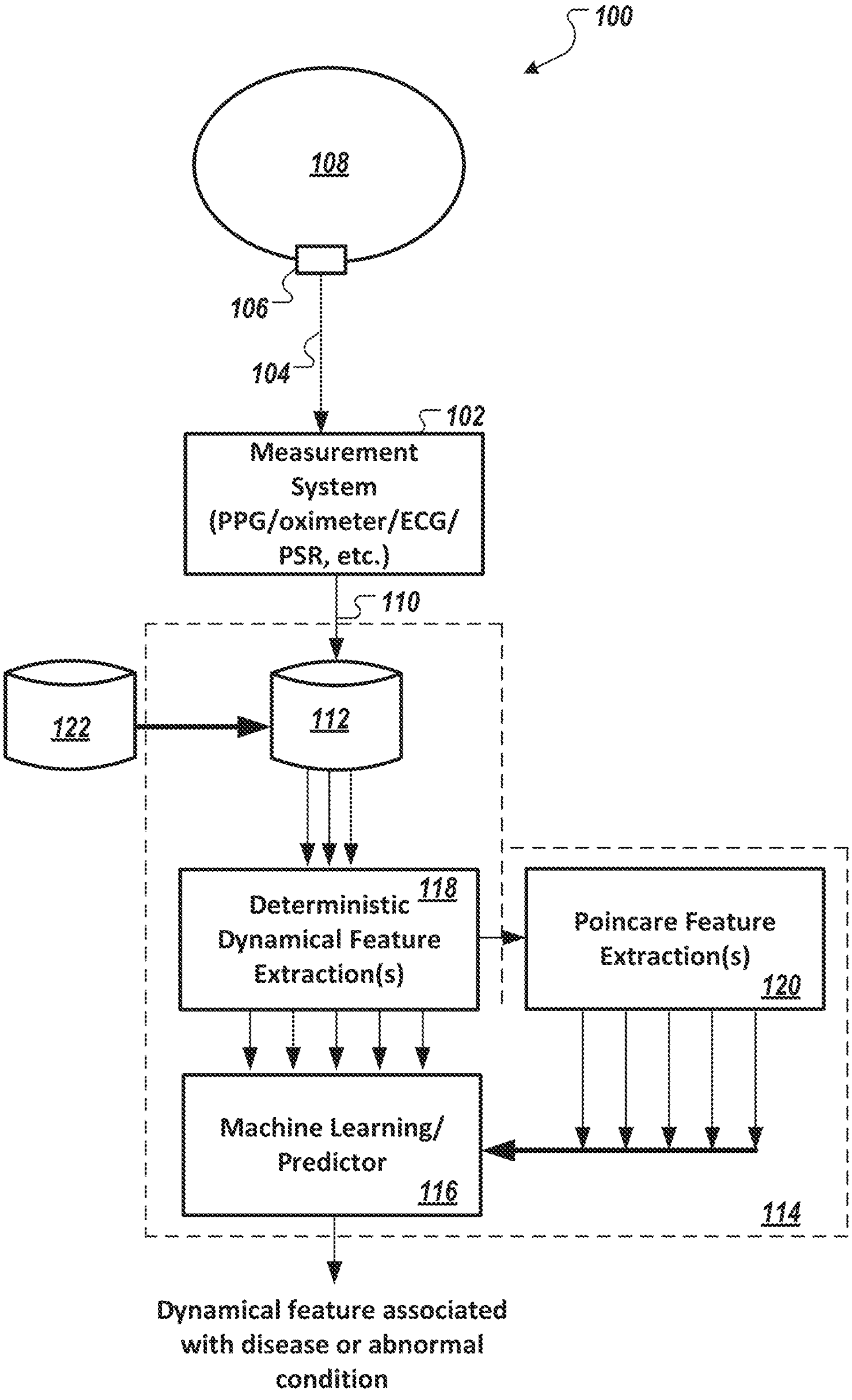
FIG. 1 is a diagram of an example system configured to non-invasively assess dynamical properties of a physiological system to predict and/or estimate presence, non-presence, localization (where applicable), and/or severity of a disease or condition, or an indicator of one, in such physiological system, in accordance with an illustrative embodiment.

Each and every feature described herein, and each and every combination of two or more of such features, is included within the scope of the present invention provided that the features included in such a combination are not mutually inconsistent.

While the present disclosure is directed to the beneficial assessment of biophysical signals, e.g., raw or pre-processed photoplethysmographic signals, cardiac signals, etc., in the diagnosis and treatment of cardiac-related pathologies and conditions, such assessment can be applied to the diagnosis and treatment (including, surgical, minimally invasive, and/or pharmacologic treatment) of any pathologies or conditions in which a biophysical signal is involved in any relevant system of a living body. In the cardiac (or cardiovascular) context, the assessment can be applied to the diagnosis and treatment of coronary artery disease (CAD) and diseases and/or conditions associated with an elevated or abnormal left ventricular end-diastolic pressure (LVEDP). The assessment can be applied for the diagnosis and treatment of any number of therapies, alone or in combination, such as the placement of a stent in a coronary artery, performance of an atherectomy, angioplasty, prescription of drug therapy, and/or the prescription of exercise, nutritional and other lifestyle changes, etc. Other cardiac-related pathologies or conditions that may be diagnosed include, e.g., arrhythmia, congestive heart failure, valve failure, pulmonary hypertension (e.g., pulmonary arterial hypertension, pulmonary hypertension due to left heart disease, pulmonary hypertension due to lung disease, pulmonary hypertension due to chronic blood clots, and pulmonary hypertension due to other disease such as blood or other disorders), as well as other cardiac-related pathologies, conditions and/or diseases. In some embodiments, the assessment may be applied to neurological-related pathologies and conditions. Non-limiting examples of neurological-related diseases, pathologies or conditions that may be diagnosed include, e.g., epilepsy, schizophrenia, Parkinson's Disease, Alzheimer's Disease (and all other forms of dementia), autism spectrum (including Asperger syndrome), attention deficit hyperactivity disorder, Huntington's Disease, muscular dystrophy, depression, bipolar disorder, brain/spinal cord tumors (malignant and benign), movement disorders, cognitive impairment, speech impairment, various psychoses, brain/spinal cord/nerve injury, chronic traumatic encephalopathy, cluster headaches, migraine headaches, neuropathy (in its various forms, including peripheral neuropathy), phantom limb/pain, chronic fatigue syndrome, acute and/or chronic pain (including back pain, failed back surgery syndrome, etc.), dyskinesia, anxiety disorders, conditions caused by infections or foreign agents (e.g., Lyme disease, encephalitis, rabies), narcolepsy and other sleep disorders, post-traumatic stress disorder, neurological conditions/effects related to stroke, aneurysms, hemorrhagic injury, etc., tinnitus and other hearing-related diseases/conditions and vision-related diseases/conditions.

Some references, which may include various patents, patent applications, and publications, are cited in a reference list and discussed in the disclosure provided herein. The citation and/or discussion of such references is provided merely to clarify the description of the disclosed technology and is not an admission that any such reference is "prior art" to any aspects of the disclosed technology described herein. In terms of notation, "[n]" corresponds to the nth reference in the list. For example, [36] refers to the 36th reference in the list, namely F. Pedregosa, G. Varoquaux, A. Gramfort, V. Michel, B. Thirion, O. Grisel, M. Blondel, P. Prettenhofer, R. Weiss, V. Dubourg, et al., "Scikit-learn: Machine learning in python," Journal of machine learning research 12, 2825-2830 (October 2011). All references cited and discussed in this specification are incorporated herein by reference in their entireties and to the same extent as if each reference was individually incorporated by reference.

Example System

FIG. 1 is a diagram of an example system 100 configured to non-invasively assess dynamical properties of a physiological system to predict and/or estimate (e.g., determine) presence, non-presence, localization (where applicable), and/or severity of a disease or condition, or an indicator of one, in such physiological system, in accordance with an illustrative embodiment. Indeed, as used herein, the term "predicting" refers to forecasting a future event (e.g., potential development of a disease or condition), while the term "estimating" can refer to a quantification of some metric based on available information, e.g., for the presence, non-presence, localization (where applicable), and/or severity of a disease or condition, or an indicator of one. The operations of predicting and estimating can be generally referred to as determining.

As noted herein, "physiological systems" can refer to the cardiovascular system, the pulmonary system, the renal system, the nervous system, and other functional systems and subsystems of the body. In the context of the cardiovascular system, the system 100 facilitates the investigation of complex, nonlinear dynamical properties of the heart over many heart cycles.

In FIG. 1, non-invasive measurement system 102 (shown as "Measurement System" 102) acquires one or more biophysical signals 104 via measurement probes 106 from a subject 108 to produce a biophysical-signal data set 110.

Figure 1A:
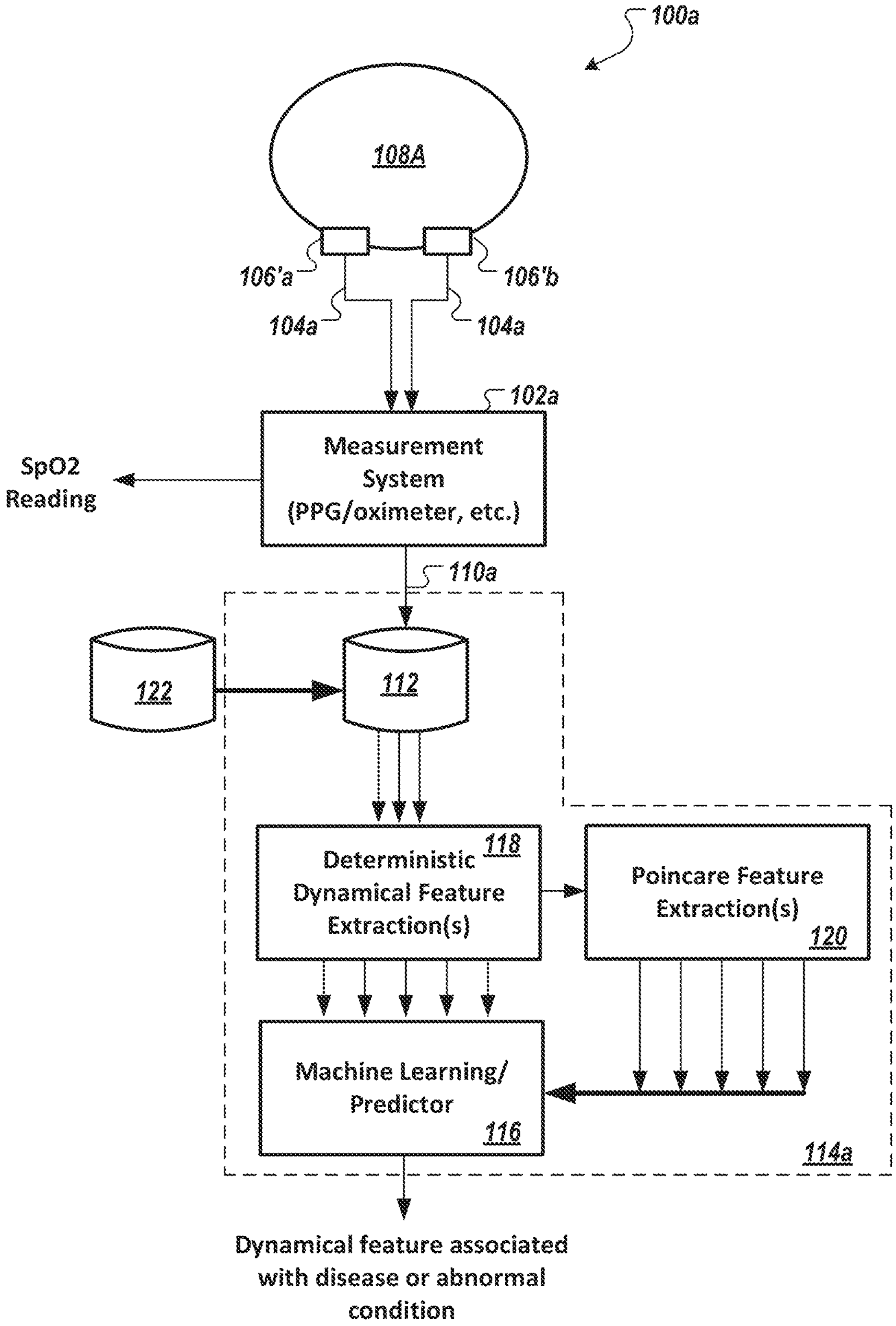
FIG. 1A is a diagram of another example system configured to non-invasively assess dynamical properties of photoplethysmographic signal(s) to predict and/or estimate presence, non-presence, localization (where applicable), and/or severity of a disease or condition, or an indicator of one, in a physiological system, in accordance with an illustrative embodiment.

The acquired biophysical signals 104, in some embodiments, include one or more photoplethysmographic signal(s) associated with measured changes in light absorption of oxygenated and/or deoxygenated hemoglobin (e.g., as shown in FIG. 1A).

Figure 1B:
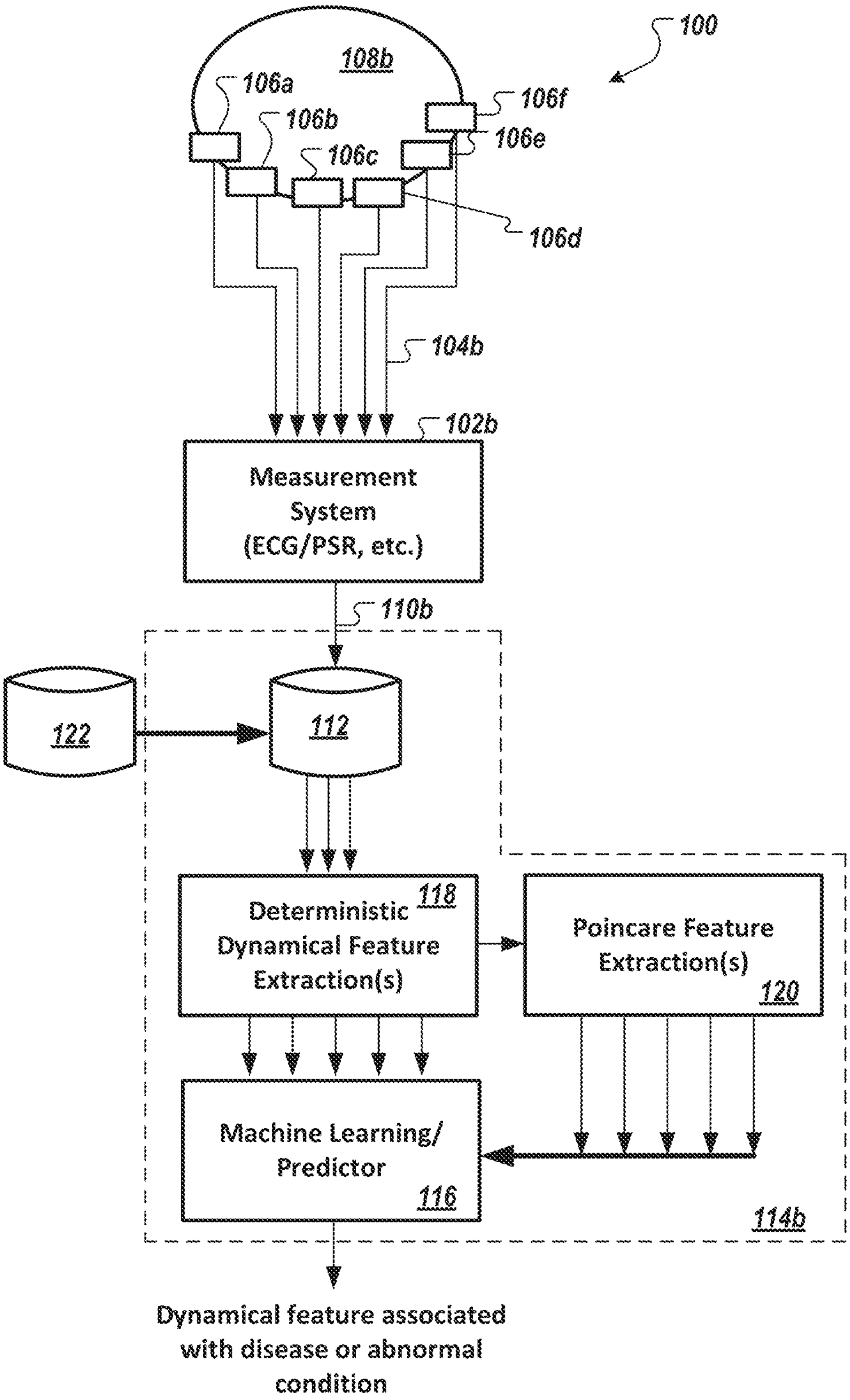
FIG. 1B is a diagram of an example system configured to non-invasively assess dynamical properties of cardiac signal(s) to predict and/or estimate presence, non-presence, localization (where applicable), and/or severity of a disease or condition, or an indicator of one, in a physiological system, in accordance with an illustrative embodiment.

In other embodiments, the acquired biophysical signals 104 include one or more cardiac signals associated with a biopotential measurement of the body (e.g., as shown in FIG. 1B). As used herein, the term "cardiac signal" refers to one or more signals associated with the structure, function and/or activity of the cardiovascular system—including aspects of that signal's electrical/electrochemical conduction—that, e.g., cause contraction of the myocardium. A cardiac signal may include, in some embodiments, electrocardiographic signals such as, e.g., those acquired via an electrocardiogram (ECG) or other modalities.

Referring still to FIG. 1, non-invasive measurement system 102 is configured to transmit, e.g., over a communication system and/or network, or over direct connection, the acquired biophysical-signal data set 110, or a data set derived or processed therefrom, to a repository 112 (e.g., a storage area network) (not shown) that is accessible to a non-invasive biophysical-signal assessment system. The non-invasive biophysical-signal assessment system 114 (shown as analytic engine 114) is configured to analyze dynamical properties of the acquired biophysical signal 104.

In some embodiments, analytic engine 114 includes a machine learning module 116 configured to assess a set of features determined via one or more feature extraction modules (e.g. 118, 120) from the acquired biophysical signal(s) to determine features of clinical significance. Once the features have been extracted from the photoplethysmographic signal(s) or cardiac signal(s), then any type of machine learning can be used. Examples of embodiments of machine learning module 116 is configured to implement, but not limited to, decision trees, random forests, SVMs, neural networks, linear models, Gaussian processes, nearest neighbor, SVMs, Naïve Bayes. In some embodiment, machine learning module 116 may be implemented, e.g., as described in U.S. patent application Ser. No. 15/653,433, entitled "Discovering Novel Features to Use in Machine Learning Techniques, such as Machine Learning Techniques for Diagnosing Medical Conditions"; and U.S. patent application Ser. No. 15/653,431, entitled "Discovering Genomes to Use in Machine Learning Techniques"; each of which are incorporated by reference herein in its entirety. The photoplethysmographic signal(s) may be combined with other acquired photoplethysmographic signal(s) to be used in a training data set or validation data set for the machine learning module 116 in the evaluation of a set of assessed dynamical features. The photoplethysmographic signal(s) may have an associated label 122 for a given disease state or abnormal condition. If determined to be of clinical significance, an assessed dynamical features (e.g., from 118 or 120) may be subsequently used as a predictor for the given disease or abnormal condition, or an indicator of one.

In some embodiments, analytic engine 114 includes a pre-processing module, e.g., configured to normalize and/or remove baseline wander from the acquired biophysical signal(s).

Photoplethysmographic Signal and Acquisition System

FIG. 1A is a diagram of an example system 100 (shown as 100*a*) configured to non-invasively assess dynamical properties of acquired photoplethysmographic signal(s) 104*a* to predict and/or estimate (e.g., determine) presence, non-presence, localization (where applicable), and/or severity of a disease or condition, or an indicator of one, in such physiological system, in accordance with an illustrative embodiment.

Photoplethysmographic signal(s) can include information relating to the complex interaction between the cardiac and respiratory/pulmonary systems. In some embodiments, photoplethysmographic signal(s) is acquired by a photoplethysmogram.

The photoplethysmogram is generally understood to include a noninvasive circulatory biophysical signal related to the pulsatile volume of blood in tissue. Pulse oximeters generate a type of photoplethysmogram that can be used to detect blood volume changes in the microvascular bed of tissue. A photoplethysmogram, in some embodiments, illuminates the skin and measures changes in light absorption using at least two different light wavelengths. Pulse oximeters are commonly worn on the finger (although they can be used on other regions of the body) in outpatient, inpatient and trauma settings to measure the fractional oxygen saturation of hemoglobin in the blood (known as "$SpO_2$"). However, the raw photoplethysmogram is less commonly displayed or further analyzed. Aspects of photoplethysmography are described in Reisner et al., "Utility of the Photoplethysmogram in Circulatory Monitoring" Anesthesiology 5 2008, Vol. 108, 950-958, the entirety of which is hereby incorporated herein by reference.

In FIG. 1A, non-invasive measurement system 102 (shown as "Measurement System" 102*a*) is configured to acquire one or more photoplethysmographic signals 104 (shown as 104*a*) via measurement probes 106 (shown as probes 106'*a*, 106'*b*) from a subject 108 (e.g., at a finger of a patient; shown as 108*a*) to produce a biophysical-signal data set 110 (shown as 110*a*). The acquired photoplethysmographic signal(s) 104*a*, in some embodiments, are associated with measured changes in light absorption by oxygenated and/or deoxygenated hemoglobin.

In some embodiments, measurement system 102*a* comprises custom or dedicated equipment or circuitries (including off-the-shelf devices) that are configured to acquire such signal waveforms for the purpose of diagnosing disease or abnormal conditions. In other embodiments, measurement system 102*a* comprises pulse oximeter or optical photoplethysmographic device that can output acquired raw signals for analysis. Indeed, in some embodiments, the acquired waveform 104*a* may be analyzed to calculate the level of oxygen saturation of the blood shown in FIG. 1A as "$SpO_2$ reading". For the exemplified analysis application however, only the waveform is processed and utilized.

Referring still to FIG. 1A, non-invasive measurement system 102*a* is configured to transmit, e.g., over a communication system and/or network, or over direct connection, the acquired photoplethysmographic-signal data set 110*a*, or a data set derived or processed therefrom, to the repository 112 (e.g., a storage area network) that is accessible to a non-invasive biophysical-signal assessment system. The non-invasive biophysical-signal assessment system 114 (shown as analytic engine 114*a*) is configured to analyze dynamical properties of the acquired photoplethysmographic signal(s).

Figure 2A:
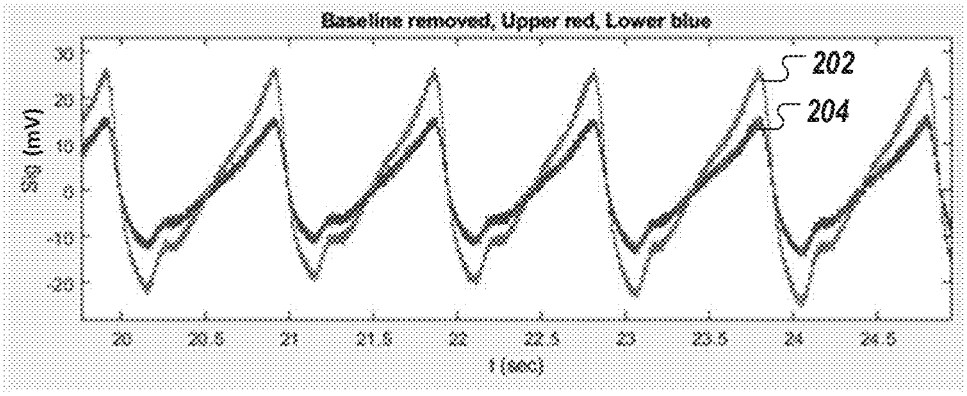
FIG. 2A shows examples photoplethysmographic signals (e.g., red photoplethysmographic signal and infrared photoplethysmographic signal) as example biophysical signals acquired via the measurement system of FIG. 1, in accordance with an illustrative embodiment. The signals are shown with baseline wander and high-frequency noise removed.

FIG. 2A shows an example of photoplethysmographic signals 104*a* acquired via the measurement system 102 of FIG. 1 (e.g., 102*a* of FIG. 1A) in accordance with an illustrative embodiment. Specifically, FIG. 2A shows a signal waveform 202 associated with the absorption level of the red spectrum of light (e.g., having wavelength that spans over 660 nm) by the deoxygenated hemoglobin from a finger of a patient. FIG. 2A also shows a signal waveform 204 of the absorption level associated with the infrared spectrum light (e.g., having wavelength that spans over 940 nm) by the oxygenated hemoglobin from a finger of a patient. Other spectra may be acquired. In addition, measurements may be performed at other parts of the body. In FIG. 2A, the x-axis shows time (in seconds) and the y-axis shows the signal amplitude in millivolts (my).

Figure 2B:
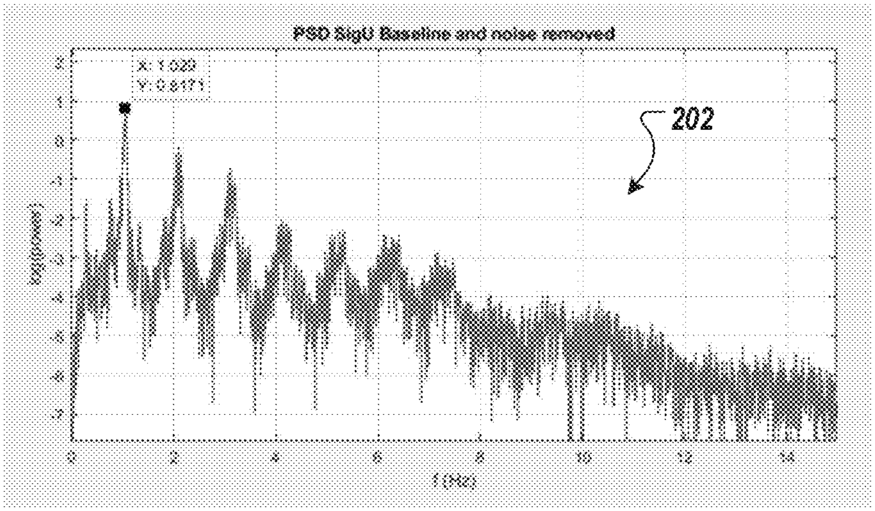
FIGS. 2B and 2C are frequency domain representations of the acquired photoplethysmographic signals FIG. 2A with high-frequency noise removed.
Figure 2C:
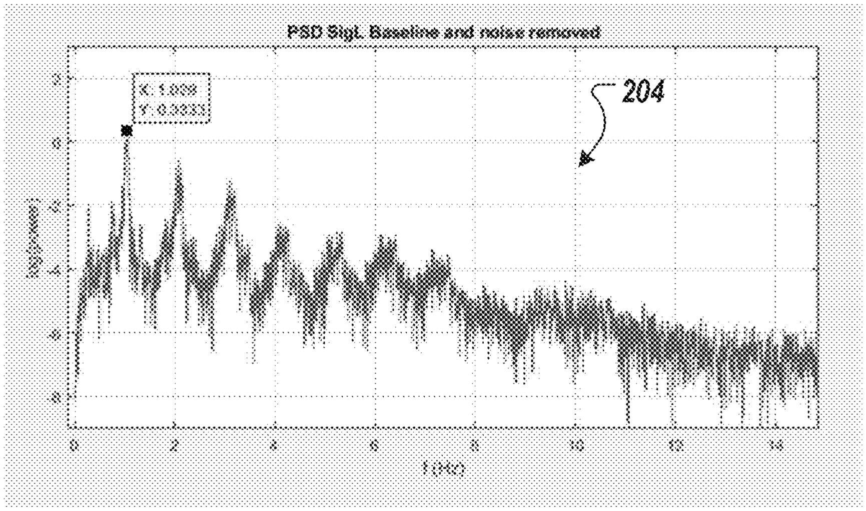

FIGS. 2B and 2C are power spectral density graphs showing frequency domain representations of the acquired photoplethysmographic signals FIG. 2A. In FIGS. 2B and 2C, the x-axis shows frequency (in Hertz) and the y-axis shows the power of the log of the signal.

In some embodiments, photo-absorption data of red and infrared channels are recorded at a rate of 500 samples per second. Other sampling rate may be used. The photoplethysmographic signals may be simultaneously acquired with the cardiac signals for each subject. In some embodiments, the acquisition between the two modalities has a jitter less than about 10 microseconds (μs). Jitter among the channels cardiac signals may be around 10 femtoseconds (fs), though other jitter may be tolerated.

Figure 2D:
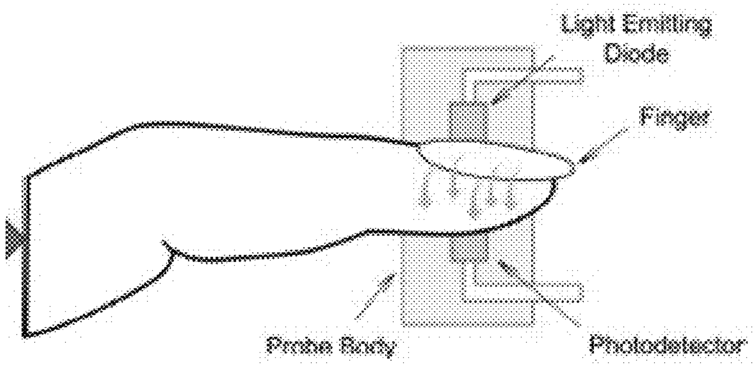
FIGS. 2D and 2E each shows an example sensor configuration to acquire photoplethysmographic signal(s) 104 in accordance with an illustrative embodiment.

FIG. 2D shows an example sensor configuration to acquire photoplethysmographic signal(s) 104*a* in accordance with an illustrative embodiment. In FIG. 2D, the system includes a light source (e.g., a red LED and an infrared LED) and a phototransistor (e.g., red detector and infrared detector); the phototransistor is distally located from the light source.

Figure 2E:
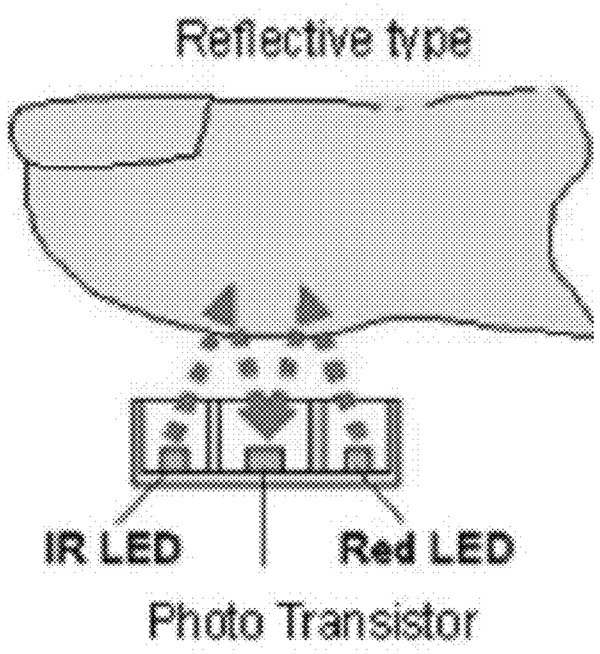

FIG. 2E shows another example sensor configuration to acquire photoplethysmographic signal(s) 104*a* in accordance with another illustrative embodiment. In FIG. 2D, the system also includes a light source (e.g., a red LED and an infrared LED) and a phototransistor (e.g., red detector and infrared detector); however, the phototransistor is proximally located to the light source to measure reflectance.

Photoplethysmographic signal(s) 104*a* may be considered as a measurements of the state of a dynamical system in the body, much like the cardiac signals. The behavior of the dynamical system may be influenced by the actions of the cardiac and respiratory systems. It is postulated that any aberration (due to a disease or abnormal condition) may manifest itself in the dynamics of photoplethysmographic signal(s) 104*a* via some interaction mechanism.

In some embodiments, the acquired photoplethysmographic signal(s) 104*a* are down-sampled to 250 Hz. Other frequency ranges may be used. In some embodiments, the acquired photoplethysmographic signal(s) 104*a* are processed to remove baseline wander and to filter for noise and main's frequencies.

Figure 2F:
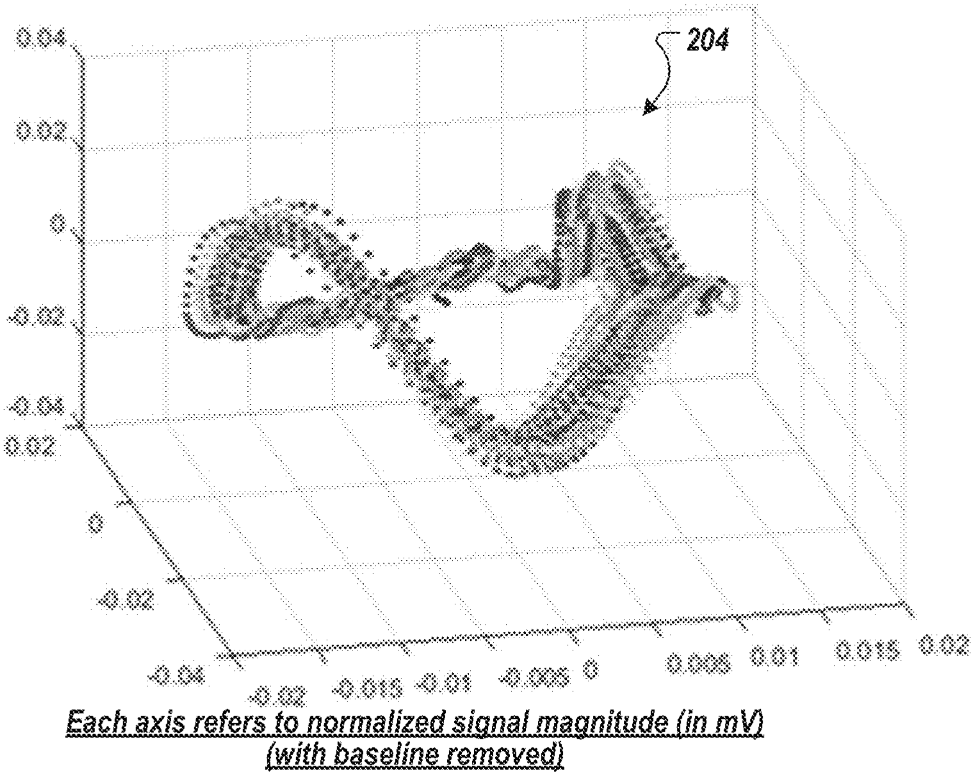
FIG. 2F shows a three-dimensional phase space plot of an acquired photoplethysmographic signal acquired via an infrared sensor.
Figure 2G:
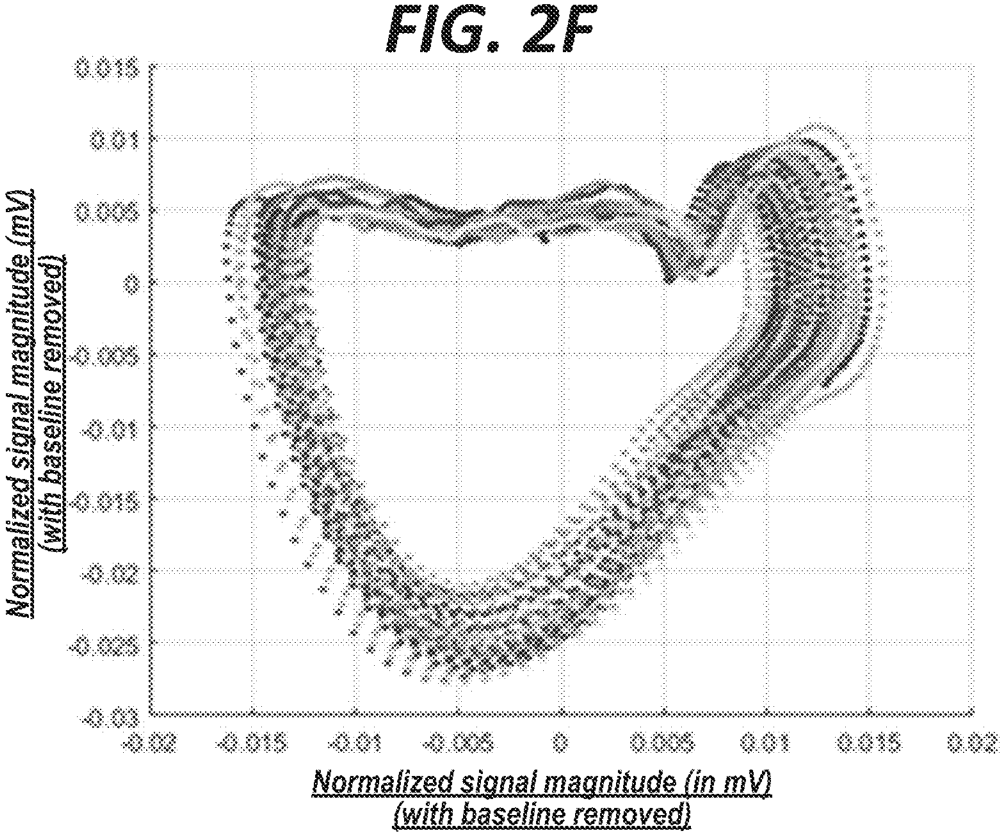
FIG. 2G shows a two-dimensional projection of the same data of FIG. 2F.

The acquired photoplethysmographic signal(s) 104*a* may be embedded in some higher dimensional space (e.g., phase space embedding) to reconstruct the manifold (phase space) the underlying dynamical system creates. A three-dimensional visualization and its two-dimensional projection are shown in FIGS. 2F and 2G (e.g., for a red photoplethysmographic signal 202). Specifically, FIG. 2F shows a three-dimensional phase space plot of an acquired photoplethysmographic signal 204 acquired via an infrared sensor. Axes are transformed voltage values (that is, the units on the vertical axis is still mV but normalized with the baseline wander removed to have a mean of about zero). Embedding is defined in Equation 2. The colors are selected to show coherent structures within this geometric object. The dynamical features of the photoplethysmographic-related measurements are calculated based on the embedding represented by the figure FIG. 2G shows a two-dimensional projection of the same.

Cardiac Signal and Acquisition System

FIG. 1B is a diagram of an example system 100 (shown as 100*b*) configured to non-invasively assess dynamical properties of a physiological system using acquired cardiac signal(s) 104*b* to predict and/or estimate (e.g., determine) presence, non-presence, localization (where applicable), and/or severity of a disease or condition, or an indicator of one, in such physiological system, in accordance with an illustrative embodiment.

In FIG. 1B, non-invasive measurement system 102 (shown as "Measurement System" 102*b*) acquires one or more cardiac signal(s) 104 (shown as 104*b*) via measurement probes 106 (shown as probes 106*a*-106*f*) from a subject 108 (e.g., at a chest and back area of a patient; shown as 108*b*) to produce a biophysical-signal data set 110 (shown as 110*b*).

In some embodiments, measurement system 102*b* is configured to acquire biophysical signals that may be based on the body's biopotential via bipotential sensing circuitries as biopotential biophysical signals.

In the cardiac and/or electrocardiography contexts, measurement system 102*b* is configured to capture cardiac-related biopotential or electrophysiological signals of a mammalian subject (such as a human) as a biopotential cardiac signal data set. In some embodiments, measurement system 102*b* is configured to acquire a wide-band cardiac phase gradient signals as a biopotential signal, a current signal, an impedance signal, a magnetic signal, an ultrasound or acoustic signal, and etc. The term "wide-band" in reference to an acquired signal, and its corresponding data set, refers to the signal having a frequency range that is substantially greater than the Nyquist sampling rate of the highest dominant frequency of a physiological system of interest. For cardiac signals, which typically has a dominant frequency components between about 0.5 Hz and about 80 Hz, the wide-band cardiac phase gradient signals or wide-band cardiac biophysical signals comprise cardiac frequency information at a frequency selected from the group consisting between about 0.1 Hz and 1 KHz, between about 0.1 Hz and about 2 KHz, between about 0.1 Hz and about 3 KHz, between about 0.1 Hz and about 4 KHz, between about 0.1 Hz and about 5 KHz, between about 0.1 Hz and about 6 KHz, between about 0.1 Hz and about 7 KHz, between about 0.1 Hz and about 8 KHz, between about 0.1 Hz and about 9 KHz, between about 0.1 Hz and about 10 KHz, and between about 0.1 Hz and greater than 10 KHz (e.g., 0.1 Hz to 50 KHz or 0.1 Hz to 500 KHz). In addition to capturing the dominant frequency components, the wide-band acquisition also facilitates capture of other frequencies of interest. Examples of such frequencies of interest can include QRS frequency profiles (which can have frequency ranges up to 250 Hz), among others. The term "phase gradient" in reference to an acquired signal, and corresponding data set, refers to the signal being acquired at different vantage points of the body to observe phase information for a set of distinct events/functions of the physiological system of interest. Following the signal acquisition, the term "phase gradient" refers to the preservation of phase information via use of non-distorting signal processing and pre-processing hardware, software, and techniques (e.g., phase-linear filters and signal-processing operators and/or algorithms).

In some embodiments, the cardiac signal data set 110*b* includes wide-band biopotential signals, e.g., acquired via a phase-space recorder, as described in U.S. Patent Publication No. 2017/0119272, entitled "Method and Apparatus for Wide-Band Phase Gradient Signal Acquisition," which is incorporated by reference herein in its entirety. In some embodiments, the cardiac signal data set includes bipolar wide-band biopotential signals, e.g., acquired via a phase-space recorder, as described in U.S. Patent Publication No. 2018/0249960, entitled "Method and Apparatus for Wide-Band Phase Gradient Signal Acquisition," which is incorporated by reference herein in its entirety. In other embodiments, the cardiac signal data set 110*b* includes one or more biopotential signals acquired from conventional electrocardiogram (ECG/EKG) equipment (e.g., Holter device, 12 lead ECG, etc.).

The phase space recorder as described in 2017/0119272, in some embodiments, is configured to concurrently acquire photoplethysmographic signals 104*a* along with cardiac signal 104*b*. Thus, in some embodiments, measurement system 102*b* is configured to acquire two types of biophysical signals.

Figure 3A:
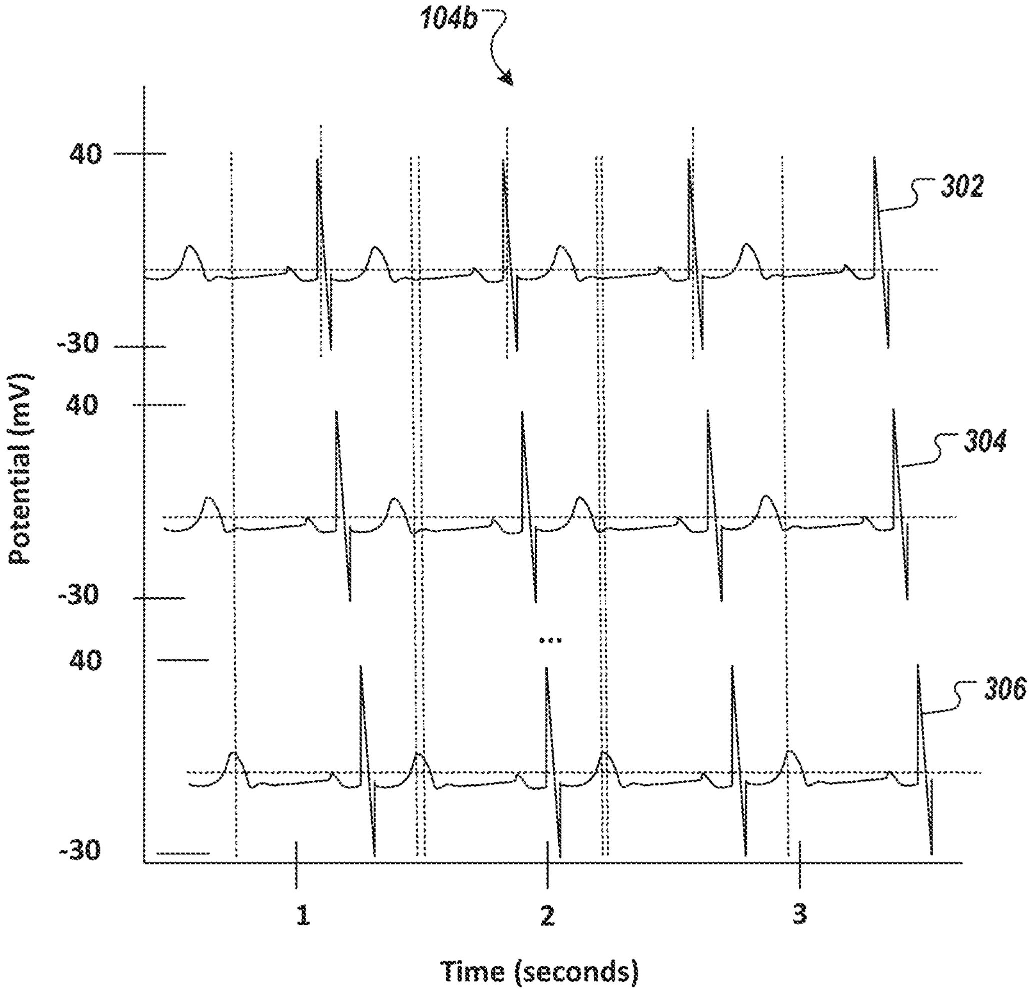
FIG. 3A shows example cardiac signals (e.g., biopotential signals) as example biophysical signals acquired via the measurement system of FIG. 1, in accordance with an illustrative embodiment. The signals are shown with baseline wander and high-frequency noise removed.

FIG. 3A shows example cardiac signals (e.g., biopotential signals) as example biophysical signals acquired via the measurement system of FIG. 1, in accordance with an illustrative embodiment. The signals are shown with baseline wander and high-frequency noise removed. In some embodiments, cardiac signals 104*b* are acquired using a phase space recorder device, e.g., as described in 2017/0119272. The signals 104*b* includes bipolar biopotential measurements acquired over three channels to provide three signals 302, 304, 306 (also referred to channel "x", channel "y", and channel "z"). In FIG. 3A, the x-axis shows time (in seconds) and the y-axis shows the signal amplitude in millivolts (my).

Figure 3B:
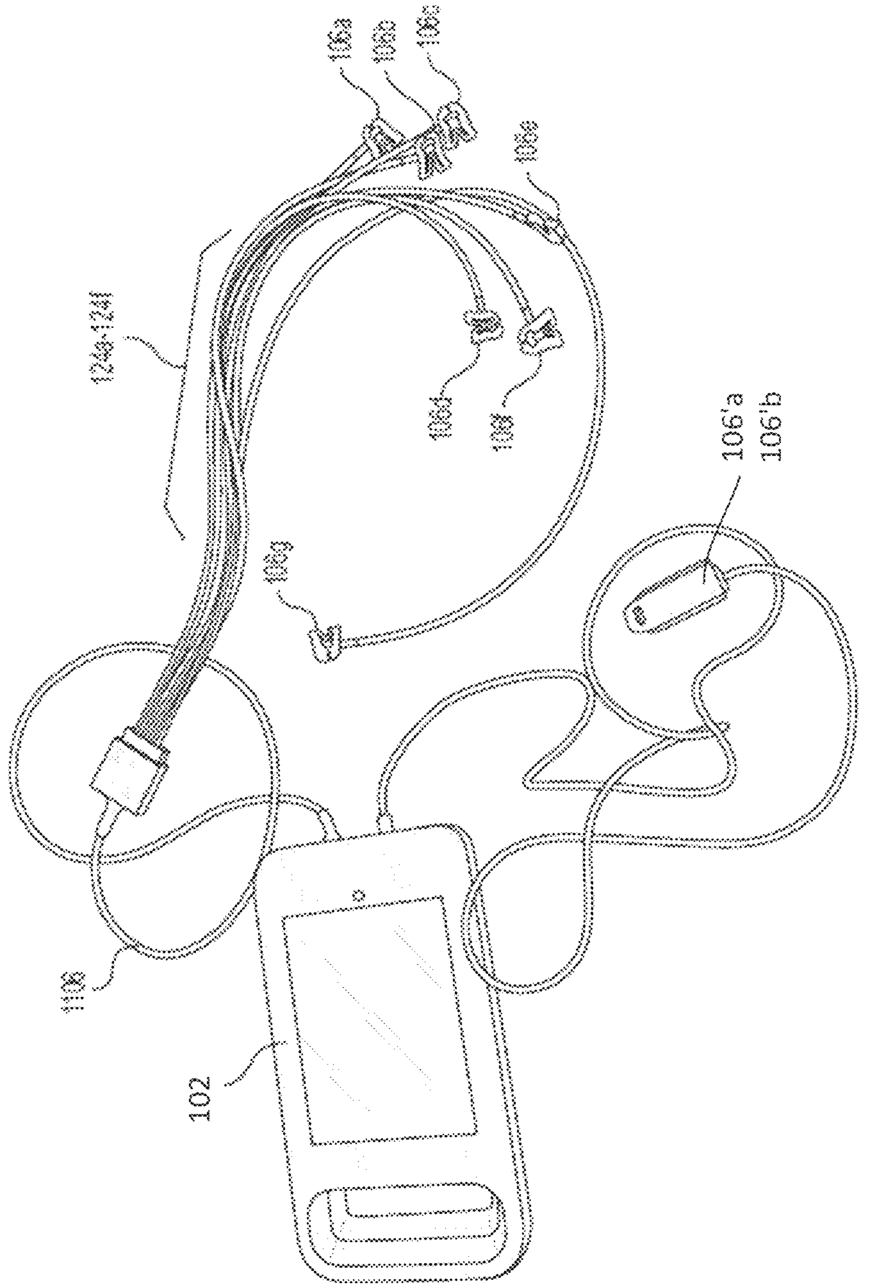
FIG. 3B is diagram of a measurement system configured to acquire the cardiac signals of FIG. 3A in accordance with an illustrative embodiment.

FIG. 3B is a diagram of a phase space recorder device, e.g., as described in U.S. Patent Publication No. 2017/0119272, configured to acquire cardiac signals 104*b*. The phase space recorder device is further configured to also acquire photoplethysmographic signals 104*a*.

Referring still to FIG. 1B, the non-invasive measurement system 102*b* is configured to transmit, e.g., over a communication system and/or network, or over direct connection, the acquired cardiac-signal data set 110*b*, or a data set derived or processed therefrom, to repository 112 (e.g., a storage area network) that is accessible to a non-invasive biophysical-signal assessment system. The non-invasive biophysical-signal assessment system 114 (shown as analytic engine 114) is configured to analyze dynamical properties of the acquired photoplethysmographic signal(s).

In the neurological context, the measurement system 102 is configured to capture neurological-related biopotential or electrophysiological signals of a mammalian subject (such as a human) as a neurological biophysical-signal data set. In some embodiments, measurement system 102 is configured to acquire wide-band neurological phase gradient signals as a biopotential signal, a current signal, an impedance signal, a magnetic signal, an ultrasound or acoustic signal, an optical signal, etc. An example of measurement system 102 is described in U.S. Patent Publication No. 2017/0119272 and in U.S. Patent Publication No. 2018/0249960, each of which is incorporated by reference herein in its entirety.

In some embodiments, measurement system 102 is configured to capture wide-band biopotential biophysical phase gradient signals as unfiltered mammalian electrophysiological signals such that the spectral component(s) of the signals are not altered. Indeed, in such embodiments, the wide-band biopotential biophysical phase gradient signals are captured, converted, and even analyzed without having been filtered (via, e.g., hardware circuitry and/or digital signal processing techniques, etc.) (e.g., prior to digitization) that otherwise can affect the phase linearity of the biophysical signal of interest. In some embodiments, the wide-band biopotential biophysical phase gradient signals are captured in microvolt or sub-microvolt resolutions that are at, below, or significantly below, the noise floor of conventional electrocardiographic, electroencephalographic, and other biophysical-signal acquisition instruments. In some embodiments, the wide-band biopotential biophysical signals are simultaneously sampled having a temporal skew or "lag" of less than about 1 microsecond, and in other embodiments, having a temporal skew or lag of not more than about 10 femtoseconds. Notably, the exemplified embodiments minimize non-linear distortions (e.g., those that can be introduced via certain filters) in the acquired wide-band phase gradient signal to not affect the information therein.

Figure 3C:
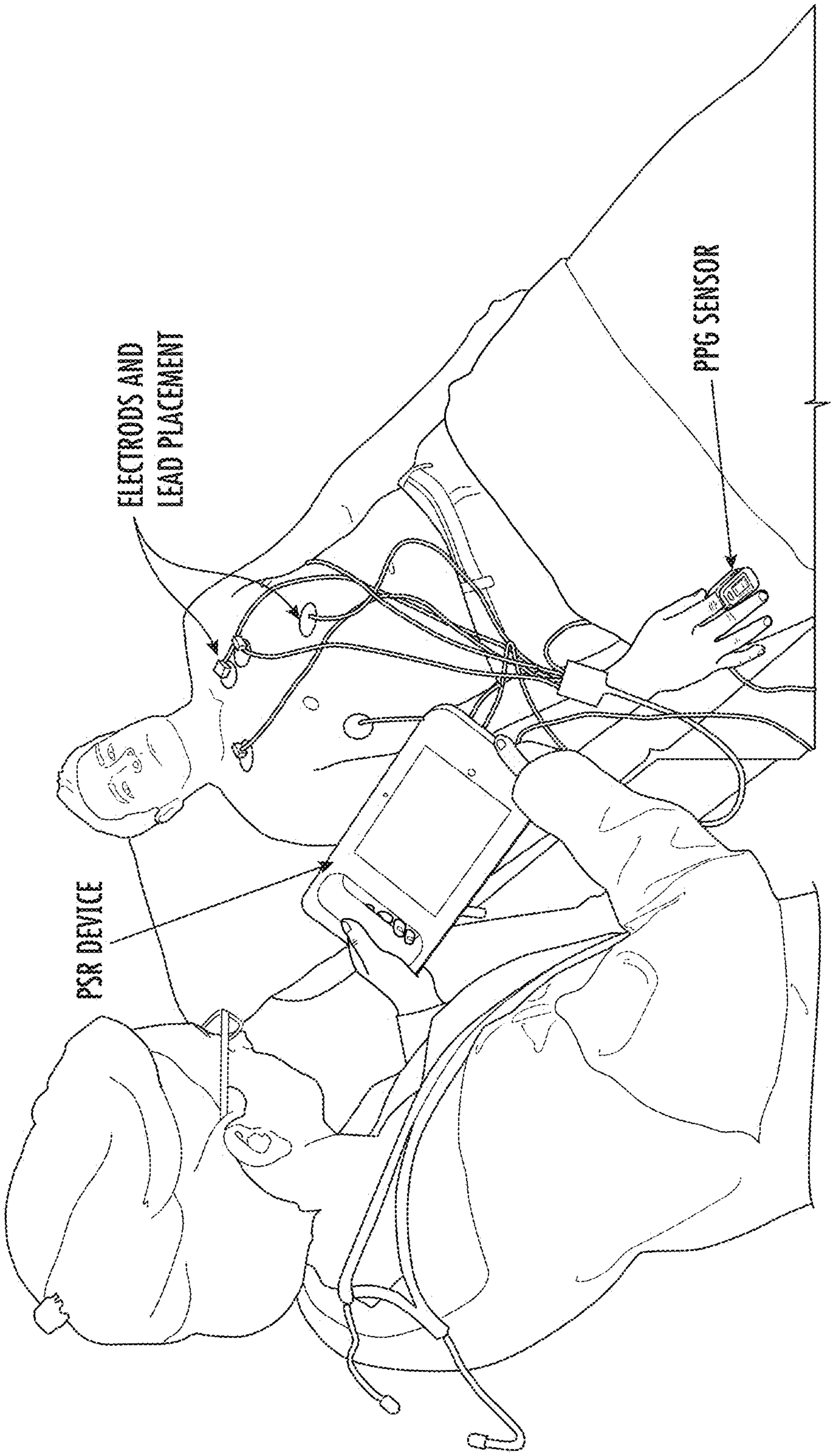
FIG. 3C shows an example placement of the measurement system of FIG. 3B on a patient in a clinical setting in accordance with an illustrative embodiment.
Figure 3D:
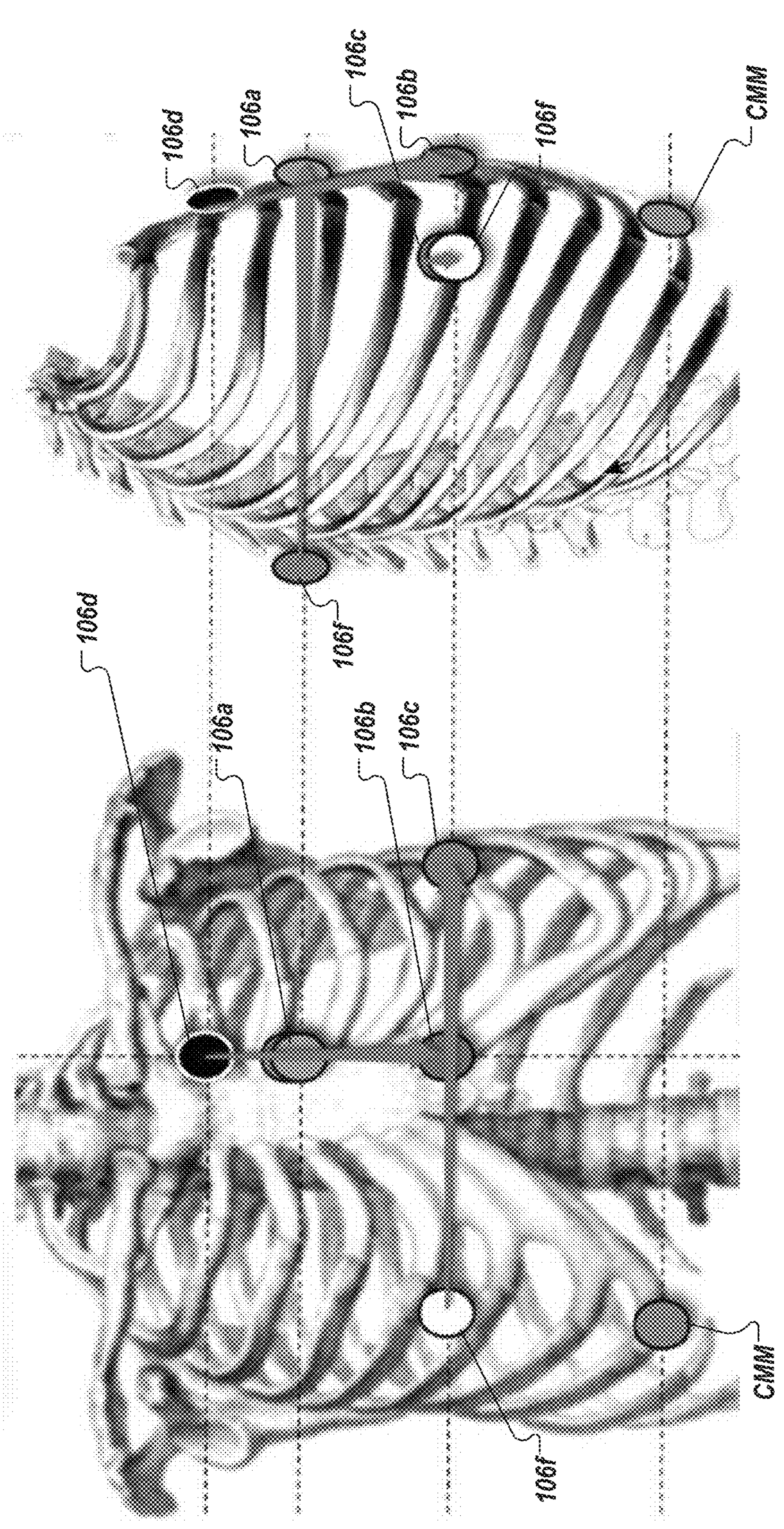
FIG. 3D is a diagram of an example placement of surface electrodes of the measurement system of FIG. 3B at the chest and back of a patient to acquire the cardiac signals of FIG. 3A in accordance with an illustrative embodiment.

FIG. 3C shows an example placement of the measurement system of FIG. 3B on a patient in a clinical setting in accordance with an illustrative embodiment. FIG. 3D is a diagram of an example placement of the surface electrodes 106*a*-106*g* at a patient to acquire the cardiac signals of FIG. 3A in accordance with an illustrative embodiment. Specifically, FIG. 3D shows example placement of the surface electrodes 106*a*-106*g* at the chest and back of a patient to acquire biopotential signals associated with wide-band cardiac phase gradient signals in accordance with an illustrative embodiment. In the left pane of FIG. 3D, surface electrodes 106*a*-106*g* are shown placed at the chest and back area of the patient. In the right pane of FIG. 3D, side view of placement of the surface electrodes 106*a*-106*g* is shown.

In the example configuration shown in FIG. 3D, surface electrodes 106*a*-106*g* are positioned on the patient's skin at i) a first location proximal to a right anterior axillary line corresponding to a 5th intercostal space; ii) a second location proximal to a left anterior axillary line corresponding to the 5th intercostal space; iii) a third location proximal to a left sternal border corresponding to a 1st intercostal space; iv) a fourth location proximal to the left sternal border below the sternum and lateral to the patient's xiphoid process; v) a fifth location proximal to the left sternal border corresponding to a 3rd intercostal space; vi) a sixth location proximal to the patient's back directly opposite of the fifth location and left of the patient's spine; and viii) a seventh location proximal to a right upper quadrant corresponding to a 2nd intercostal space along a left axillary line. A common lead (shown as "CMM") is also shown. Locations of individual surface electrodes may vary in other embodiments of the present disclosure as other electrode configurations may be useful.

Referring to FIG. 1, non-invasive measurement system 102 is configured with circuitry and computing hardware, software, firmware, middleware, etc. to acquire the cardiac signal and/or the photoplethysmographic signal to generate the biophysical-signal data set 110. In other embodiments, non-invasive measurement system 102 includes a first equipment (not shown) to acquire the cardiac signal and includes a second equipment (not shown) to acquire the photoplethysmographic signal.

Referring to FIG. 1, the dynamical feature extraction module 118, in some embodiments, is configured to evaluate one or more nonlinear dynamical properties, including for example, but not limited to Lyapunov exponent (LE), entropy (K2), and other statistical and geometrical characterization properties of the photoplethysmographic signal(s) 104.

Lyapunov exponent is a global measure that characterizes the strength of the exponential divergence [30]. For chaotic systems, the maximum Lyapunov exponent is a positive number which indicates that the system has less memory of the past. For a given dynamical system, as Lyapunov exponent value becomes larger, the time horizon over which the past information can be used to predict the future becomes shorter. Entropy (KS) (or Kolmogorov Sinai entropy K2 [31, 32]) represents the rate of change of entropy with time. Fractal dimension (D2) characterizes the topological property of an attractor in phase space and can be used to reveal more about the dynamics in combining the geometric information of the attractor (fractality) and how the dynamics evolve on it [33].

Nonlinear dynamics and chaos theory systematically can be used to explain the complexity of linear system systems and provides tools to quantitatively analyze their behavior [19]. Linear systems can generate responses which grow/decay exponentially or oscillate periodically or a combination thereof in which any irregular pattern in the response may be ascribed to irregularity or randomness in the inputs to these systems. Linear systems are a simplification of reality, and most dynamical systems whether natural or man-made are inherently nonlinear which can produce complex irregular behavior even without any source of randomness. These behaviors are often called deterministic chaos. Nonlinear dynamics and chaos tools have been used to explain various complex biological and physiological phenomena [20, 21, 22, 23]; for example, to classify atrial fibrillations [24] and to characterize heart rate variability [25], each of where is incorporated by reference here in its entirety.

In some embodiments, system 100 includes a healthcare provider portal to display, e.g., in a report, score or various outputs of the analytic engine 114 in predicting and/or estimating presence, non-presence, severity, and/or localization (where applicable) of a disease or abnormal condition, or an indicator of one. The physician or clinician portal, in some embodiments, is configured to access and retrieve reports from a repository (e.g., a storage area network). The physician or clinician portal and/or repository can be compliant with various privacy laws and regulations such as the U.S. Health Insurance Portability and Accountability act of 1996 (HIPAA). Further description of an example healthcare provider portal is provided in U.S. Pat. No. 10,292,596, entitled "Method and System for Visualization of Heart Tissue at Risk", which is incorporated by reference herein in its entirety. Although in certain embodiments, the portal is configured for presentation of patient medical information to healthcare professionals, in other embodiments, the healthcare provider portal can be made accessible to patients, researchers, academics, and/or other portal users.

Referring to FIG. 1, in some embodiments, analytical engine 114 includes a Poincaré feature extraction module 120 configured to evaluate geometric and topographic properties of a Poincaré map object generated from the photoplethysmographic signal(s) 104.

Experimental Results of Dynamical Analysis of Photoplethysmographic Signals

FIG. 4 shows experimental results from a study that indicates dynamical features extracted from photoplethysmographic signal(s) (red photoplethysmographic signals and infrared photoplethysmographic signals) has clinical predictive value in the assessment of a disease or abnormal condition, or an indicator of one, in accordance with an illustrative embodiment. Although the data set notes that prediction/estimation are with respect to certain population sets (e.g., based on gender) and disease or condition, or an indicator of one, the experimental results are merely stratified according to these criteria in the presented analysis. Indeed, the experimental results and the methods and systems discussed herein provides a basis to diagnose the presence or non-presence and/or severity and/or localization of diseases or conditions such as heart failure (HF) in general even when ejection fraction (EF) is preserved and without necessarily correlating it to an LVEDP level. In other words, the instant system and method may be used to make noninvasive diagnoses or determinations of the presence or non-presence and/or severity of various forms of heart failure (HF), as well as other diseases and/or conditions without LVEDP determinations/estimates. It is generally understood that LVEDP may be an indicator of disease but is in it itself not considered a disease state or condition.

In the study, a set of dynamical features of photoplethysmographic signal(s) were assessed, including those relating to correlation and mutual information, Lyapunov exponents, and fractal dimension, and entropy. Correlation may include auto correlation (e.g., auto correlation lags) and cross correlation to capture linear interactions. Mutual information may be used to find non-linear dependence. Lyapunov exponents may be used to measure level of chaoticity. Fractal dimensions is also referred to as "D2". Entropy may be used to assess rate of generating information on the fractal; also referred to as "K2".

In the study, candidate features were evaluated using t-test, mutual information, or AUC. T-tests were conducted against a null-hypothesis of normal LVEDP and null hypothesis of negative coronary artery disease. A t-test is a statistical test that can determine if there is a difference between two sample means from two populations with unknown variances. The output of the t-test is p-value in which a small p-value (typically ≤0.05) indicates strong evidence against the null hypothesis. The study used random sampling with replacement (bootstrapping) to generate test sets.

Mutual information operations were conducted to assessed dependence of elevated or abnormal LVEDP or significant coronary artery disease on certain feature set. Mutual information refers to a dimensionless quantity that is a measure of the mutual dependence between two random variables. MI is normalized by number of bins and the high and low MI are calculated as a high and a low of $$\frac{normMI}{\max(normMInoise)}.$$

A selected feature has a high that is greater than 1.0 and a low that is greater than 1.0.

A receiver operating characteristic curve, or ROC curve, is a graphical plot that illustrates the diagnostic ability of a binary classifier system as its discrimination threshold is varied. The ROC curve is created by plotting the true positive rate (TPR) against the false positive rate (FPR) at various threshold settings. Area-under-curve ROC (AUC-ROC) further considers the cost of an incorrect setting. The ROC, and AUC-ROC, value is significant if it is greater than 0.50.

Table 1 provides a description of each of the assessed dynamical extracted parameters of FIG. 4.

TABLE 1

| Parameter name | Description |
|---|---|
| SpAMILmin | Minimum auto mutual information lag of infrared photoplethysmographic signal |
| SpAMIUmin | Minimum auto mutual information lag of red photoplethysmographic signal |
| SpD2L | Correlation dimension "D2" of the infrared photoplethysmographic signal |
| SpD2U | Correlation dimension "D2" of the red photoplethysmographic signal |
| SpK2L | Entropy value "K2" of infrared photoplethysmographic signal |
| SpK2U | Entropy value "K2" of red photoplethysmographic signal |
| SpXCFLUZ2 | Cross-correlation between red and infrared photoplethysmographic signals at second zero crossing |

FIG. 4 shows that fractal dimension "D2" of a photoplethysmographic signal has potential clinical relevance in predicting/estimating the presence, non-presence, localization (where applicable), and/or severity of coronary artery disease and/or a disease or condition associated with elevated or abnormal LVEDP. The criteria for presence of CAD is defined as having greater than 70% stenosis by angiography or less than 0.80 fraction-flow by flow wire.

Specifically, FIG. 4 shows fractal dimension "D2" of the infrared photoplethysmographic signal (shown as "SpD2L") has a t-test p-value of 0.000000434 in predicting/estimating an elevated or abnormal LVEDP (which may indicate the presence, non-presence, and/or severity of a disease and/or condition). A small p-value (typically ≤0.05) indicates strong evidence against the null hypothesis (i.e., no presence of an elevated or abnormal LVEDP). Further, FIG. 4 shows that the fractal dimension ("D2") of the red photoplethysmographic signal (shown as "SpD2U") has a t-test p-value of 0.00000382 in predicting/estimating an elevated or abnormal LVED (which may indicate the presence, non-presence, and/or severity of a disease or condition) and a t-test p-value of 0.02 in predicting/estimating the presence, non-presence, localization (where applicable), and/or severity of coronary artery disease. Further, FIG. 4 also shows fractal dimension "D2" of the red photoplethysmographic signal (shown as "SpD2U") has a t-test p-value of 0.02 in predicting/estimating the presence, non-presence, localization (where applicable), and/or severity of coronary artery disease. A small p-value (typically ≤0.05) indicates strong evidence against the null hypothesis (i.e., no presence of an elevated or abnormal LVEDP or coronary artery disease).

In addition, FIG. 4 shows that mutual information of an acquired photoplethysmographic signal has potential clinical relevance in predicting/estimating the presence, non-presence, localization (where applicable), and/or severity of coronary artery disease. Specifically, FIG. 4 shows that minimum auto mutual information lag of the infrared photoplethysmographic signal (shown as "SpAMILmin") and minimum auto mutual information lag of the red photoplethysmographic signal (shown as "SpAMIUmin") has mutual information value of 1.288 and 1.016, respectively, in predicting/estimating the presence, non-presence, localization (where applicable), and/or severity of coronary artery disease. A time/index lag is calculated via auto mutual information of a signal with respect to the signal shifted with respect to itself to yield the minimum mutual information value. A mutual information value of greater than 1.0 has statistical significance.

In addition, FIG. 4 shows that entropy "K2" value of an acquired photoplethysmographic signal has potential clinical relevance in predicting/estimating the presence, non-presence, localization (where applicable), and/or severity of coronary artery disease and/or a disease or condition associated with an elevated or abnormal LVEDP. Specifically, FIG. 4 shows that entropy ("K2") of the red photoplethysmographic signal (shown as "SpK2U") and entropy ("K2") of the infrared photoplethysmographic signal (shown as "SpK2L") has a t-test p-value of 0.041 and 0.046, respectively, to predict/estimating the presence, non-presence, localization (where applicable), and/or severity of coronary artery disease and/or a disease or condition associated with an elevated or abnormal LVEDP in the certain population based on gender. A small p-value (typically ≤0.05) indicates strong evidence against the null hypothesis (i.e., no presence of significant coronary artery disease). A small p-value (typically ≤0.05) indicates strong evidence against the null hypothesis (i.e., no presence of CAD).

Experimental Results of Dynamical Analysis of Cardiac Signals

FIG. 5 shows experimental results from a study that indicates dynamical features extracted from cardiac signal(s) has clinical predictive value in the assessment of a disease or elevated or abnormal condition, or an indicator of one, in accordance with an illustrative embodiment. As noted above, although the data set notes that prediction/estimation are with respect to certain population sets (e.g., based on gender) and disease or condition, or an indicator of one (e.g., LVEDP or CAD), the experimental results are merely stratified according to these criteria in the presented analysis. Indeed, the experimental results and the methods and systems discussed herein provide a basis to diagnose the presence or non-presence and/or severity and/or localization (where applicable) of diseases or conditions, or an indicator of one such as heart failure (HF) in general even when ejection fraction (EF) is preserved and without necessarily correlating it to an LVEDP level. In other words, the instant system and method may be used to make noninvasive diagnoses or determinations of the presence or non-presence and/or severity and/or localization (where applicable) of various forms of heart failure (HF), as well as other diseases and/or conditions without LVEDP determinations/estimates.

In the study, a set of dynamical features of cardiac signal(s) were assessed, including those relating to correlation and mutual information, Lyapunov exponents, and fractal dimension and entropy. Correlation may include auto correlation (e.g., auto correlation lags) and cross correlation to capture linear interactions. Mutual information may be used to find non-linear dependence. Lyapunov exponents may be used to measure level of chaoticity. Fractal dimensions is also referred to as "D2". Entropy may be used to assess rate of generating information on the fractal; also referred to as "K2".

In the study, candidate features were evaluated using t-test, mutual information, or AUC. T-tests were conducted against a null-hypothesis of normal LVEDP and null hypothesis of negative coronary artery disease. A t-test is a statistical test that can determine if there is a difference between two sample means from two populations with unknown variances. The output of the t-test is a dimensionless quantity known as a p-value. A small p-value (typically ≤0.05) indicates strong evidence against the null hypothesis. The study used random sampling with replacement (bootstrapping) to generate test sets.

Mutual information techniques were conducted to assess any dependence of an elevated or abnormal LVEDP or significant coronary artery disease finding on certain feature sets. The term "mutual information" refers to an information theoretic measure of the mutual dependence between two random variables. MI is normalized by number of bins and the high and low MI are calculated as a high and a low of $$\frac{normMI}{\max(normMInoise)}.$$

A selected feature has a high that is greater than 1.0 and a low that is greater than 1.0.

Table 2 provides a description of each of the assessed dynamical extracted parameters of FIG. 5.

TABLE 2

| Feature Name | Feature Description |
|---|---|
| LEY | Lyapunov exponent of "Y" channel |
| D2X | Fractal Dimension (correlation dimension) D2 of "X" channel |
| D2Y | Fractal Dimension (correlation dimension) D2 of "Y" channel |
| K2X | KS entropy (K2) of "X" channel |
| K2Y | KS entropy (K2) of "Y" channel |
| K2Z | KS entropy (K2) of "Z" channel |
| AMIYmin | Minimum of auto mutual information of "Y" channel |
| AMIZmin | Minimum of auto mutual information of "Z" channel |
| XMIXYR | Cross Mutual Information Ratio: $I_{XY}/(I_{XX}*I_{YY})$ |
| XMIXZR | Cross Mutual Information Ratio: $I_{XZ}/(I_{XX}*I_{ZZ})$ |
| ACFXZ1 | First zero crossing of auto-correlation function of "X" channel |
| ACFYZ1 | First zero crossing of auto-correlation function of "Y" channel |
| ACFZZ1 | First zero crossing of auto-correlation function of "Z" channel |
| ACFXZ2 | Second zero crossing of auto-correlation function of "X" channel |
| ACFYZ2 | Second zero crossing of auto-correlation function of "Y" channel |
| ACFZZ2 | Second zero crossing of auto-correlation function of "Z" channel |
| XCFYZMax | Maximum cross correlation function between "Y" and "Z" channels |
| XCFXYMax | Maximum value of cross-correlation between "X" and "Y" channels |
| XCFXZMax | Maximum cross correlation function between "X" and "Z" channels |
| XCFXZ1 | Value of cross-correlation between "X" and "Z" channels at lag zero (no lag) |
| XCFXZZ1 | First zero crossing of cross-correlation between "X" and "Z" channels |
| XCFYZZ2 | Second zero crossing of cross-correlation between "Y" and "Z" channels |
| XCFYZDelay | Delay/lag between "Y" and "Z" channels in cross-correlation between "Y" and "Z" channels |

FIG. 5 shows that Lyapunov exponent of an acquired cardiac signal has potential clinical relevance in predicting/estimating an elevated or abnormal LVEDP (which may indicate the presence, non-presence, and/or severity of a disease and/or condition). Specifically, Lyapunov exponent value of channel "y" ("LEY") is shown to have mutual information value of 1.2 in predicting/estimating an elevated or abnormal LVEDP (which may indicate the presence, non-presence, and/or severity of a disease and/or condition). A mutual information value greater than 1.0 has significance.

In addition, FIG. 5 shows fractal dimension "D2" of acquired cardiac signals has potential clinical relevance in predicting/estimating the presence, non-presence, localization (where applicable), and/or severity of coronary artery disease. Specifically, FIG. 5 shows that fractal dimension "D2" of channel "x" (shown as "D2X") has an AUC of 0.53 in predicting/estimating the presence, non-presence, localization (where applicable), and/or severity of coronary artery disease. Further, FIG. 5 show that fractal dimension "D2" of channel "y" (shown as "D2Y") has an AUC of 0.52; t-test p-value of 0.002 in predicting/estimating the presence, non-presence, localization (where applicable), and/or severity of coronary artery disease. An AUC value greater than 0.5 has significance, and a p-value less than 0.05 has significance.

In addition, FIG. 5 shows entropy "K2" of acquired cardiac signals has potential clinical relevance in predicting/estimating an elevated or abnormal LVEDP (which may indicate the presence, non-presence, localization (where applicable), and/or severity of a disease and/or condition). Specifically, FIG. 5 shows that entropy "K2" of channel "x" (shown as "K2X") has mutual information value of 1.03 and an AUC value of 0.56 in predicting/estimating an elevated or abnormal LVEDP (which may indicate the presence, non-presence, and/or severity of a disease and/or condition). Further, FIG. 5 also shows entropy "K2" of channel "x" (shown as "K2X") has mutual information value of 1.32; t-test p-value of 0.0002; AUC of 0.53 in predicting/estimating the presence, non-presence, localization (where applicable), and/or severity of coronary artery disease. Further, FIG. 5 shows entropy "K2" channel "y" (shown as "K2Y") has t-test p-value of 0.0002; mutual information value of 1.05; and AUC of 0.53 in predicting/estimating the presence, non-presence, localization (where applicable), and/or severity of coronary artery disease. Further, FIG. 5 shows entropy "K2" channel "z (shown as "K2Z") has t-test p-value of 0.03; a mutual information value of 1.07; and an AUC value of 0.52 in predicting/estimating the presence, non-presence, localization (where applicable), and/or severity of coronary artery disease. An AUC value greater than 0.5 has significance; a p-value less than 0.05 has significance; a mutual information value greater than 1.0 has significance.

In addition, FIG. 5 shows auto correlation of acquired cardiac signals has potential clinical relevance in predicting/estimating an elevated or abnormal LVEDP (which may indicate the presence, non-presence, localization (where applicable), and/or severity of a disease and/or condition) and the presence, non-presence, localization (where applicable), and/or severity of coronary artery disease. Specifically, FIG. 5 shows that the minimum auto mutual information lag calculated of channel "y" (shown as "AMIYmin")—that is, the time/index lag to be shift between a calculated mutual information of a signal and itself to yield the minimum mutual information—has t-test p-value of 0.02 in predicting/estimating the presence, non-presence, localization (where applicable), and/or severity of coronary artery disease. Further, FIG. 5 shows that the minimum auto mutual information lag of channel "z" (shown as "AMIZmin") has t-test p-value of 0.03 in predicting/estimating the presence, non-presence, localization (where applicable), and/or severity of coronary artery disease. A p-value less than 0.05 has significance.

In addition, FIG. 5 shows auto correlation of cardiac signals has potential clinical relevance in predicting/estimating an elevated or abnormal LVEDP (which may indicate the presence, non-presence, localization (where applicable), and/or severity of a disease and/or condition). Specifically, FIG. 5 shows the first zero crossing of the auto correlation of channel "x" (shown as "ACFXZ1") has mutual information value of 1.05 in predicting/estimating the presence, non-presence, localization (where applicable), and/or severity of presence of coronary artery disease. Further, FIG. 5 also shows the first zero crossing of the auto correlation of channel "y" ("ACFYZ") and of channel "z" ("ACFZZ") has a t-test p-value of 0.0001 and 0.04, respectively, in predicting/estimating an elevated or abnormal LVEDP (which may indicate the presence, non-presence, and/or severity of a disease and/or condition). Further, FIG. 5 shows that the second zero crossing of the auto correlation of channel "x" ("ACFXZ2") has a t-test p-value of 0.03 and an AUC value of 0.51 in predicting/estimating the presence, non-presence, localization (where applicable), and/or severity of coronary artery disease. Further, FIG. 5 shows that the second zero crossing of the auto correlation of channel "y" ("ACFYZ2") has a t-test p-value of 0.001 in predicting/estimating an elevated or abnormal LVEDP (which may indicate the presence, non-presence, and/or severity of a disease and/or condition) and an AUC value of 0.51 in predicting/estimating the presence, non-presence, localization (where applicable), and/or severity of coronary artery disease. Further, FIG. 5 shows that the second zero crossing of the auto correlation of channel "z" ("ACFZZ2") has a t-test p-value of 0.002 in predicting/estimating an elevated or abnormal LVEDP (which may indicate the presence, non-presence, and/or severity of a disease and/or condition). An AUC value greater than 0.5 has significance; a p-value less than 0.05 has significance; a mutual information value greater than 1.0 has significance.

In addition, FIG. 5 shows cross-correlation between different channels of cardiac signals has potential clinical relevance in predicting/estimating an elevated or abnormal LVEDP (which may indicate the presence, non-presence, localization (where applicable), and/or severity of a disease and/or condition). Specifically, FIG. 5 shows that the maximum value of the cross-correlation between channel "y" and channel "z" of acquired cardiac signals (shown as "XCFYZ-Max") has mutual information of 1.03 in predicting/estimating an elevated or abnormal LVEDP (which may indicate the presence, non-presence, and/or severity of a disease and/or condition) and mutual information value of 1.13 in predicting/estimating the presence, non-presence, localization (where applicable), and/or severity of coronary artery disease. Further, FIG. 5 shows that the maximum value of the cross-correlation between channel "x" and channel "y" of the acquired cardiac signals (shown as "XCFXYMax") has t-test p-value of 0.0004 in predicting/estimating an elevated or abnormal LVEDP (which may indicate the presence, non-presence, and/or severity of a disease and/or condition). Further, FIG. 5 shows that the maximum value of the cross-correlation between channel "x" and channel "z" of acquired cardiac signals (shown as "XCFXZMax") has t-test p-value of 0.04 in predicting/estimating an elevated or abnormal LVEDP (which may indicate the presence, non-presence, and/or severity of a disease and/or condition) and a mutual information value of 1.03 in predicting/estimating the presence, non-presence, localization (where applicable), and/or severity of coronary artery disease. A p-value less than 0.05 has significance, and a mutual information value greater than 1.0 has significance.

In addition, FIG. 5 shows that the cross-correlation between channel "x" and channel "z" of the acquired cardiac signals (shown as "XCFXZ1") (at zero or no lag) has a t-test p-value of 0.002; a mutual information value of 1.59; an AUC value of 0.54 in predicting/estimating the presence, non-presence, localization (where applicable), and/or severity of coronary artery disease. Further, FIG. 5 shows that the first zero crossing of the cross-correlation between channel "x" and channel "z" of the acquired cardiac signals ("XCFXZZ1") has a t-test p-value of 0.0005; a mutual information value of 1.16; an AUC value of 0.56 in predicting/estimating the presence, non-presence, localization (where applicable), and/or severity of coronary artery disease. Further, FIG. 5 shows that the second zero crossing of the cross-correlation between channel "y" and channel "z" of the acquired cardiac signals (shown as "XCFYZZ2") has a t-test p-value of 0.004 in predicting/estimating an elevated or abnormal LVEDP (which may indicate the presence, non-presence, and/or severity of a disease and/or condition). Further, FIG. 5 shows that the delay/lag between channels "y" and "z" in the cross-correlation between channels "y" and "z" (shown as "XCFYZDelay") has a t-test p-value of 0.04 in predicting/estimating the presence, non-presence, localization (where applicable), and/or severity of coronary artery disease. An AUC value greater than 0.5 has significance; a p-value less than 0.05 has significance; a mutual information value greater than 1.0 has significance.

Example Method of Operation

FIGS. 6-10 and 11-15 each shows example dynamical feature analysis modules 118 of FIG. 1 (and FIGS. 1A and 1B) in accordance with an illustrative embodiment. The outputs of the modules of FIGS. 6-10 and 11-15 are merely illustrative. Embodiments may be implemented with some or all of the outputs shown. In some embodiments, additional outputs are generated.

Unlike systems which possess a mathematical model (equations), the dynamics of cardiovascular system is represented as some measurements and NDS characteristics are extracted from measured signals rather than through explicit governing equations. A measurement can be viewed as a projection of the true state of the system; for this reason, it is imperative to perform measurements that contain the most information about the true system. If the true states of the system are $x_1(t), \ldots x_n(t)$ a measurement s(t) may be represented by $$s = g(x_1, \ldots, x_n) \quad \text{(Equation 1)}$$

where g( . . . ) is the projection function. Now the task is to reconstruct from s(t) the true system or an approximation that is mathematically equivalent. This can be achieved by using the delay embedding phase space reconstruction. Further description may be found in Sauer et al., Embedology, Jour. Of Statistical Physics, Vol. 65: 3-4, pp 579-616 (November 1991).

In embedding theorem, it is stated that since in NDS the comprising components or states of the system are usually get coupled or interact with each other, just one measurement should contain information about all these effects. In addition, a topologically equivalent representative of the true system may be constructed form a single measurement.

One effective approach is the method of delay embedding. In this method, a vector space of size m is constructed as follows $$\vec{S_i} = [s_i, s_{i+\tau}, \ldots, s_{i+(m-1)\tau}], \vec{S_1} \in R^m \quad \text{(Equation 2)}$$

There are two important parameters m dimension of the phase space and T the delay. The dimension should be selected to be high enough so that the reconstructed manifold is unfolded adequately to represent the original dynamics. The delay should not be too small where the temporal correlation will become a dominant effect and not too large; the appropriate value should yield a well expanded manifold. These values may be fine-tuned for each application, here for cardiovascular signals.

In the study, m=24 and tau=40 (ms) corresponding to 10 index points in a 250-Hz signal. These values were obtained using a convergence analysis. In some embodiments, the techniques of NDS can be applied to characterize the system in phase space.

Lyapunov Exponent Feature(s)

Figure 6:
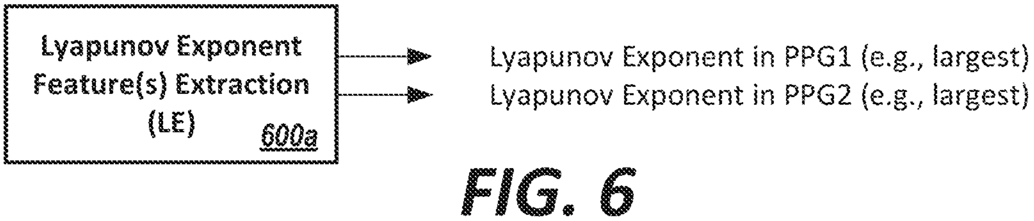
FIGS. 6 and 11 each shows a Lyapunov exponent feature extraction module in accordance with an illustrative embodiment.
Figure 11:
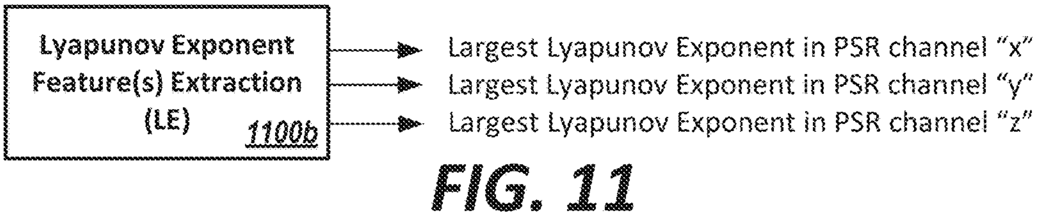

FIGS. 6 and 11 each shows a Lyapunov exponent feature extraction module 600. In FIG. 6, module 600 (shown as 600*a*) is configured to determine a largest Lyapunov exponent determined from photoplethysmographic signal(s) (e.g., the red photoplethysmographic signal and/or the infrared photoplethysmographic signal). In FIG. 11, module 600 (shown as 1100*b*) is configured to determine a largest Lyapunov exponent determined from cardiac signal (e.g., from channel "x" of the PSR device, channel "y" of the PSR device, and/or channel "z" of the PSR device).

Lyapunov exponent is the rate of exponential growth of the small initial perturbations. Basically, it represents how fast two nearby trajectories diverge:

$$\lambda = \lim_{t\to\infty} \frac{1}{t} \ln\left(\left|\frac{\delta(t)}{\delta_0}\right|\right) \quad \text{(Equation 3)}$$

where λ is the LE and δ(t) is the evolution of the initial perturbation $\delta_0$. In some embodiment, λ is calculated as the average over many points and for a finite time.

As shown in FIG. 6, module 600 may output the largest Lyapunov exponent value determined from each respective photoplethysmographic signal (e.g., of the red photoplethysmographic signal and/or of the infrared photoplethysmographic signal). In FIG. 11, module 1100*b* may output the largest Lyapunov exponent value determined from each respective cardiac signal (e.g., from acquired channel "x" of the PSR device, acquired channel "y" of the PSR device, and/or acquired channel "z" of the PSR device).

Table 3 shows example input arguments to the LE feature extraction module 600 (e.g., 600*a*, 1100*b*).

TABLE 3

| | |
|---|---|
| m | 24 |
| τ | 10 (index) (e.g., for a 250 Hz signal); 40 ms in general |
| Iterations | 100 |
| Steps | 10 (index) |
| NRef | 3000 |
| Max number of Neighbors | 30 |
| Jump | 10 (indx) |
| Search Algorithm | kd |
| "X" channel Radius | 0.1 |
| "Y" channel Radius | 0.15 |
| "Z" channel Radius | 0.15 |

Fractal Dimension Feature

Figure 7:
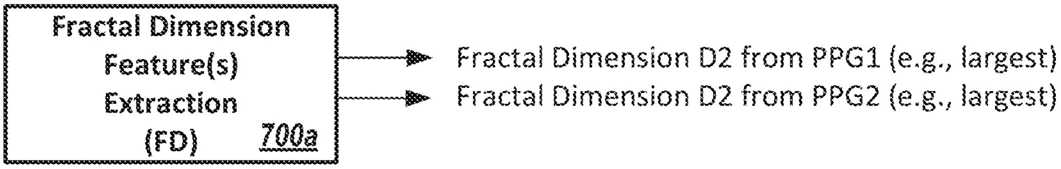
FIGS. 7 and 12 each shows a fractal dimension feature extraction module in accordance with an illustrative embodiment.
Figure 12:
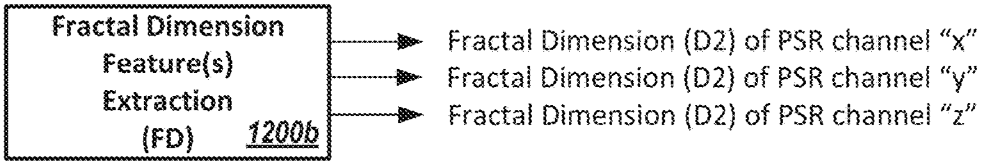

FIGS. 7 and 12 each shows a fractal dimension feature extraction module 700. In FIG. 7, module 700 (shown as 700*a*) is configured to determine fractal dimension values for the photoplethysmographic signal(s) (e.g., the red photoplethysmographic signal and the infrared photoplethysmographic signal), including, e.g., the fractal dimension ("D2") of the red photoplethysmographic signal and the infrared photoplethysmographic signal as described in relation to FIG. 4. In FIG. 12, module 700 (shown as 1200*b*) is configured to determine a fractal dimension "D2" determined from cardiac signal (e.g., from channel "x" of the PSR device, channel "y" of the PSR device, and/or channel "z" of the PSR device).

Fractals are geometric objects that have self-similar structure meaning that the same overall pattern is observed by magnification at various scales. One other aspect of fractal structure is their non-integer dimension. For example, the famous Lorenz attractor has a correlation dimension of 2.05 that is greater than a 2-dimensional manifold but less than a 3-dimensional volume. To find the fractal dimension a lot more data is required than for LE. Even that, finding the exact fractal dimension from measurement data is computationally intensive. To mitigate this issue a lower bound to the fractal dimension can be calculated through correlation dimension (D2).

The probability of the trajectory of the data in phase space (PS) being found within a ball U(ϵ) of radius e may be expressed as Equation 4:

$$p_\epsilon(s) = \int_{U(\epsilon)} d\mu(s) \quad \text{(Equation 1)}$$

In Equation, μ(s) is the probability density function. Then the generalized correlation integral of order q is defined as Equation 5.

$$C_q(\epsilon) = \int_s p_\epsilon(s)^{q-1} d\mu(s) \quad \text{(Equation 5)}$$

The integral of Equation 5 can be expanded to the following form in Equation 6.

$$C_q(\epsilon) = \int_s d\mu(s)\left[\int_{s'} \Theta(\epsilon - |s - s'|) d\mu(s')\right]^{q-1} \quad \text{(Equation 6)}$$

Per Equation 6, function Θ is the Heviside function that acts on two points of the trajectory s and s'. It is observed that the correlation sum varies according to the following power law.

$$C_q(\epsilon) \propto \epsilon^{(q-1)D_q} \quad \text{(Equation 7)}$$

From Equation 7, the correlation dimension of order q can be obtained as follows per Equation 8.

$$D_q = \lim_{\epsilon \to 0} \frac{1}{q-1} \frac{\ln C_q(\epsilon)}{\ln(\epsilon)} \quad \text{(Equation 8)}$$

Here, q=2 and is used to calculate $D_2$. The calculations can also be useful for estimating the rate of entropy change.

As shown in FIG. 7, module 700*a* may output the fractional dimension "D2" determined from each respective photoplethysmographic signal (e.g., of the red photoplethysmographic signal and/or of the infrared photoplethysmographic signal). In FIG. 12, module 1200*b* may output the fractal dimension "D2" determined from each respective cardiac signal (e.g., from acquired channel "x" of the PSR device, acquired channel "y" of the PSR device, and/or acquired channel "z" of the PSR device).

Table 4 shows example input argument to the fractal dimension feature extraction module 700 (e.g., 700*a*, 1200*b*).

TABLE 4

| | |
|---|---|
| M min | 23 |
| M max | 26 |
| Lag | 1 (indx) for 250 Hz down-sampled signal; 4 ms in general |
| Nref | 3000 |
| N min | 100 |
| Search Algorithm | Kd |
| Radius array | logspace(log10(0.12), log10(0.55), 20); |

Linear scaling regions may be calculated for "D2" and "K2". In addition, entropy curve for various embedding dimensions m may be calculated.

Entropy Feature

Figure 8:
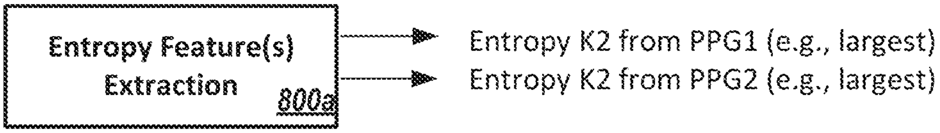
FIGS. 8 and 13 each shows an entropy feature extraction module in accordance with an illustrative embodiment.
Figure 13:
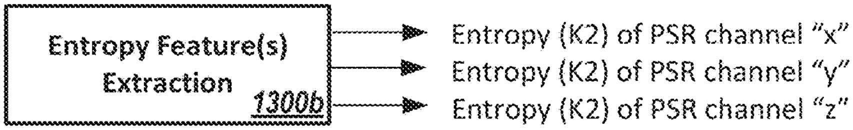

FIGS. 8 and 13 each shows an entropy feature extraction module 800. In FIG. 8, module 800 (shown as 800*a*) is configured to determine entropy values for the photoplethysmographic signal(s) (e.g., the red photoplethysmographic signal and/or the infrared photoplethysmographic signal). In FIG. 13, module 800 (shown as 1300*b*) is configured to determine entropy values for the cardiac signal (e.g., from channel "x" of the PSR device, channel "y" of the PSR device, and/or channel "z" of the PSR device).

Entropy can be understood as a measure of uncertainty or equivalently as information. If the probability of an event occurring is high, the uncertainty is little and information is high, and vice versa. The Shannon entropy is defined as Equation 9.

$$H_S = -\sum_i p_i \log(p_i) \quad \text{(Equation 9)}$$

Per Equation 9, entropy is defined as the sum over all possible states. For a chaotic system, the quantity grows as there are infinitely many states. Hence, the rate of change of entropy over the attractor is a more robust and informative measure of uncertainty. The rate of change of entropy is known as Kolmogorov-Sinai entropy per Equation 10.

$$K = -\lim_{\tau \to 0} \lim_{\epsilon \to 0} \lim_{m \to \infty} \frac{1}{m\tau} \Sigma_{i_1, \ldots, i_m} p(i_1, \ldots, i_m) \log[p(i_1, \ldots, i_m)] \quad \text{(Equation 10)}$$

Equation 10 is the average rate of change of entropy using block probability. That is, if the data in phase space is partitioned into m blocks, the probability states the joint probability if point 1 is in $i_1$ and 2 in $i_2$, etc. Calculating the quantity may be very computationally intensive; instead, a lower bound $k_2$ to this quantity may be calculated. The order-q Renyi entropy is defined as Equation 11.

$$K_q = -\lim_{\tau \to 0} \lim_{\epsilon \to 0} \lim_{m \to \infty} \frac{1}{m\tau} \frac{1}{q-1} \Sigma_{i_1, \ldots, i_m} [p(i_1, \ldots, i_m)]^q \quad \text{(Equation 11)}$$

It can be shown entropy rate (K2) can be calculated as follows per Equation 12.

$$K_{2,m}(\epsilon) = \frac{1}{\tau}\ln\frac{C(m, \epsilon)}{C(m+1, \epsilon)} \quad \text{(Equation 12)}$$

where $$\lim_{m\to\infty,\epsilon\to 0} K_{2,m}(\epsilon) \approx K_2 \quad \text{(Equation 13)}$$

The $K_2$ entropy rate may be a good approximation to a lower bound to K.

As shown in FIG. 8, module 800*a* may output the largest entropy value "K2" determined from each respective photoplethysmographic signal (e.g., of the red photoplethysmographic signal and/or of the infrared photoplethysmographic signal). In FIG. 13, module 1300*b* may output the largest entropy value "K2" determined from each respective cardiac signal (e.g., from acquired channel "x" of the PSR device, acquired channel "y" of the PSR device, and/or acquired channel "z" of the PSR device).

Table 5 shows example input parameters for the entropy feature extraction module 800 (e.g., 800*a*, 1300*b*). The parameters are suitable for suitable for 250 Hz signals.

TABLE 5

| | |
|---|---|
| M min | 23 |
| M max | 26 |
| Lag | 1 (indx) for 250 Hz down-sampled signal; 4 ms in general |
| Nref | 3000 |
| N min | 100 |
| Search Algorithm | Kd |
| Radius array | logspace(log10(0.12), log10(0.55), 20); |

Though Nref values of 2000 or 3000 may be used; other values may be used to reduce computational cost.

Mutual Information

Figure 9:
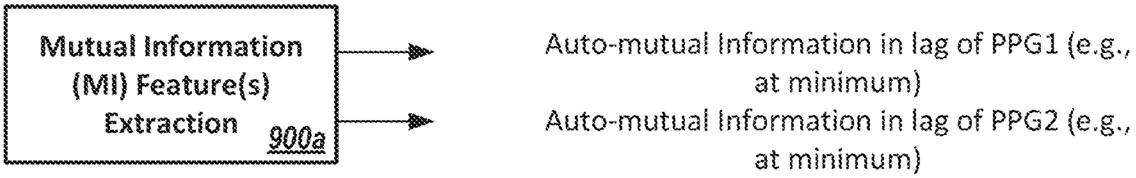
FIGS. 9 and 14 each shows a mutual information (MI) feature extraction module in accordance with an illustrative embodiment.

FIGS. 9 and 13 each shows a mutual information (MI) feature extraction module 900. In FIG. 9, module 900 (shown as 900*a*) is configured to determine auto-mutual information at lag from the photoplethysmographic signal(s) (e.g., red photoplethysmographic signal and the infrared photoplethysmographic signal). In FIG. 13, module 900 (shown as 1300*b*) is configured to determine auto-mutual information at lag from cardiac (e.g., from channel "x" of the PSR device, channel "y" of the PSR device, and/or channel "z" of the PSR device).

Mutual information captures in a probabilistic sense the nonlinear dependence between two signals or trajectories in the PS. Roughly speaking, MI quantifies the question that knowing one trajectory is in state i what would be the probability that the other trajectory is in state j.

$$I(X, Y) = \Sigma_{y\in Y}\Sigma_{x\in X}\, p(x, y)\,\log\left(\frac{p(x, y)}{p(x)p(y)}\right) \quad \text{(Equatuion 14.1)}$$

Auto mutual information of X may be obtained by replacing signal Y in Equation 14.1 with a lagged version of X (i.e. X(t+τ)). The AMI is thus going to be a function of lag τ. The lag at which AMI attains its minimum is used as a feature.

Formally, auto mutual information at lag T can be defined per Equation 14.2.

$$I(x_i; x_{i+1}) = \Sigma_{x_i\in x_{i+1}}\Sigma_{x_{i+1}\in x_i}\, p(x_i, x_{i+1})\,\log\left(\frac{p(x_i, x_{i+1})}{p(x_i)p(x_{i+1})}\right) \quad \text{(Equation 14.2)}$$

Mutual information is calculated, in some embodiments, by partitioning the phase space (PS) and calculating the joint probability distributions. In some embodiment, a ratio $$\frac{I_{XY} I_{XY}}{I_{XX} I_{YY}}$$

is calculated as normalized MI.

The input parameter, in some embodiments, is the number of bins. The value used in the study is 128. Other bin numbers may be used.

As shown in FIG. 9, module 900*a* may output auto mutual information from each respective photoplethysmographic signal (e.g., of the red photoplethysmographic signal and/or of the infrared photoplethysmographic signal).

In FIG. 13, module 1300*b* may output auto mutual information determined from each respective cardiac signal (e.g., from acquired channel "x" of the PSR device, acquired channel "y" of the PSR device, and/or acquired channel "z" of the PSR device).

Cross Correlation

Figure 10:
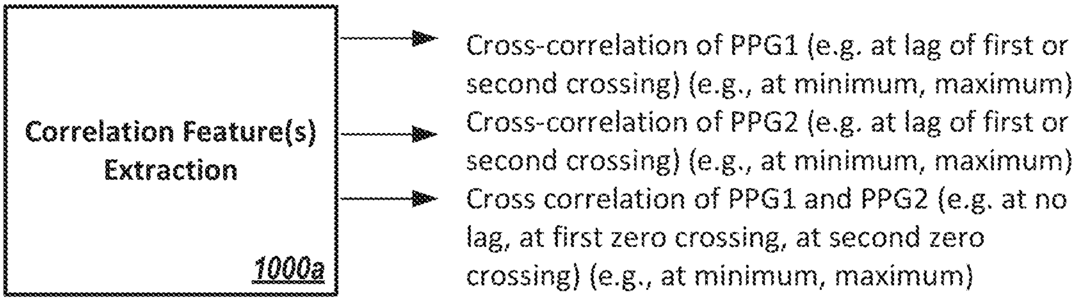
FIGS. 10 and 15 each shows correlation feature extraction module in accordance with an illustrative embodiment.
Figure 14:
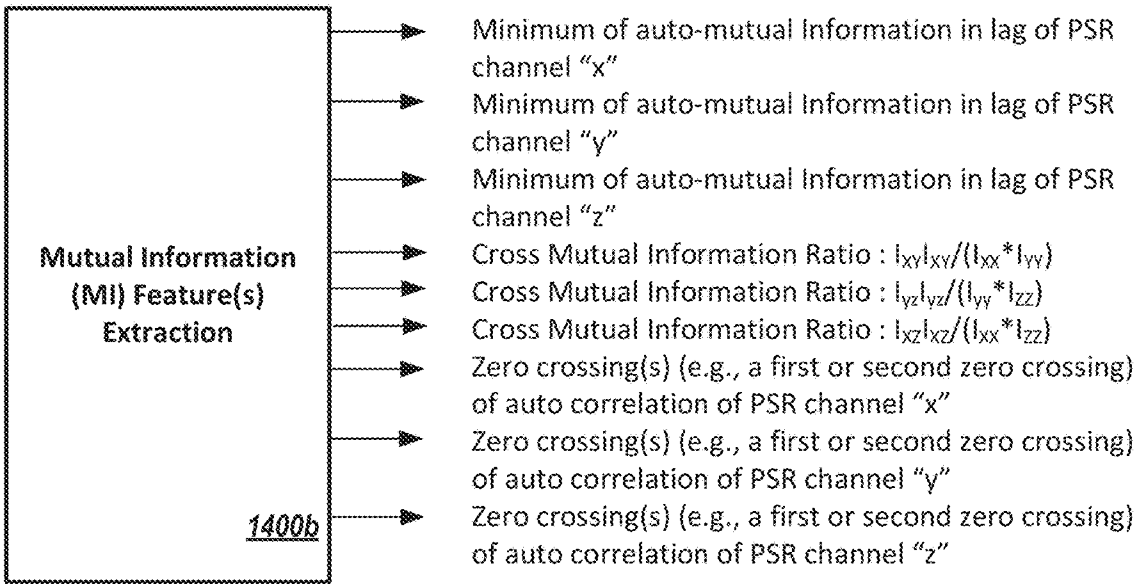

FIGS. 10 and 14 each shows correlation feature extraction module 1000. In FIG. 10, module 1000 (shown as 1000*a*) is configured to determine autocorrelation and cross-correlation at zero crossing between the acquired red photoplethysmographic signal and the infrared photoplethysmographic signal. In FIG. 14, module 1000 (shown as 1400*b*) is configured to determine autocorrelation and cross-correlation at zero crossing between the acquired cardiac signals (e.g., between channels "x" and "y", between channels "x" and "z", and between channels "y" and "z").

The nonlinear dependence was quantified through mutual information. The linear interactions between two random variables or signals can be identified by using cross correlation. The cross-correlation function is defined as:

$$C_{XY}(\tau) = \frac{\langle (X(t) - \overline{X})(Y(t+\tau) - \overline{Y}) \rangle}{\sigma_X \sigma_Y} \quad \text{(Equation 15)}$$

Figure 15:
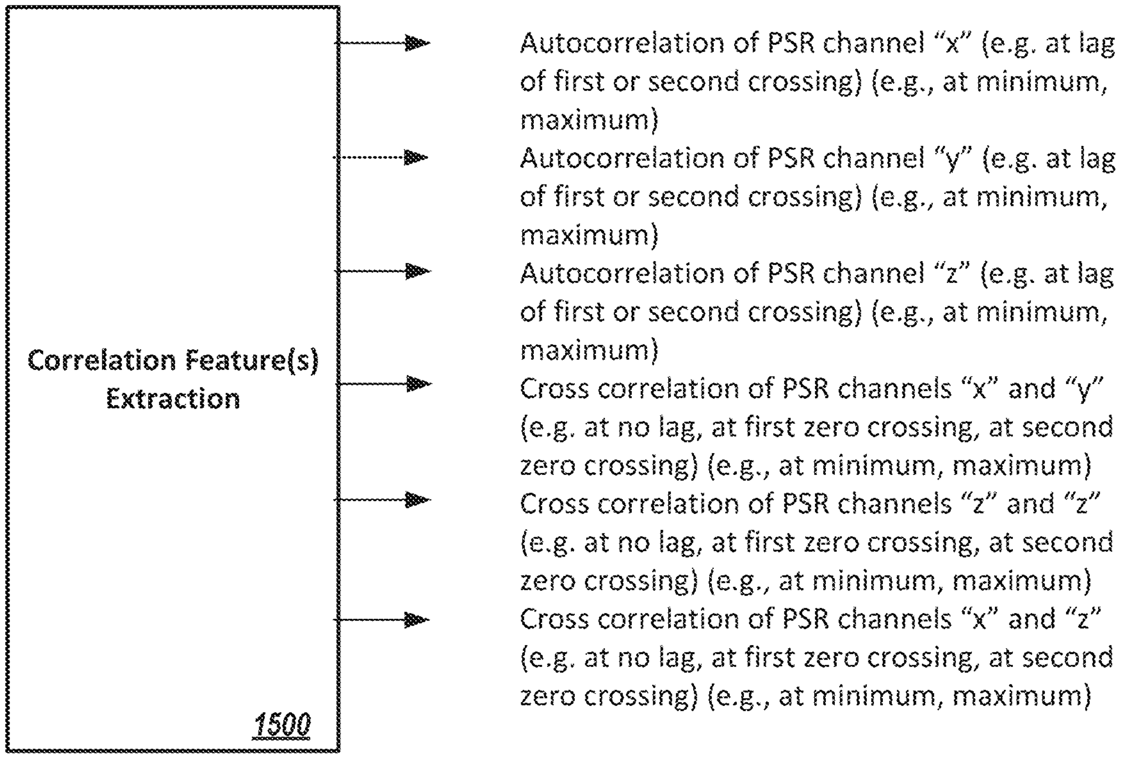

As shown in FIGS. 10 and 15, in some embodiments, the first and second zero crossing, the maximum correlation, the delay at this maximum and the value at T=0 are extracted as features.

DISCUSSION

Systems whose behavior or state evolves in time are called dynamical systems (DS); these systems can be deterministic or stochastic. In the former case, the behavior of the system is governed by deterministic rules and there is no randomness in the system, albeit random-like response may be observed; in the latter case, however, the system evolves as a stochastic process in which randomness is the driving mechanism.

Deterministic dynamical systems may exhibit behaviors which seem to be completely random even though there is no randomness in the system. This type of response, called chaos, is a trait of nonlinear deterministic dynamical systems. The nonlinearity in these systems couples the responses of comprising components in a complex way giving rise to random-like behavior. These types of dynamics can be identified and characterized by using the mathematical techniques of nonlinear dynamical systems.

As used herein, where reference is made to nonlinear dynamical systems the deterministic one is intended.

One important feature of the chaotic behavior of NDS is their sensitive dependence on initial condition; a slight difference in the starting state will grow exponentially fast leading to two completely different behavior in a relatively short amount of time. This growth rate may be quantified by using the Lyapunov exponent (LE). Given long enough time, the trajectory of the motion of a chaotic system fills a bounded (for dissipative systems) region of the phase space; the ensuing geometry is very complex and has fractal properties. This object is also referred to as an attractor. To study this geometric aspect of chaos, fractal mathematics is used; fractal dimension is one such techniques. Entropy is a measure that combines both the dynamical and geometrical aspects of chaos and takes a probabilistic view to this phenomenon. These and other techniques will be introduced in the following sections.

Cardiovascular system with its elaborate conduction and mechanical subsystems may be considered as an NDS; the chaoticity in the physiological function allows the system to better respond to the extrinsic conditions. When the internal characteristics of a DS changes for example due to some parameter change, its behavior may go through a bifurcation and thereby produce a response that has different characteristics. In the context of cardiovascular system, this translates to different NDS features values (e.g., LE) when the heart moves from a normal state to a pathological state.

Dynamical systems features often require that the measurement signal is long enough so that it creates a good representation in the phase space. In reality, however, it may not be possible to acquire the cardiovascular signal for that long. Consequently, the features extracted should not be deemed as exact. In some embodiments, signals are downsampled to 250 Hz. Higher sampling rate may be used but would be subject to higher computation requirements and a considerable portion of it will be noise. In some embodiments, signals are baseline wander removed and filtered for noise and main's frequencies.

Poincaré Map Feature Extraction

As shown in FIG. 1, in some embodiments, the system 100 includes a Poincaré feature extraction module 120 configured to evaluate geometric and topographic properties of a Poincaré map object generated from the photoplethysmographic signal(s) 104.

In some embodiments, the analyses include extracting statistical and geometrical features of generated Poincaré maps.

FIG. 16 shows experimental results from a study that indicates clinical predictive value of certain dynamical features extracted from generated Poincaré maps of photoplethysmographic signal(s) (red photoplethysmographic signals and infrared photoplethysmographic signals) that indicates a disease or abnormal condition, or an indicator of one, in accordance with an illustrative embodiment. As noted above, although the data set notes that prediction/estimation are with respect to certain population sets (e.g., based on gender) and disease or condition, or an indicator of one, the experimental results are merely stratified according to these criteria in the presented analysis. Indeed, the experimental results and the methods and systems discussed herein provides a basis to diagnose the presence or non-presence and/or severity and/or localization (where applicable) of diseases or conditions, such as heart failure (HF) in general even when ejection fraction (EF) is preserved and without necessarily correlating it to an LVEDP level. In other words, the instant system and method may be used to make non-invasive diagnoses or determinations of the presence or non-presence and/or severity and/or localization (where applicable) of various forms of heart failure (HF), as well as other diseases and/or conditions without LVEDP determinations/estimates.

In the study, a first type of Poincaré maps of photoplethysmographic signal(s) 104 between pre-defined landmarks (e.g., peaks, crossovers) in the red photoplethysmographic signal and the infrared photoplethysmographic signal were evaluated. In addition, a second type of Poincaré maps of photoplethysmographic signal(s) 104 between pre-defined landmarks (e.g., peaks, crossovers) in same red photoplethysmographic signal and the same infrared photoplethysmographic signal were evaluated.

From the Poincaré maps, the study evaluated statistical properties including mean, median, mode, standard deviation, skewness, and kurtosis. The study also evaluated geometric properties including: ellipse fitting based on points that contain 3 standard deviation of the data; major and minor diameters and orientation.

Table 6 provides a description of each of the assessed dynamical extracted parameters of FIG. 16. In the table, a photoplethysmographic signal are referred to as a "PPG signal". Indeed, as noted above, in a Poincaré map, reference to time is synonymous, and thus can be used interchangeably, with respect to a data point in a given data set. Further, reference to consecutive time or data points can refer to the immediate data point or time increment as well as a data point or time increment of some fixed increment.

TABLE 6

| | |
|---|---|
| alphaShapePoincaréOutput. alphaShapeDensity | Poincaré map of time from the PPG signal peak at a first time x − 1 to a second time x vs. the second time x to a third time x + 1, over a series of consecutive windows, and as enclosed with an alpha shape, then characterized by the density (surface area normalized by the number of data points). |
| alphaShapePoincaréOutput. convexSurfaceArea | Poincaré map of time from the PPG signal peak at a first time x − 1 to a second time x vs. the second time x to a third time x + 1, over a series of consecutive windows, and as enclosed with a convex hull and characterized by the surface area. |
| alphaShapePoincaréOutput.perim | Poincaré map of time from the PPG signal peak at a first time x − 1 to second time x vs. the second time x to a third time x + 1, over a series of consecutive windows, and as enclosed with an alpha shape, then characterized by the perimeter. |
| alphaShapePoincaréOutput. perimSurfaceAreaRatio | Poincaré map of time from the PPG signal peak at a first time x − 1 to a second time x vs. the second time x to a third time x + 1, over a series of consecutive windows, and as enclosed with an alpha shape, then characterized by the ratio of the perimeter of that alpha shape over the surface area of that alpha shape. |

TABLE 6-continued

| | |
|---|---|
| alphaShapePoincaréOutput.porosity | Poincaré map of time from the PPG signal peak at a first time x − 1 to a second time x vs. the second time x to a third time x + 1, over a series of consecutive windows, and as enclosed with an alpha shape, then characterized by the porosity of the alpha shape. |
| alphaShapePoincaréOutput.surfaceArea | Poincaré map of time from the PPG signal peak at a first time x − 1 to a second time x vs. the second time x to a third time x + 1, over a series of consecutive windows, and as enclosed with an alpha shape, then characterized by the surface area of the alpha shape. |
| alphaShapePoincaréOutput.voidArea | Poincaré map of time from the PPG signal peak at a first time x − 1 to a second time x vs. the second time x to a third time x + 1, over a series of consecutive windows, and as enclosed with an alpha shape, then characterized difference in the surface areas of the convex hull and the alpha shape. |
| histSD | Standard deviation of time differences between adjacent PPG peaks. |
| largestClusterEllipse.a | Sub-axis (radius) of the X axis of the non-tilt ellipse encompassing the largest cluster in the Poincaré map. |
| largestClusterEllipse.b | Sub-axis (radius) of the Y axis of the non-tilt ellipse encompassing the largest cluster in the Poincaré map. |
| largestClusterEllipse.long_axis | Size of the long axis of the ellipse encompassing the largest cluster in the Poincaré map. |
| largestClusterEllipse.short_axis | Size of the short axis of the ellipse encompassing the largest cluster in the Poincaré map. |
| largestClusterEllipse.X0 | Center at the X axis of the non-tilt ellipse encompassing the largest cluster in the Poincaré map. |
| numberOfKernelDensityModes | Number of major modes in the kernel density quantification of the histogram of time differences between adjacent PPG peaks. |
| numClusters | The number of clusters in the Poincaré map, as detected by the DBSCAN clustering algorithm. |
| sarleBiomodalityCoeff | Quantification of bimodality of a distribution, using skewness and kurtosis. |

FIG. 16 shows that various geometric features extracted from a Poincaré plot (also referred to as a Poincaré map) has potential clinical relevance in predicting/estimating the presence, non-presence, localization (where applicable), and/or severity of coronary artery disease and/or disease and/or condition associated with an elevated or abnormal LVEDP.

FIG. 16, for example, shows that density (e.g., surface area normalized by number of data points) of a generated alpha shape of the Poincaré map of a photoplethysmographic signal (shown as "alphaShapePoincaréOutput.alphaShapeDensity") has an AUC value of 0.538 in predicting/estimating the presence, non-presence, localization (where applicable), and/or severity of coronary artery disease. An AUC value greater than 0.5 has significance.

Further, FIG. 16 shows that the surface area of a convex hull that encloses an alpha shape generated from the Poincaré map (shown as "alphaShapePoincaréOutput.convexSurfaceArea") has an AUC value of 0.533 in predicting/estimating the presence, non-presence, localization (where applicable), and/or severity of coronary artery disease. An AUC value greater than 0.5 has significance.

Further, FIG. 16 shows that the perimeter of the alpha shape generated from the Poincaré map of the photoplethysmographic signal (shown as "alphaShapePoincaréOutput.perim") has a t-test p-value of 0.044; a mutual information value of 1.295; and an AUC value of 0.523 in predicting/estimating the presence, non-presence, localization (where applicable), and/or severity of coronary artery disease. An AUC value greater than 0.5 has significance; a p-value of less than 0.05 has significance, a mutual information greater than 0.5 has significance.

Further, FIG. 16 shows that ratio of the perimeter of an alpha shape over the surface area of that alpha shape (shown as "alphaShapePoincaréOutput.perimSurfaceAreaRatio") has a t-test p-value of 0.00001; a mutual information value of 1.841; and an AUC value of 0.566 in predicting/estimating the presence, non-presence, localization (where applicable), and/or severity of coronary artery disease. Further, the same feature has a t-test p-value of 0.011 in predicting/estimating an elevated or abnormal LVEDP (which may indicate the presence, non-presence, and/or severity of a disease and/or condition). An AUC value greater than 0.5 has significance; a p-value of less than 0.05 has significance; a mutual information greater than 0.5 has significance.

Further, FIG. 16 shows that the porosity of a generated alpha shape of the Poincaré map of the photoplethysmographic signal (shown as "alphaShapePoincaréOutput.porosity") has a t-test p-value of 0.0035 and an AUC value of 0.509 in predicting/estimating the presence, non-presence, localization (where applicable), and/or severity of coronary artery disease. An AUC value greater than 0.5 has significance; a p-value of less than 0.05 has significance.

Further, FIG. 16 shows that surface area of the Poincaré map of the photoplethysmographic signal (shown as "alphaShapePoincaréOutput.surfaceArea") has AUC value of 0.549 in predicting the predicting/estimating the presence, non-presence, localization (where applicable), and/or severity of coronary artery disease. An AUC value greater than 0.5 has significance.

Further, FIG. 16 shows that void area (e.g., difference in the surface areas of the convex hull and the alpha shape) of the Poincaré map of the photoplethysmographic signal (shown as "alphaShapePoincaréOutput.voidArea") has AUC value of 0.505 in predicting/estimating the presence, non-presence, localization (where applicable), and/or severity of coronary artery disease. An AUC value greater than 0.5 has significance.

In addition, FIG. 16 shows that standard deviation of time differences between adjacent PPG peaks has AUC value of 0.506 in predicting/estimating the presence, non-presence, localization (where applicable), and/or severity of coronary artery disease. An AUC value greater than 0.5 has significance.

In addition, FIG. 16 shows that parameters associated with a fitted ellipse in a cluster of the Poincaré map has potential clinical relevance in predicting/estimating the presence, non-presence, localization (where applicable), and/or severity of coronary artery disease. Specifically, FIG. 16 shows that the sub-axis (radius) of the x-axis of the non-tilt ellipse encompassing the largest cluster in the Poincaré map (shown as "largestClusterEllipse.a") has an AUC value of 0.502 in predicting/estimating the presence, non-presence, localization (where applicable), and/or severity of coronary artery disease. An AUC value greater than 0.5 has significance.

Further, FIG. 16 shows that the sub-axis (radius) of the y-axis of the non-tilt ellipse encompassing the largest cluster in the Poincaré map (shown as "largestClusterEllipse.b")

has an AUC value of 0.502 in predicting/estimating the presence, non-presence, localization (where applicable), and/or severity of coronary artery disease. An AUC value greater than 0.5 has significance.

Further, FIG. 16 shows that the size of the long axis of the ellipse encompassing the largest cluster in the Poincaré map (shown as "largestClusterEllipse.long_axis") has mutual information value of 1.37 and an AUC value of 0.508 in predicting/estimating the presence, non-presence, localization (where applicable), and/or severity of coronary artery disease. An AUC value greater than 0.5 has significance; a mutual information value greater than 1.0 has significance.

Further, FIG. 16 shows that the size of the short axis of the ellipse encompassing the largest cluster in the Poincaré map (shown as "largestClusterEllipse.short_axis") has a mutual information value of 1.086 and an AUC value of 0.527 in predicting/estimating the presence, non-presence, localization (where applicable), and/or severity of coronary artery disease. An AUC value greater than 0.5 has significance; a mutual information value greater than 1.0 has significance.

Further, FIG. 16 shows that the center at the x-axis of the non-tilt ellipse encompassing the largest cluster in the Poincaré map (shown as "largestClusterEllipse.X0") has a mutual information value of 1.04 in predicting/estimating the presence, non-presence, localization (where applicable), and/or severity of coronary artery disease. A mutual information value greater than 1.0 has significance.

In addition, FIG. 16 shows that the number of major modes in a kernel density quantification of the histogram of time differences between adjacent PPG peaks (shown as "numberOfKernelDensityModes") has a test p-value of 0.049 in predicting/estimating the presence, non-presence, localization (where applicable), and/or severity of coronary artery disease. A p-value of less than 0.05 has significance.

In addition, FIG. 16 shows that the number of clusters in the Poincaré map, as detected by the DBSCAN clustering algorithm (shown as "numClusters"), has a t-test p-value of 0.013 is predicting/estimating an elevated or abnormal LVEDP (which may indicate the presence, non-presence, and/or severity of a disease and/or condition). A p-value of less than 0.05 has significance.

In addition, FIG. 16 shows that the quantification of bimodality of a distribution using skewness and kurtosis (shown as "sarleBiomodalityCoef") has a t-test p-value of 0.045 in predicting/estimating the presence, non-presence, localization (where applicable), and/or severity of coronary artery disease and a mutual information value of 1.234 in predicting/estimating an elevated or abnormal LVEDP (which may indicate the presence, non-presence, and/or severity of a disease and/or condition). A p-value of less than 0.05 has significance; a mutual information value of greater than 1.0 has significance.

Figure 17:
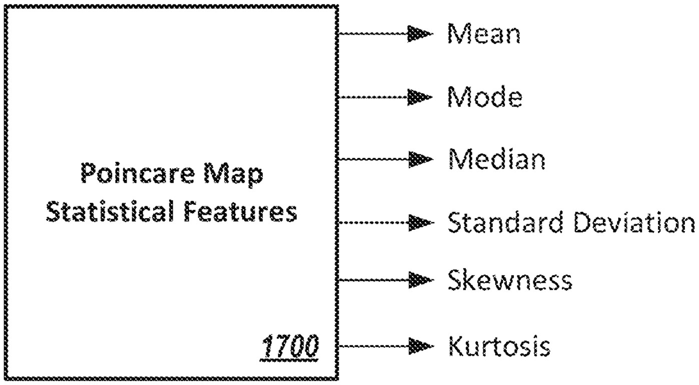
FIG. 17 shows a Poincaré map statistical feature extraction module in accordance with an illustrative embodiment.
Figure 18:
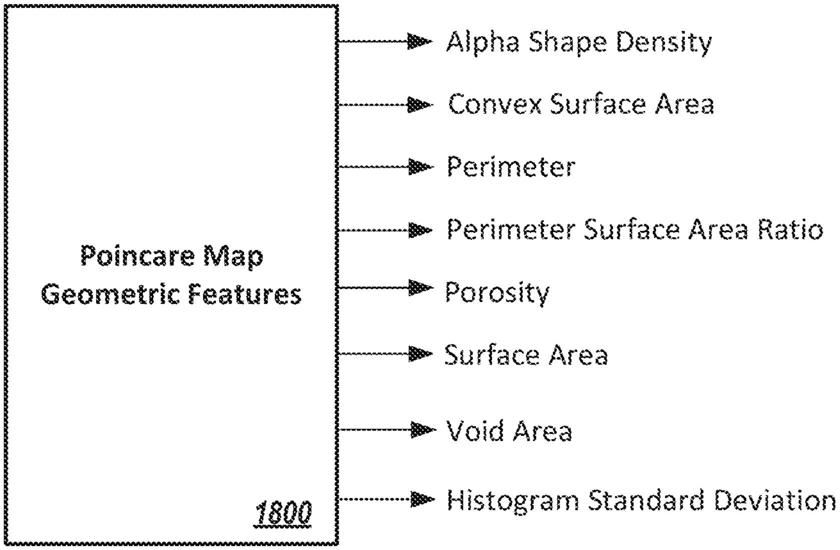
FIG. 18 shows a Poincaré map geometric feature extraction module in accordance with an illustrative embodiment.
Figure 19:
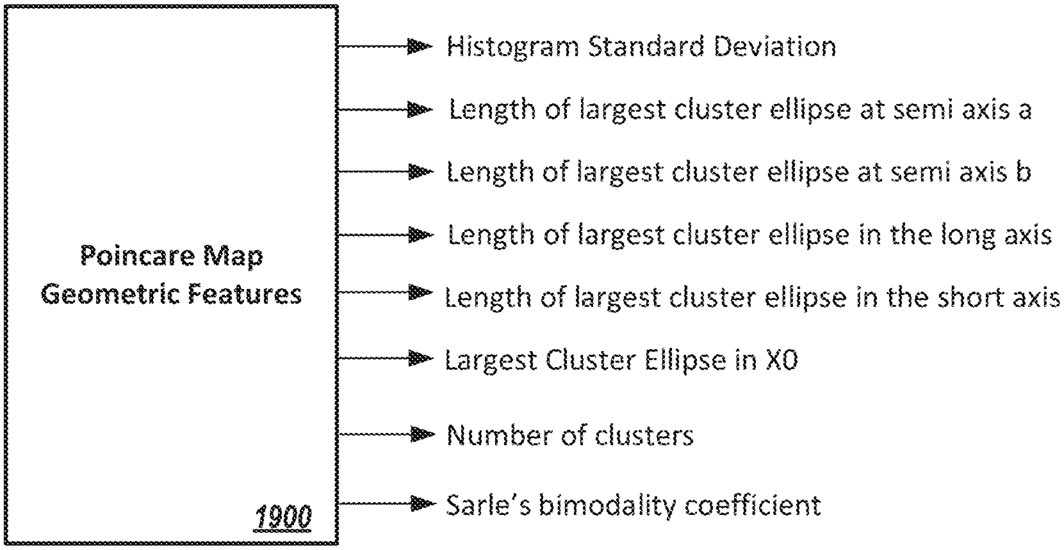
FIG. 19 shows a cluster map geometric feature extraction module in accordance with an illustrative embodiment.

FIGS. 17-19 each shows example Poincaré map feature analysis modules 120 of FIG. 1 in accordance with an illustrative embodiment. The outputs of the modules of FIGS. 17-19 are merely illustrative. Embodiments may be implemented with some or all of the outputs shown. In some embodiments, additional outputs are generated.

FIG. 17 shows a Poincaré map statistical feature extraction module 1700. Module 1700 is configured, in some embodiments, to determine mean, mode, median, standard deviation, skewness, and kurtosis of periodicity between landmarks in a same photoplethysmographic signal or of periodicity between landmarks in the red photoplethysmographic signal and the infrared photoplethysmographic signal.

FIG. 18 shows a Poincaré map geometric feature extraction module 1800. Module 1800 is configured to determine geometric features from a generated alpha shape of a Poincaré map object. In some embodiments, the Poincaré map and its corresponding object can be generated from periodicity between landmarks in the red photoplethysmographic signal and the infrared red photoplethysmographic signal. In some embodiments, the Poincaré map and its corresponding object can be generated from periodicity between landmarks in the same photoplethysmographic signal (e.g., infrared photoplethysmographic signal and/or the red photoplethysmographic signal).

Figure 18A:
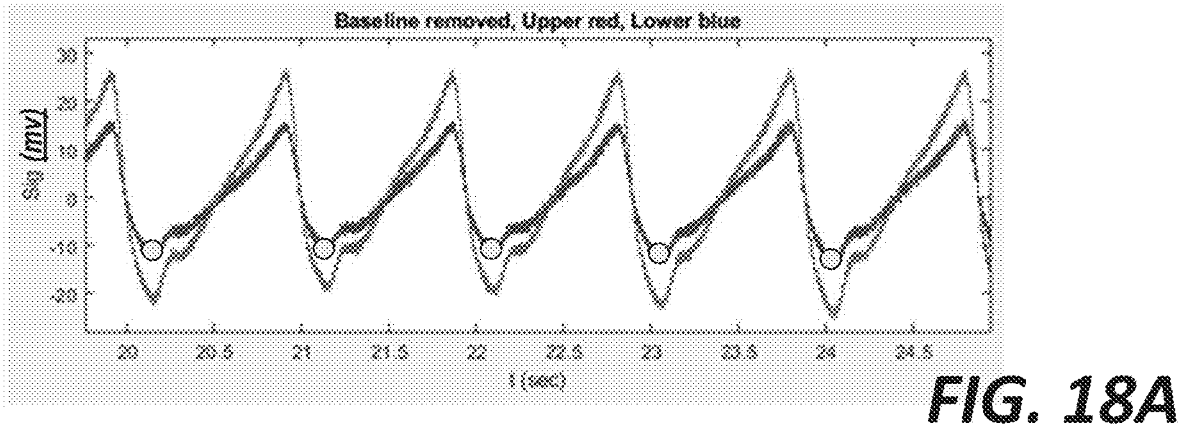
FIG. 18A shows example landmarks in an infrared photoplethysmographic signal in accordance with an illustrative embodiment.
Figure 18B:
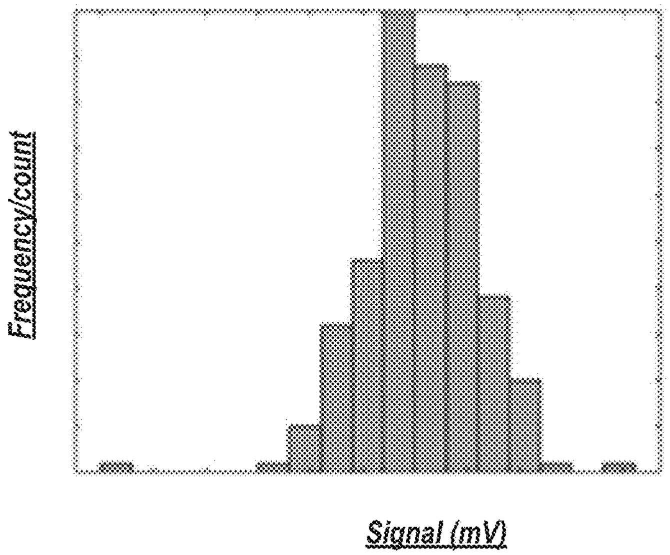
FIG. 18B shows an example distribution of periodicity between same landmarks from neighboring cycles in the infrared photoplethysmographic signal in accordance with an illustrative embodiment.
Figure 18C:
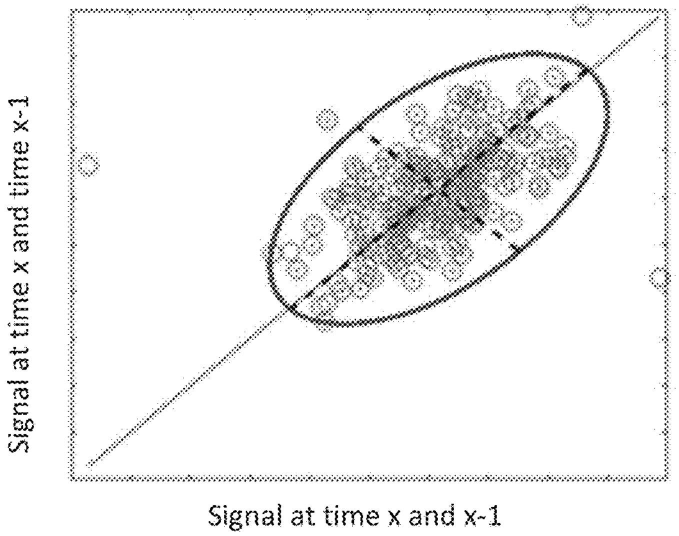
FIG. 18C shows an example Poincaré map generated from the distribution of periodicity among lowest peak landmarks in the infrared photoplethysmographic signal in accordance with an illustrative embodiment.

FIG. 18A shows example landmarks (lowest peak) in an infrared photoplethysmographic signal. In FIG. 18A, the x-axis shows time (in seconds) and the y-axis shows the signal amplitude in millivolts (my). FIG. 18B shows an example distribution of variance of the amplitude values among neighboring cycles in the infrared photoplethysmographic signal in a histogram. In FIG. 18B, the x-axis of the histogram shows signal amplitude (in mV) and the y-axis shows the frequency/count. FIG. 18C shows an example Poincaré map generated from the amplitude values of the infrared photoplethysmographic signal at time x and x−1 in the x-axis and time x and x+1 in the y-axis. That is, each assessed parameter (e.g., signal amplitude) at a given time/data point is shown in the Poincaré map with respect to the next time/data point (e.g., [$x_i$, $x_{i+1}$] versus [$x_i$, $x_{i-1}$]). The Poincaré map thus facilitates the analysis of variability of a given parameter (e.g., variability in the lowest peak landmarks) between cycles in the acquired data set. Similar analysis may be applied to any of the parameters and features discussed herein.

From the Poincaré map, the system generates an alpha shape to which geometric features of the resulting alpha shape are extracted.

Per FIG. 18, in some embodiments, Poincaré map geometric feature extraction module 1800 is configured to extract a density value from an alpha shape of the Poincaré map. In some embodiments, module 1800 determines the density as the surface area normalized by the number of data points.

Per FIG. 18, in some embodiments, Poincaré map geometric feature extraction module 1800 is configured to extract a convex surface area value from an alpha shape of the Poincaré map. In some embodiments, module 1800 determines the convex surface area as the surface area of a convex hull that is generated to encompass an alpha shape of the Poincaré map.

Per FIG. 18, in some embodiments, Poincaré map geometric feature extraction module 1800 is configured to extract a perimeter value from an alpha shape of the Poincaré map.

Per FIG. 18, in some embodiments, Poincaré map geometric feature extraction module 1800 is configured to extract a perimeter value and a surface area value from an alpha shape of the Poincaré map. Module 1300 may generate a ratio based on the perimeter value and the surface area.

Per FIG. 18, in some embodiments, Poincaré map geometric feature extraction module 1800 is configured to extract a porosity value from an alpha shape of the Poincaré map.

Per FIG. 18, in some embodiments, Poincaré map geometric feature extraction module 1800 is configured to extract a surface area from an alpha shape of the Poincaré map.

Per FIG. 18, in some embodiments, the Poincaré map geometric feature extraction module 1800 is configured to extract a void area from an alpha shape of the Poincaré map. In some embodiments, module 1800 determines the void area as the difference in the surface areas of the convex hull and the alpha shape.

Per FIG. 19, in some embodiments, Poincaré map geometric feature extraction module 1900 is configured to extract standard deviation of time differences between adjacent peaks in the photoplethysmographic signal(s).

In FIG. 19, cluster map geometric feature extraction module 1900 is configured to also determine geometric features from a determined clusters of a Poincaré map object.

As shown in FIG. 19, in some embodiments, module 1900 is configured to determine sub-axis (radius) of the x-axis of the non-tilt ellipse encompassing the largest cluster in the Poincaré map. In some embodiments, module 1900 is configured to determine sub-axis (radius) of the Y axis of the non-tilt ellipse encompassing the largest cluster in the Poincaré map. In some embodiments, module 1900 is configured to determine the size of the long axis of the ellipse encompassing the largest cluster in the Poincaré map. In some embodiments, module 1900 is configured to determine size of the short axis of the ellipse encompassing the largest cluster in the Poincaré map. In some embodiments, module 1900 is configured to determine center at the X axis of the non-tilt ellipse encompassing the largest cluster in the Poincaré map. In some embodiments, module 1900 is configured to determine number of major modes in the kernel density quantification of the histogram of time differences between adjacent PPG peaks. In some embodiments, module 1900 is configured to determine the number of clusters in the Poincaré map, as detected by the DBSCAN clustering algorithm.

In some embodiments, module 1900 is configured to determine quantification of bimodality of a distribution, using skewness and kurtosis.

The module 1900 may generate one, some, or all of the parameters discussed above, e.g., for subsequent analysis and/or use in a diagnosis of a disease state or condition.

Per FIG. 16, it is shown that these parameters have some statistical relevance, dependencies, or clinical value in assessing elevated or abnormal LVEDP and coronary artery disease.

Coronary Artery Disease—Learning Algorithm Development Study

A "Coronary Artery Disease—Learning Algorithm Development" (CADLAD) study was untaken that acquired photoplethysmographic signals and cardiac signals to support the development and testing of the machine-learned algorithms.

In the study, paired clinical data were used to guide the design and development of the pre-processing, feature extraction, and machine learning phase of the development. That is, the collected clinical study data are split into cohorts: a training cohort, a validation cohort, and a verification cohort. In the study, each acquired data set is first pre-processed to clean and normalize the data. Following the pre-processing processes, a set of features are extracted from the signals in which each set of features is paired with a representation of the true condition—for example, the binary classification of the presence or absence of significant CAD or the scored classification of the presence of significant CAD in a given coronary artery.

The assessment system (e.g., 114, 114*a*, 114*b*), in some embodiments, automatically and iteratively explores combinations of features in various functional permutations with the aim of finding those combinations which can successfully match a prediction based on the features. To avoid overfitting of the solutions to the training data, the validation set is used as a comparator. Once candidate predictors have been developed, they are then manually applied to a verification data set to assess the predictor performance against data that has not been used at all to generate the predictor. Provided that the data sets are sufficiently large, the performance of a selected predictor against the verification set will be close to the performance of that predictor against new data.

Healthcare Provider Portal

Referring to FIG. 1 (as well as FIGS. 1A and 1), the system 100 (e.g., 100*a*, 100*b*), in some embodiments, includes a healthcare provider portal to display an assessment of disease state or condition (e.g., associated with an elevated or abnormal LVEDP and/or coronary artery disease) in a report. In some embodiments, the report is structured as an angiographic-equivalent report. The physician or clinician portal, in some embodiments, is configured to access and retrieve reports from a repository (e.g., a storage area network). The physician or clinician portal and/or repository can be HIPAA-compliant. An example healthcare provider portal is provided in U.S. patent application Ser. No. 15/712,104, entitled "Method and System for Visualization of Heart Tissue at Risk", which is incorporated by reference herein in its entirety. Although in certain embodiments, the portal is configured for presentation of patient medical information to healthcare professionals, in other embodiments, the healthcare provider portal can be made accessible to patients, researchers, academics, and/or other portal users. This portal may be used for a wide variety of clinical and even research needs in a wide variety of settings—from hospitals to emergency rooms, laboratories, battlefield or remote settings, at point of care with a patient's primary care physician or other caregiver, and even the home.

Machine-Based Classifier

Machine learning techniques predict outcomes based on sets of input data. For example, machine learning techniques are being used to recognize patterns and images, supplement medical diagnoses, and so on. Machine learning techniques rely on a set of features generated using a training set of data (i.e., a data set of observations, in each of which an outcome to be predicted is known), each of which represents some measurable aspect of observed data, to generate and tune one or more predictive models. For example, observed signals (e.g., heartbeat signals from a number of subjects) may be analyzed to collect frequency, average values, and other statistical information about these signals. A machine learning technique may use these features to generate and tune a model that relates these features to one or more conditions, such as some form of cardiovascular disease (CVD), including coronary artery disease (CAD), and then apply that model to data sources with unknown outcomes, such as an undiagnosed patient or future patterns, and so on. Conventionally, in the context of cardiovascular disease, these features are manually selected from conventional electrocardiogram and combined by data scientists working with domain experts.

Examples of embodiments of machine learning includes, but not limited to, decision trees, random forests, SVMs, neural networks, linear models, Gaussian processes, nearest neighbor, SVMs, Naïve Bayes. In some embodiment, machine learning may be implemented, e.g., as described in U.S. patent application Ser. No. 15/653,433, entitled "Discovering Novel Features to Use in Machine Learning Techniques, such as Machine Learning Techniques for Diagnosing Medical Conditions"; and U.S. patent application Ser. No. 15/653,431, entitled "Discovering Genomes to Use in Machine Learning Techniques"; each of which are incorporated by reference herein in its entirety.

Example Computing Device

Figure 20:
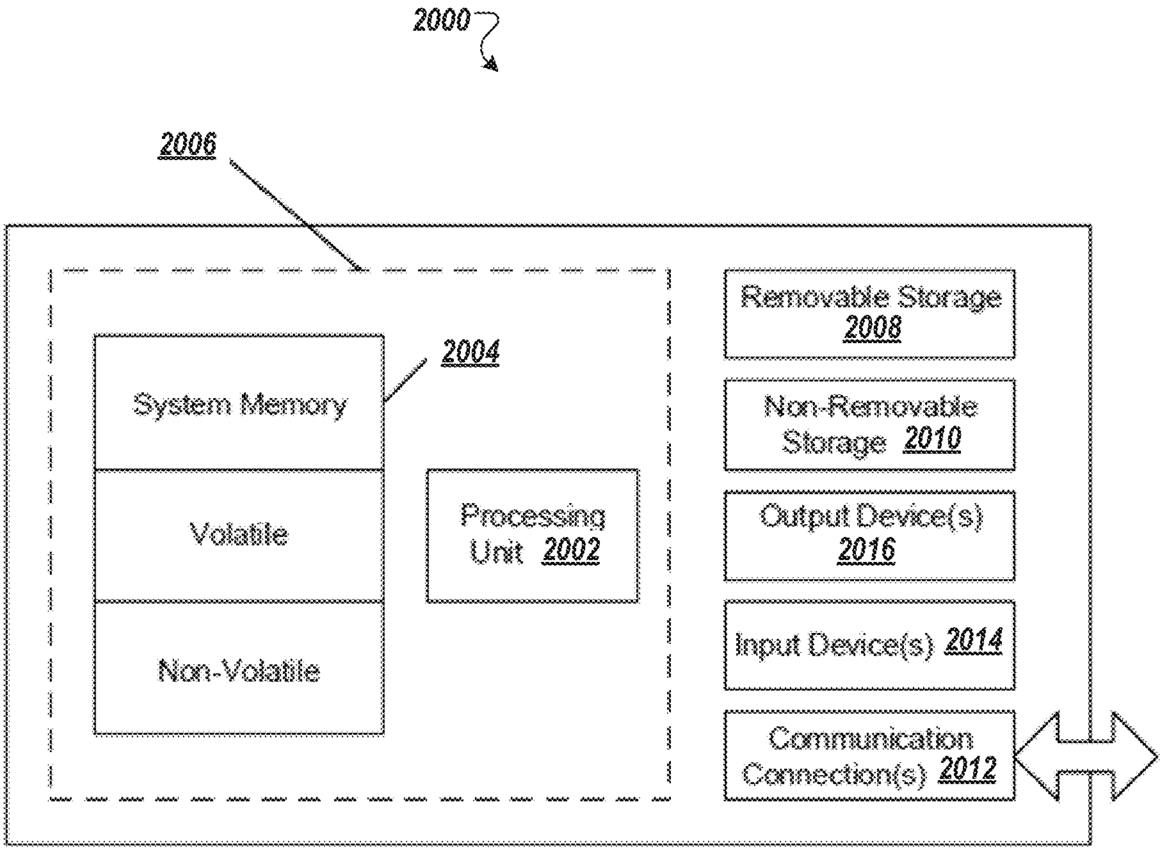
FIG. 20 shows an example computing environment in which example embodiments of the analysis system may be implemented.

FIG. 20 shows an example computing environment in which example embodiments of the analysis system 114 and aspects thereof may be implemented.

The computing device environment is only one example of a suitable computing environment and is not intended to suggest any limitation as to the scope of use or functionality.

Numerous other general-purpose or special purpose computing devices environments or configurations may be used. Examples of well-known computing devices, environments, and/or configurations that may be suitable for use include, but are not limited to, personal computers, server computers, handheld or laptop devices, mobile phones, wearable devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 20, an example system for implementing aspects described herein includes a computing device, such as computing device 2000. In its most basic configuration, computing device 2000 typically includes at least one processing unit 2002 and memory 2004. Depending on the exact configuration and type of computing device, memory 2004 may be volatile (such as random access memory (RAM)), non-volatile (such as read-only memory (ROM), flash memory, etc.), or some combination of the two. This most basic configuration is illustrated in FIG. 20 by dashed line 2006.

Computing device 2000 may have additional features/functionality. For example, computing device 2000 may include additional storage (removable and/or non-removable) including, but not limited to, magnetic or optical disks or tape. Such additional storage is illustrated in FIG. 20 by removable storage 2008 and non-removable storage 2010.

Computing device 2000 typically includes a variety of computer readable media. Computer readable media can be any available media that can be accessed by the device 2000 and includes both volatile and non-volatile media, removable and non-removable media.

Computer storage media include volatile and non-volatile, and removable and non-removable media implemented in any method or technology for storage of information such as computer readable instructions, data structures, program modules or other data. Memory 2004, removable storage 2008, and non-removable storage 2010 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 2000. Any such computer storage media may be part of computing device 2000.

Computing device 2000 may contain communication connection(s) 2012 that allow the device to communicate with other devices. Computing device 2000 may also have input device(s) 2014 such as a keyboard, mouse, pen, voice input device, touch input device, etc., singly or in combination. Output device(s) 2016 such as a display, speakers, printer, vibratory mechanism, etc. may also be included singly or in combination. All these devices are well known in the art and need not be discussed at length here.

It should be understood that the various techniques described herein may be implemented in connection with hardware components or software components or, where appropriate, with a combination of both. Illustrative types of hardware components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

Although example implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, handheld devices, and wearable devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Further examples of processing that may be used with the exemplified method and system are described in: U.S. Pat. No. 9,289,150, entitled "Non-invasive Method and System for Characterizing Cardiovascular Systems"; U.S. Pat. No. 9,655,536, entitled "Non-invasive Method and System for Characterizing Cardiovascular Systems"; U.S. Pat. No. 9,968,275, entitled "Non-invasive Method and System for Characterizing Cardiovascular Systems"; U.S. Pat. No. 8,923,958, entitled "System and Method for Evaluating an Electrophysiological Signal"; U.S. Pat. No. 9,408,543, entitled "Non-invasive Method and System for Characterizing Cardiovascular Systems and All-Cause Mortality and Sudden Cardiac Death Risk"; U.S. Pat. No. 9,955,883, entitled "Non-invasive Method and System for Characterizing Cardiovascular Systems and All-Cause Mortality and Sudden Cardiac Death Risk"; U.S. Pat. No. 9,737,229, entitled "Noninvasive Electrocardiographic Method for Estimating Mammalian Cardiac Chamber Size and Mechanical Function"; U.S. Pat. No. 10,039,468, entitled "Noninvasive Electrocardiographic Method for Estimating Mammalian Cardiac Chamber Size and Mechanical Function"; U.S. Pat. No. 9,597,021, entitled "Noninvasive Method for Estimating Glucose, Glycosylated Hemoglobin and Other Blood Constituents"; U.S. Pat. No. 9,968,265, entitled "Method and System for Characterizing Cardiovascular Systems From Single Channel Data"; U.S. Pat. No. 9,910,964, entitled "Methods and Systems Using Mathematical Analysis and Machine Learning to Diagnose Disease"; U.S. Patent Publication No. 2017/0119272, entitled "Method and Apparatus for Wide-Band Phase Gradient Signal Acquisition"; PCT Publication No. WO2017/033164, entitled "Method and Apparatus for Wide-Band Phase Gradient Signal Acquisition"; U.S. Patent Publication No. 2018/0000371, entitled "Non-invasive Method and System for Measuring Myocardial Ischemia, Stenosis Identification, Localization and Fractional Flow Reserve Estimation"; PCT Publication No. WO2017/221221, entitled "Non-invasive Method and System for Measuring Myocardial Ischemia, Stenosis Identification, Localization and Fractional Flow Reserve Estimation"; U.S. Pat. No. 10,292,596, entitled "Method and System for Visualization of Heart Tissue at Risk"; U.S. patent application Ser. No. 16/402,616, entitled "Method and System for Visualization of Heart Tissue at Risk"; U.S. Patent Publication No. 2018/0249960, entitled "Method and System for Wide-band Phase Gradient Signal Acquisition"; U.S. patent application Ser. No. 16/232,801, entitled "Method and System to Assess Disease Using Phase Space Volumetric Objects"; PCT Application No. IB/2018/060708, entitled "Method and System to Assess Disease Using Phase Space Volumetric Objects"; U.S. Patent Publication No. US2019/0117164, entitled "Methods and Systems of De-Noising Magnetic-Field Based Sensor Data of Electrophysiological Signals"; U.S. patent application Ser. No. 16/232,586, entitled "Method and System to Assess Disease Using Phase Space Tomography and Machine Learning"; PCT Application No. PCT/IB2018/060709, entitled "Method and System to Assess Disease Using Phase Space Tomography and Machine Learning"; U.S. patent application Ser. No. 16/445,158, entitled "Methods and Systems to Quantify and Remove Asynchronous Noise in Biophysical Signals"; U.S. patent application Ser. No. 16/725,402, entitled "Method and System to Assess Disease Using Phase Space Tomography and Machine Learning"; U.S. patent application Ser. No. 16/429,593, entitled "Method and System to Assess Pulmonary Hypertension Using Phase Space Tomography and Machine Learning"; U.S. patent application Ser. No. 16/725,416, entitled "Method and System for Automated Quantification of Signal Quality"; U.S. patent application Ser. No. 16/725,430, entitled "Method and System to Configure and Use Neural Network To Assess Medical Disease"; U.S. patent application Ser. No. 15/653,433, entitled "Discovering Novel Features to Use in Machine Learning Techniques, such as Machine Learning Techniques for Diagnosing Medical Conditions"; U.S. patent application Ser. No. 15/653,431, entitled "Discovering Genomes to Use in Machine Learning Techniques", each of which is incorporated by reference herein in its entirety.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including matters of logic with respect to arrangement of steps or operational flow; plain meaning derived from grammatical organization or punctuation; the number or type of embodiments described in the specification.

While the methods and systems have been described in connection with certain embodiments and specific examples, it is not intended that the scope be limited to the particular embodiments set forth, as the embodiments herein are intended in all respects to be illustrative rather than restrictive.

The methods, systems and processes described herein may be used generate stenosis and FFR outputs for use in connection with procedures such as the placement of vascular stents within a vessel such as an artery of a living (e.g., human) subject, and other interventional and surgical system or processes. In one embodiment, the methods, systems and processes described herein can be configured to use the FFR/stenosis outputs to determine and/or modify, intra operation, a number of stents to be placed in a living (e.g., human), including their optimal location of deployment within a given vessel, among others.

Examples of other biophysical signals that may be analyzed in whole, or in part, using the example methods and systems include, but are not limited to, an electrocardiogram (ECG) data set, an electroencephalogram (EEG) data set, a gamma synchrony signal data set; a respiratory function signal data set; a pulse oximetry signal data set; a perfusion data signal data set; a quasi-periodic biological signal data set; a fetal ECG data set; a blood pressure signal; a cardiac magnetic field data set, and a heart rate signal data set.

The example analysis can be used in the diagnosis and treatment of cardiac-related pathologies and conditions and/or neurological-related pathologies and conditions, such assessment can be applied to the diagnosis and treatment (including, surgical, minimally invasive, and/or pharmacologic treatment) of any pathologies or conditions in which a biophysical signal is involved in any relevant system of a living body. One example in the cardiac context is the diagnosis of CAD and its treatment by any number of therapies, alone or in combination, such as the placement of a stent in a coronary artery, performance of an atherectomy, angioplasty, prescription of drug therapy, and/or the prescription of exercise, nutritional and other lifestyle changes, etc. Other cardiac-related pathologies or conditions that may be diagnosed include, e.g., arrhythmia, congestive heart failure, valve failure, pulmonary hypertension (e.g., pulmonary arterial hypertension, pulmonary hypertension due to left heart disease, pulmonary hypertension due to lung disease, pulmonary hypertension due to chronic blood clots, and pulmonary hypertension due to other disease such as blood or other disorders), as well as other cardiac-related pathologies, conditions and/or diseases. Non-limiting examples of neurological-related diseases, pathologies or conditions that may be diagnosed include, e.g., epilepsy, schizophrenia, Parkinson's Disease, Alzheimer's Disease (and all other forms of dementia), autism spectrum (including Asperger syndrome), attention deficit hyperactivity disorder, Huntington's Disease, muscular dystrophy, depression, bipolar disorder, brain/spinal cord tumors (malignant and benign), movement disorders, cognitive impairment, speech impairment, various psychoses, brain/spinal cord/nerve injury, chronic traumatic encephalopathy, cluster headaches, migraine headaches, neuropathy (in its various forms, including peripheral neuropathy), phantom limb/pain, chronic fatigue syndrome, acute and/or chronic pain (including back pain, failed back surgery syndrome, etc.), dyskinesia, anxiety disorders, conditions caused by infections or foreign agents (e.g., Lyme disease, encephalitis, rabies), narcolepsy and other sleep disorders, post-traumatic stress disorder, neurological conditions/effects related to stroke, aneurysms, hemorrhagic injury, etc., tinnitus and other hearing-related diseases/conditions and vision-related diseases/conditions.

The following patents, applications and publications as listed below and throughout this document are hereby incorporated by reference in their entirety herein.

LIST OF REFERENCES

[1] I. Kononenko, "Machine learning for medical diagnosis: history, state of the art and perspective," Artificial Intelligence in medicine 23 (1) 89-109 (2001).
[2] B. A. Mobley, E. Schechter, W. E. Moore, P. A. McKee, J. E. Eichner, "Predictions of coronary artery stenosis by artificial neural network," Artificial Intelligence in Medicine 18 (3) 187-203 (2000).
[3] V. L. Patel, E. H. Shortliffe, M. Stefanelli, P. Szolovits, M. R. Berthold, R. Bellazzi, A. Abu-Hanna, "The coming of age of artificial intelligence in medicine," Artificial intelligence in medicine 46 (1) 5-17 (2009).
[4] V. Jahmunah, S. L. Oh, V. Rajinikanth, E. J. Ciaccio, K. H. Cheong, U. R. Acharya, et al., "Automated detection of schizophrenia using nonlinear signal processing methods," Artificial Intelligence in Medicine, Vol. 100, 101698 (September 2019).
[5] A. M. Tai, A. Albuquerque, N. E. Carmona, M. Subramanieapillai, D. S. Cha, M. Sheko, Y. Lee, R. Mansur, R. S. McIntyre, "Machine learning and big data: Implications for disease modeling and therapeutic discovery in psychiatry," Artificial Intelligence in Medicine 101704 (2019).
[6] G. K. Hansson, "Inflammation, atherosclerosis, and coronary artery disease," New England Journal of Medicine 352 (16) 1685-1695 (2005).
[7] W. G. Members, D. Lloyd-Jones, R. J. Adams, T. M. Brown, M. Carnethon, S. Dai, G. De Simone, T. B. Ferguson, E. Ford, K. Furie, et al., "Executive summary: heart disease and stroke statistics 2010 update: a report from the American heart association," Circulation 121 (7) 948-954 (2010).
[8] G. A. Mensah, D. W. Brown, "An overview of cardiovascular disease burden in the united states," Health affairs 26 (1) 38-48 (2007).
[9] Y. N. Reddy, A. El-Sabbagh, R. A. Nishimura, "Comparing pulmonary arterial wedge pressure and left ventricular end diastolic pressure for assessment of left-sided filling pressures," JAMA cardiology 3 (6) 453-454 (2018).
[10] M. J. Kern, T. Christopher, "Hemodynamic rounds series II: the LVEDP," Catheterization and cardiovascular diagnosis 44 (1) 70-74 (1998).
[11] J.-H. Park, T. H. Marwick, "Use and limitations of e/e' to assess left ventricular filling pressure by echocardiography," Journal of cardiovascular ultrasound 19 (4) 169-173 (2011).
[12] S. R. Ommen, R. A. Nishimura, C. P. Appleton, F. Miller, J. K. Oh, M. M. Redfield, A. Tajik, "Clinical utility of doppler echocardiography and tissue doppler imaging in the estimation of left ventricular filling pressures: a comparative simultaneous doppler-catheterization study," Circulation 102 (15) 1788-1794 (2000).
[13] J. Allen, "Photoplethysmography and its application in clinical physiological measurement," Physiological measurement 28 (3) R1 (2007).
[14] S. D. Fihn, J. M. Gardin, J. Abrams, K. Berra, J. C. Blankenship, A. P. Dallas, P. S. Douglas, J. M. Foody, T. C. Gerber, A. L. Hinderliter, et al., "2012 accf/aha/acp/aats/pcna/scai/sts guideline for the diagnosis and management of patients with stable ischemic heart disease.," Journal of the American College of Cardiology 60 (24) 2564-2603 (2012).
[15] G. N. Levine, E. R. Bates, J. C. Blankenship, S. R. Bailey, J. A. Bittl, B. Cercek, C. E. Chambers, S. G. Ellis, R. A. Guyton, S. M. Hollenberg, et al., "2011 accf/aha/scai guideline for percutaneous coronary intervention: executive summary.," Journal of the American College of Cardiology 58 (24) 2550-2583 (2011).
[16] L. M. Mielniczuk, G. A. Lamas, G. C. Flaker, G. Mitchell, S. C. Smith, B. J. Gersh, S. D. Solomon, L. A. Moy'e, J. L. Rouleau, J. D. Rutherford, et al., "Left ventricular end-diastolic pressure and risk of subsequent heart failure in patients following an acute myocardial infarction," Congestive Heart Failure 13 (4) 209-214 (2007).
[17] J. J. Russo, N. Aleksova, I. Pitcher, E. Couture, S. Parlow, M. Faraz, S. Visintini, T. Simard, P. Di Santo, R. Mathew, et al., "Left ventricular unloading during extracorporeal membrane oxygenation in patients with cardiogenic shock," Journal of the American College of Cardiology 73 (6) 654-662 (2019).
[18] R. Salem, A. Denault, P. Couture, S. Belisle, A. Fortier, M.-C. Guertin, M. Carrier, R. Martineau, "Left ventricular end-diastolic pressure is a predictor of mortality in cardiac surgery independently of left ventricular ejection fraction," BJA: British Journal of Anaesthesia 97 (3) 292-297(2006).
[19] S. H. Strogatz, "Nonlinear dynamics and chaos: with applications to physics, biology, chemistry, and engineering," CRC Press, (2018).
[20] A. L. Goldberger, D. R. Rigney, B. J. West, "Chaos and fractals in human physiology," Scientific American 262 (2) 42-49 (1990).
[21] A. L. Goldberger, "Nonlinear dynamics, fractals and chaos: applications to cardiac electrophysiology," Annals of biomedical engineering 18 (2) 195-198 (1990).
[22] L. Glass, A. Beuter, D. Larocque, "Time delays, oscillations, and chaos in physiological control systems," Mathematical Biosciences 90 (1-2) 111-125 (1988).
[23] L. Glass, "Synchronization and rhythmic processes in physiology," Nature 410 (6825) 277 (2001).
[24] M. I. Owis, A. H. Abou-Zied, A.-B. Youssef, Y. M. Kadah, "Study of features based on nonlinear dynamical modeling in ecg arrhythmia detection and classification," IEEE transactions on Biomedical Engineering 49 (7) 733-736 (2002).
[25] A. Voss, S. Schulz, R. Schroeder, M. Baumert, P. Caminal, "Methods derived from nonlinear dynamics for analysing heart rate variability, Philosophical Transactions of the Royal Society A: Mathematical," Physical and Engineering Sciences 367 (1887) 277-296 (2008).
[26] L. Glass, P. Hunter, A. McCulloch, "Theory of heart: biomechanics, biophysics, and nonlinear dynamics of cardiac function," Springer Science & Business Media, (2012).
[27] P. Billingsley, "Ergodic theory and information," Vol. 1, Wiley New York, 1965.

[28] T. Sauer, J. A. Yorke, M. Casdagli, "Embedology," Journal of statistical Physics 65 (3-4) 579-616 (1991).

[29] A. Chatterjee, "An introduction to the proper orthogonal decomposition," Current science 808-817 (2000).

[30] A. Wolf, J. B. Swift, H. L. Swinney, J. A. Vastano, "Determining Lyapunov exponents from a time series," Physica D: Nonlinear Phenomena 16 (3) 285-317 (1985).

[31] A. N. Kolmogorov, "Entropy per unit time as a metric invariant of automorphisms," Doklady of Russian Academy of Sciences, Vol. 124, pp. 754-755 (1959).

[32] P. Grassberger, I. Procaccia, "Estimation of the kolmogorov entropy from a chaotic signal," Physical review A 28 (4) 2591 (1983).

[33] J. Theiler, "Efficient algorithm for estimating the correlation dimension from a set of discrete points," Physical review A 36 (9) 4456 (1987).

[34] A. Pikovsky, J. Kurths, M. Rosenblum, J. Kurths, "Synchronization: a universal concept in nonlinear sciences," Vol. 12, Cambridge university press (2003).

[35] D. Dubin, "Rapid interpretation of EKG's: an interactive course," Cover Publishing Company (2000).

[36] F. Pedregosa, G. Varoquaux, A. Gramfort, V. Michel, B. Thirion, O. Grisel, M. Blondel, P. Prettenhofer, R. Weiss, V. Dubourg, et al., "Scikit-learn: Machine learning in python," Journal of machine learning research 12, 2825-2830 (October 2011).

[37] T. Chen, C. Guestrin, "Xgboost: A scalable tree boosting system," Proceedings of the 22nd acm-sigkdd international conference on knowledge discovery and data mining, ACM, pp. 785-794 (2016).

[38] H. Zou, T. Hastie, "Regularization and variable selection via the elastic net," Journal of the royal statistical society: series B (statistical methodology) 67 (2) 301-320 (2005).

What is claimed is:

1. A method for non-invasively assessing a cardiac disease state or condition of a subject, the method comprising:

obtaining, by one or more processors, a biophysical signal data set of a subject, wherein the biophysical signal data set is obtained via two or more surface sensors positioned in proximity to the subject's body and in at least two biophysical signal modalities;

generating, by the one or more processors, a three-dimensional model of the biophysical signal data set;

determining, by the one or more processors, one or more dynamical properties and a Poincaré map of the biophysical signal data set; and determining, by the one or more processors, an alpha shape object of the Poincaré map from the three-dimensional model;

determining, by the one or more processors and using a trained machine learning model, a plurality of geometric properties of the alpha shape object, wherein the plurality of geometric properties includes at least one property selected from the group consisting of: a density value of the alpha shape object, a convex surface area value of the alpha shape object, a perimeter value of the alpha shape object, a porosity value of the alpha shape object, and a void area value of the alpha shape object;

determining, by the one or more processors, one or more estimated values for the presence, non-presence, localization, and/or severity of the cardiac disease or condition based on the determined one or more dynamical properties and the plurality of determined geometric properties of the alpha shape object, wherein the one or more estimated values are used in a diagnosis of the cardiac disease state or condition and to administer treatment for the cardiac disease state or condition, and wherein the treatment comprises placing a stent in the coronary artery, performing an atherectomy, performing an angioplasty, or administering a medication.

2. The method of claim 1, wherein the cardiac disease state or condition includes coronary artery disease.

3. The method of claim 1, further comprising:

determining, by the one or more processors, one or more second estimated values for the presence, non-presence, localization, and/or severity of two or more of the cardiac diseases or conditions.

4. The method of claim 1, wherein a dynamical property of the one or more dynamical properties is selected from the group consisting of entropy value (K2), fractal dimension (D2), Lyapunov exponent, auto correlation, auto mutual information, cross-correlation, and mutual information.

5. The method of claim 1 further comprising:

causing, by the one or more processors, generation of a visualization of the estimated value for the presence, non-presence, localization, and/or severity of the cardiac disease or condition, wherein the generated visualization is rendered and displayed at a display of a computing device and/or presented in a report.

6. The method of claim 1, wherein the plurality of determined geometric properties further includes two or more properties selected from the group of:

a length of semi axis "a" for an assessed largest cluster ellipse of the Poincaré map;

a length of semi axis "b" for an assessed largest cluster ellipse of the Poincaré map;

a length of a longest axis of an assessed largest cluster ellipse of the Poincaré map;

a length of a shortest axis of an assessed largest cluster ellipse of the Poincaré map;

an assessed number of clusters in the Poincaré map;

an assessed number of kernel density modes in a histogram map; and a Sarles bimodality coefficient value assessed from the histogram map.

7. The method of claim 1, wherein at least one of the sensors includes a light-emitting diode operatively coupled to a phototransistor.

8. The method of claim 1, wherein the plurality of geometric properties includes the density value of the alpha shape object as a surface area normalized by an overall number of data points.

* * * * *